(12) United States Patent
Sanchez

(10) Patent No.: US 11,034,677 B2
(45) Date of Patent: Jun. 15, 2021

(54) COUMARIN-BASED COMPOUNDS AND RELATED METHODS

(71) Applicant: Biosearch Technologies, Inc., Petaluma, CA (US)

(72) Inventor: Anthony de Jesus Sanchez, Oakland, CA (US)

(73) Assignee: BIOSEARCH TECHNOLOGIES, INC., Petaluma, CA (US)

( * ) Notice: Subject to any disclaimer, the term of this patent is extended or adjusted under 35 U.S.C. 154(b) by 679 days.

(21) Appl. No.: 14/998,576

(22) Filed: Jan. 19, 2016

(65) Prior Publication Data

US 2017/0015652 A1 Jan. 19, 2017

Related U.S. Application Data

(60) Provisional application No. 62/125,431, filed on Jan. 20, 2015.

(51) Int. Cl.
| | | |
|---|---|---|
| *C07D 405/06* | (2006.01) | |
| *C07H 21/04* | (2006.01) | |
| *C07D 491/16* | (2006.01) | |
| *C07D 491/052* | (2006.01) | |
| *C07D 311/12* | (2006.01) | |

(52) U.S. Cl.
CPC .......... *C07D 405/06* (2013.01); *C07D 311/12* (2013.01); *C07D 491/052* (2013.01); *C07D 491/16* (2013.01); *C07H 21/04* (2013.01)

(58) Field of Classification Search
CPC ................ C07D 405/06; C07D 311/12; C07D 491/052; C07D 491/16; C07H 21/04
USPC ....................................................... 536/23.1
See application file for complete search history.

(56) References Cited

U.S. PATENT DOCUMENTS

| | | |
|---|---|---|
| 6,495,676 B1 | 12/2002 | Wood et al. |
| 2004/0191796 A1 | 9/2004 | Reed |
| 2007/0196852 A1 | 8/2007 | Heindl et al. |
| 2009/0197254 A1 | 8/2009 | Lee et al. |
| 2010/0029017 A1 | 2/2010 | Diwu et al. |
| 2010/0136567 A1 | 6/2010 | Carter et al. |
| 2011/0172420 A1 | 7/2011 | Zilles et al. |
| 2012/0016128 A1 | 1/2012 | Diwu et al. |

FOREIGN PATENT DOCUMENTS

| | | | |
|---|---|---|---|
| CN | 1084219 | 3/1994 | |
| EP | 1 842 923 A1 | 2/2007 | |
| JP | 2003-516163 | 5/2003 | |
| JP | 2007-224028 | 9/2007 | |
| WO | WO 1994/02644 | 2/1994 | |
| WO | WO 96/28438 | 9/1996 | |
| WO | WO 2001/42505 | 6/2001 | |
| WO | WO-2009061911 A1 * | 5/2009 | ......... G01N 33/5008 |

OTHER PUBLICATIONS

Cheng, T.J.R. et al., "High-throughput Identification of Antibacterials Against Methicillin . . . " Bioorganic & Medicinal Chemistry (2010) vol. 18, pp. 8512-8529.
Franzini, et al., "7-Azidomethoxy-coumarins as Profluorophores for Templated Nucleic Acid Detection," ChemBioChem (2008) vol. 9, pp. 2981-2988.
Bhan, et al., "Photo-Cross-Linking of Psoralen-derivatized Oligonucleoside Methylphosphonates . . . ," Bioconjugate Chem (1990) vol. 1, pp. 82-88.
Fischer, et al., "Synthesis and Use of an In-solution Rationmetric Fluorescent Viscosity Sensor," Protocol (2007) http://doi:10.1038/nprot.2006.455.
Veselovskaya, et al., "Modified Coumarins. 32. Synthesis of Amino-acid Derivatives of Dihydropyranocoumarins," Chem.Nat.Compd. (2009) vol. 45:2, pp. 169-173.
Guasch, et al., "Identification of PPARgamma Partial Agonists of Natural Origin . . . ," Plos One (2012) p. e50816.
Dutta et al. Bioconjugate Chem., 2013, 24, 1533.
Lin et al. New Technologies in Cytometry, 1989, 1063, 133.
Mergny, et al. Nucleic Acids Research, 1994, 22, 920.
Veselovskaya, M. et al. Zh. Org. Farm. Khim. 2004, 2, 54.
Webb et al. Biophysical J. 2001, 81, 1562.
Written Opinion of Intellectual Property Office of Singapore, dated Oct. 18, 2019 (SG Application No. 11201705411S).
Compound in Database Registry (STN online), ACS, Apr. 13, 2008.
Compound in Database Registry (STN online), ACS, Jun. 7, 2009.
Compound in Database Registry (STN online), ACS, Aug. 30, 2009.
Compound in Database Registry (STN online), ACS, Aug. 10, 2010.
Compound in Database Registry (STN online), ACS, Dec. 2, 2012.
Compound in Database Registry (STN online), ACS, Oct. 21, 2013.
Database Registry, Chemical Abstracts Services, STN Accession No. 1577310-46-3 (Entered STN: Mar. 31, 2014); 919740-16-2 (Entered STN: Feb. 7, 2007) (see p. 5 of Written Opinion of Intellectual Property Office of Singapore, dated Oct. 18, 2019 (SG Application No. 11201705411S for relevant compounds).
Database Registry, Chemical Abstracts Services, STN Accession No. 1318375-04-0 (Entered STN: Aug. 16, 2011); see p. 5 of Written Opinion of Intellectual Property Office of Singapore, dated Oct. 18, 2019 (SG Application No. 11201705411S for relevant compounds).
Database Registry, Chemical Abstracts Services, STN Accession No. 1209332-43-3 (Entered STN: Mar. 12, 2010); see p. 5 of Written Opinion of Intellectual Property Office of Singapore, dated Oct. 18, 2019 (SG Application No. 11201705411S for relevant compounds).

(Continued)

*Primary Examiner* — Jezia Riley
(74) *Attorney, Agent, or Firm* — Morgan, Lewis & Bockius LLP; Jeffry S. Mann

(57) ABSTRACT

The present invention generally relates to coumarin-based compounds that can be used for the labeling of biological molecules, as well as related synthetic and testing methods. The coumarin-based compounds typically survive conditions necessary for automated synthesis of nucleic acids without undergoing any substantial degree of degradation or alteration.

25 Claims, No Drawings

Specification includes a Sequence Listing.

(56) References Cited

OTHER PUBLICATIONS

Database Registry, Chemical Abstracts Services, STN Accession No. 919740-16-2 (Entered STN: Feb. 7, 2007) (see p. 5 of Written Opinion of Intellectual Property Office of Singapore, dated Oct. 18, 2019 (SG Application No. 11201705411S for relevant compounds).
Written Opinion of Intellectual Property Office of Singapore, dated Feb. 14, 2014 (SG Application No. 11201705411S.
Database Registry, Chemical Abstracts Services, STN Accession No. 1607183-82-3 (May 21, 2014 entered STN); see p. 5 of Written Opinion of Intellectual Property Office of Singapore, dated Feb. 14, 2014 (SG Application No. 11201705411S for relevant compounds).
Database Registry, Chemical Abstracts Services, STN Accession No. 1596521-49-1 [May 4, 2014]; see p. 5 of Written Opinion of Intellectual Property Office of Singapore, dated Feb. 14, 2014 (SG Application No. 11201705411S for relevant compounds).
Database Registry, Chemical Abstracts Services, STN Accession No. 1589245-12-4 (Apr. 25, 2014 entered STN); see p. 5 of Written Opinion of Intellectual Property Office of Singapore, dated Feb. 14, 2014 (SG Application No. 11201705411S for relevant compounds).
Database Registry, Chemical Abstracts Services, STN Accession No. 1486347-35-6 (Dec. 4, 2013 entered STN); see p. 5 of Written Opinion of Intellectual Property Office of Singapore, dated Feb. 14, 2014 (SG Application No. 11201705411S for relevant compounds).
Database Registry, Chemical Abstracts Services, STN Accession No. 1266350-42-8 (Mar. 4, 2011 entered STN); see p. 5 of Written Opinion of Intellectual Property Office of Singapore, dated Feb. 14, 2014 (SG Application No. 11201705411S for relevant compounds).
Database Registry, Chemical Abstracts Services, STN Accession No. 866325-28-2 (Aug. 29, 2003 entered STN); see p. 5 of Written Opinion of Intellectual Property Office of Singapore, dated Feb. 14, 2014 (SG Application No. 11201705411S for relevant compounds).
Database Registry, Chemical Abstracts Services, STN Accession No. 1623849-81-9 (Sep. 21, 2014 entered STN); see p. 5 of Written Opinion of Intellectual Property Office of Singapore, dated Feb. 14, 2014 (SG Application No. 11201705411S for relevant compounds).
Database Registry, Chemical Abstracts Services, STN Accession No. 1490190-84-5 (Dec. 9, 2013 entered STN); see p. 5 of Written Opinion of Intellectual Property Office of Singapore, dated Feb. 14, 2014 (SG Application No. 11201705411S for relevant compounds).
Database Registry, Chemical Abstracts Services, STN Accession No. 933606-43-0 (Apr. 29, 2007 entered STN); see p. 5 of Written Opinion of Intellectual Property Office of Singapore, dated Feb. 14, 2014 (SG Application No. 11201705411S for relevant compounds).
Database Registry, Chemical Abstracts Services, STN Accession No. 1992072-08-8 (Sep. 13, 2016 entered STN); see p. 5 of Written Opinion of Intellectual Property Office of Singapore, dated Feb. 14, 2014 (SG Application No. 11201705411S for relevant compounds).
Database Registry, Chemical Abstracts Services, STN Accession No. 1607236-93-0 (May 21, 2014 entered STN); see p. 5 of Written Opinion of Intellectual Property Office of Singapore, dated Feb. 14, 2014 (SG Application No. 11201705411S for relevant compounds).
Database Registry, Chemical Abstracts Services, STN Accession No. 1416162-64-5 (Jan. 8, 2013 entered STN); see p. 5 of Written Opinion of Intellectual Property Office of Singapore, dated Feb. 14, 2014 (SG Application No. 11201705411S for relevant compounds).
Database Registry, Chemical Abstracts Services, STN Accession No. 1386233-06-2 (Aug. 3, 2012 entered STN); see p. 5 of Written Opinion of Intellectual Property Office of Singapore, dated Feb. 14, 2014 (SG Application No. 11201705411S for relevant compounds).
Database Registry, Chemical Abstracts Services, STN Accession No. 939886-90-5 (Jun. 28, 2007 entered STN); see p. 5 of Written Opinion of Intellectual Property Office of Singapore, dated Feb. 14, 2014 (SG Application No. 11201705411S for relevant compounds).
Database Registry, Chemical Abstracts Services, STN Accession No. 1333664-34-8 (Sep. 29, 2011 entered STN); see p. 5 of Written Opinion of Intellectual Property Office of Singapore, dated Feb. 14, 2014 (SG Application No. 11201705411S for relevant compounds).
Database Registry, Chemical Abstracts Services, STN Accession No. 1325870-44-7 (Aug. 31, 2011 entered STN); see p. 5 of Written Opinion of Intellectual Property Office of Singapore, dated Feb. 14, 2014 (SG Application No. 11201705411S for relevant compounds).
Database Registry, Chemical Abstracts Services, STN Accession No. 859859-08-8 (Aug. 12, 2005 entered STN); see p. 5 of Written Opinion of Intellectual Property Office of Singapore, dated Feb. 14, 2014 (SG Application No. 11201705411S for relevant compounds).
Database Registry, Chemical Abstracts Services, Stn Accession Number: 1434001-60-1 (03 Jun 2013 entered Stn); see p. 5 of Written Opinion of Intellectual Property Office of Singapore, dated Feb. 14, 2014 (Sg Application No. 11201705411S for relevant compounds).

* cited by examiner

COUMARIN-BASED COMPOUNDS AND RELATED METHODS

FIELD OF THE INVENTION

The present invention generally relates to coumarin-based compounds that can be used for the labeling of biological molecules, as well as related synthetic and testing methods.

BACKGROUND OF THE INVENTION

Researchers have investigated the use of coumarins for labeling oligonucleotides. They have noted inherent difficulties associated with the synthetic manipulation of such compounds: "[C]oumarin dyes represent brightly emitting organic fluorophores that are not stable under the typically strong basic conditions during DNA cleavage and deprotection. Hence, these labels cannot be incorporated into oligonucleotides using conventional phosphoramidite chemistry." Berndl, S. et al. "Comparison of a Nucleosidic vs Non-Nucleosidic Postsynthetic 'Click' Modification of DNA with Base-Labile Fluorescent Probes" *Bioconjugate Chem.* 2009, 20, 558-564.

Coumarins have been conjugated to oligonucleotides post-synthetically using "click" and activated ester chemistries. There are few examples of coumarins being incorporated into oligonucleotides using corresponding coumarin phosphoramidites. US2004191796, for example, discusses a single coumarin phosphoramidite (Structure 1), as shown below:

Structure 1

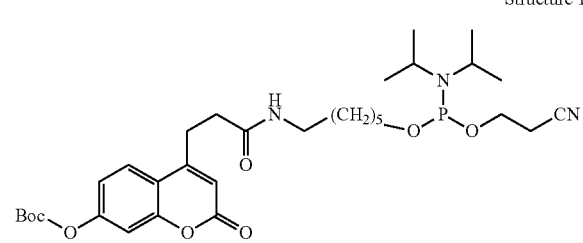

WO1996028438 discusses a few coumarin phosphoramidites (Structures 2-5). In all cases, the phosphoramidite portion is attached to the coumarin aromatic ring. Hot ammonia was used to deprotect the corresponding oligonucleotides.

Structure 2

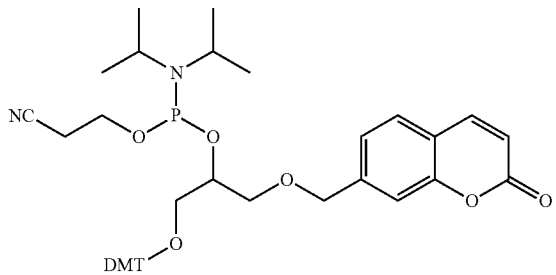

Structure 3

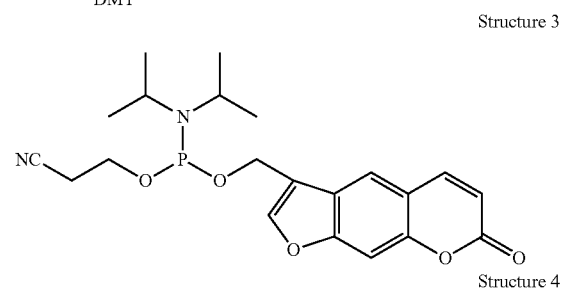

Structure 4

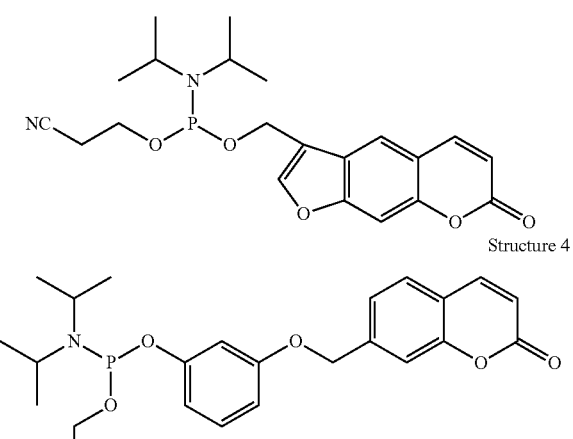

Structure 5

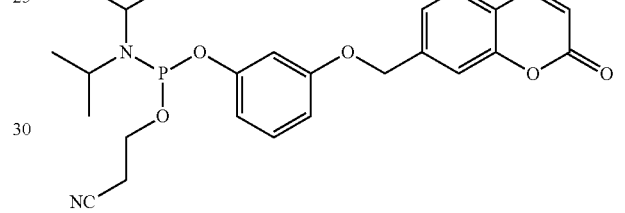

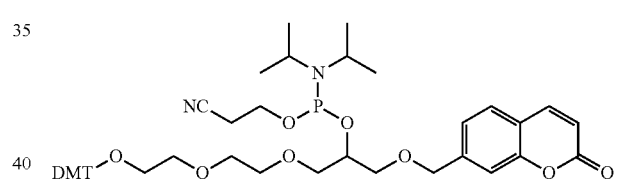

EP 1842923 is directed to dye-labeled nucleotide derivatives. The reference discusses a coumarin linked through a methanesulfonylaminoindole to a phosphoramidite. Oligonucleotides prepared from this reagent were deprotected using ammonia at room temperature for 2 hours. This compound, Structure 6, is sold as Cyan 500 by Roche.

Structure 6

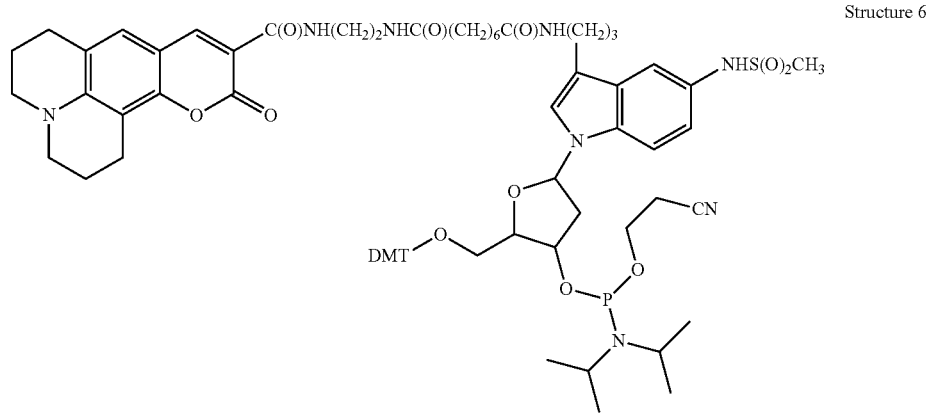

Kobertz et al. reports a psoralen-based ribose phosphoramidite (Structure 7) *J. Am. Chem. Soc.,* 1997, 119 (25), pp 5960-5961. The reference discusses preparation of oligonucleotides using such compounds together with PAC-protected phosphoramidites. Products were cleaved and deprotected with 10% DBU in EtOH at room temperature for 24 hours.

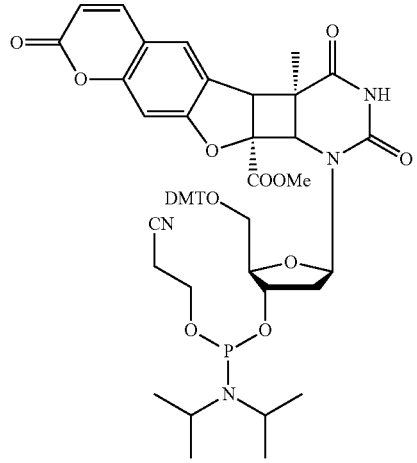

Structure 7

Brauns et al. reports a coumarin C-riboside phosphoramidite (Structure 8) *J. Am. Chem. Soc.,* 1999, 121 (50), pp 11644-11649. Cleavage of a corresponding oligonucleotide from a support and deprotection was accomplished by treatment with concentrated $NH_4OH$ for 16 hours at 25° C.

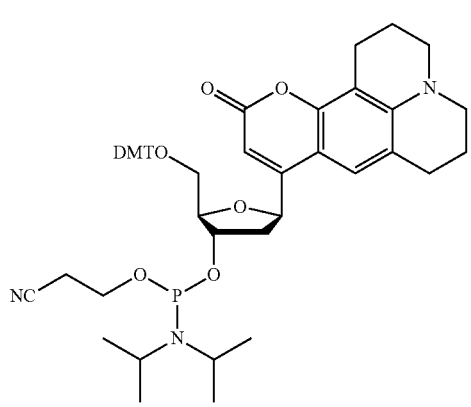

Structure 8

Ivana et al. reports a single coumarin phosphoramidite (Structure 9) *Collect. Czech. Chem. Commun.* 2007, 72, 996-1004. The reference does not discuss any example of DNA synthesis.

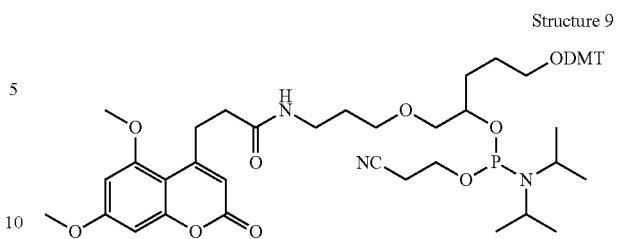

Structure 9

Goguen et al. reports the preparation of a coumarin phosphoramidite as an intermediate in the preparation of phosphoamino acids (Structure 10) *J. Am. Chem. Soc.,* 2011, 133 (29), pp 11038-11041.

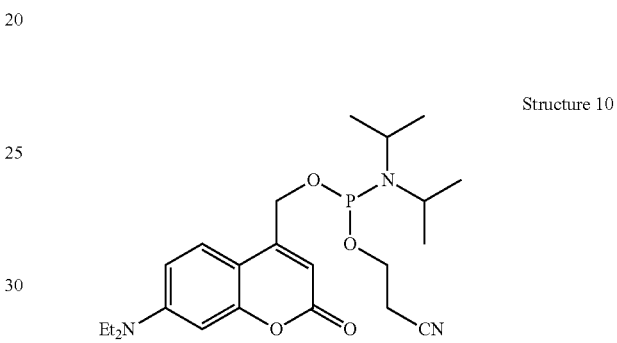

Structure 10

Menge et al. reports the preparation of a coumarin linked to a nucleotide phosphoramidite through the nucleobase (Structure 11) *Org. Lett.,* 2011, 13 (17), pp 4620-4623. The corresponding oligonucleotide synthesized using the phosphoramidite was cleaved and deprotected with ammonia at room temperature.

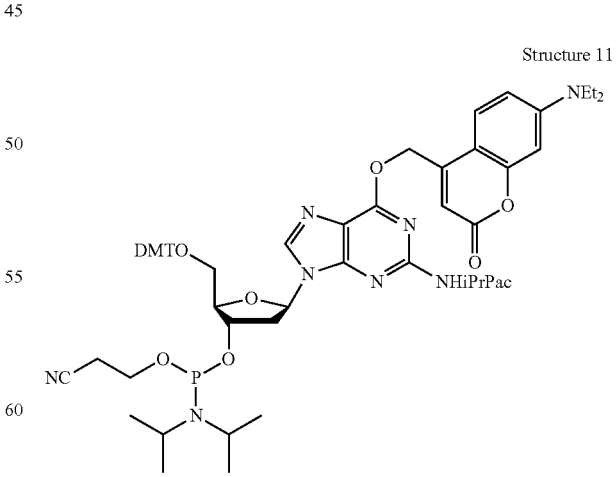

Structure 11

Sun et al. reports the use of an alkyne modified coumarin phosphoramidite in click conjugation (Structure 12) *Bioconj. Chem.* 2013, 24(7):1226-34.

Structure 12

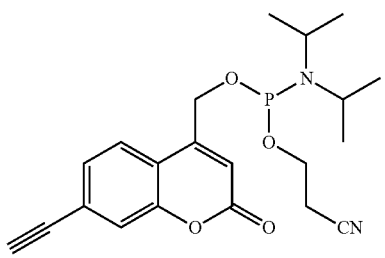

SUMMARY OF THE INVENTION

In one aspect, the present invention provides a compound of Structure 14:

Structure 14

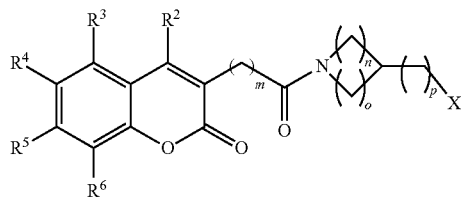

The integer m is 0, 1, 2, 3, 4, 5, 6, 7, 8, 9 or 10. The integer n is 0, 1, 2 or 3. The integer o is 0, 1, 2 or 3. The integer p is 0, 1, 2, 3, 4, 5, 6, 7, 8, 9 or 10.

$R^2$ is selected from a group consisting of —H or —CH$_3$;

$R^3$ is selected from a group consisting of —H, -halogen, —CF$_3$, —OH, —NH$_2$, —CCH, —CN, —NO$_2$, (C$_1$-C$_8$) alkyl, (C$_1$-C$_8$)substituted alkyl, (C$_1$-C$_8$)alkylthio, (C$_1$-C$_8$) substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, or R$^7$ and R$^8$ together form a four-, five-, six-, or seven-membered heterocycle, (C$_1$-C$_8$) heteroalkyl, (C$_1$-C$_8$)substituted heteroalkyl, aryl, substituted aryl, heteroaryl, substituted heteroaryl, or R$^3$ together with R$^4$ form a five- or six-membered carbocyclic or heterocyclic ring (e.g., piperidinyl);

$R^4$ is selected from a group consisting of —H, -halogen, —CF$_3$, —OH, —NH$_2$, —CCH, —CN, —NO$_2$, (C$_1$-C$_8$) alkyl, (C$_1$-C$_8$)substituted alkyl, (C$_1$-C$_8$)alkylthio, (C$_1$-C$_8$) substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, or R$^7$ and R$^8$ together form a four-, five-, six-, or seven-membered heterocycle, (C$_1$-C$_8$) heteroalkyl, (C$_1$-C$_8$)substituted heteroalkyl, aryl, substituted aryl, heteroaryl, substituted heteroaryl, or R$^4$ together with R$^5$ form a five- or six-membered carbocyclic or heterocyclic ring (e.g., piperidinyl);

$R^5$ is selected from a group consisting of —H, -halogen, —CF$_3$, —OH, —NH$_2$, —CCH, —CN, —NO$_2$, (C$_1$-C$_8$) alkyl, (C$_1$-C$_8$)substituted alkyl, (C$_1$-C$_8$)alkylthio, (C$_1$-C$_8$) substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, or R$^7$ and R$^8$ together form a four-, five-, six-, or seven-membered heterocycle, (C$_1$-C$_8$) heteroalkyl, (C$_1$-C$_8$)substituted heteroalkyl, aryl, substituted aryl, heteroaryl, substituted heteroaryl, or R$^5$ together with R$^6$ form a five- or six-membered carbocyclic or heterocyclic ring (e.g., piperidinyl); or R$^4$, R$^5$ and R$^6$ together form fused carbocyclic or heterocyclic ring systems having five- or six-membered rings;

$R^6$ is selected from a group consisting of —H, -halogen, —CF$_3$, —OH, —NH$_2$, —CCH, —CN, —NO$_2$, (C$_1$-C$_8$) alkyl, (C$_1$-C$_8$)substituted alkyl, (C$_1$-C$_8$)alkylthio, (C$_1$-C$_8$) substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, (C$_1$-C$_8$)substituted alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl;

X is —OH, —NH$_2$, —SH, —OR$^{11}$, —NHR$^{12}$, —NR$^{13}$R$^{14}$, —OC(O)R$^{15}$, —NHC(O)R$^{16}$, —SC(O)R$^{17}$, —C(O)OH, —C(O)OR$^{18}$, —C(O)NHR$^{19}$, —C(O)NR$^{20}$R$^{21}$, —N$_3$;

R$^{11}$, R$^{12}$, R$^{13}$, R$^{14}$, R$^{15}$, R$^{16}$, R$^{17}$, R$^{18}$, R$^{19}$, R$^{20}$ and R$^{21}$ are independently selected from (C$_1$-C$_8$)alkyl, (C$_1$-C$_8$)substituted alkyl, —CH$_2$CH(OH)CH$_2$(OH), —CH(CH$_2$OH)$_2$, —CH$_2$CCH, —(CH$_2$CH$_2$O)$_a$—CH$_2$CH$_2$OH where a is 1, 2, 3, 4, 5, 6, 7, 8, 9 or 10, —P(NR$^{22}$R$^{23}$)OCH$_2$CH$_2$-EWG, -P(O)(O—)- Oligonucleotide, —(CH$_2$)$_b$CC-Nucleoside, —(CH$_2$)$_b$CC-[Nucleoside Triphosphate], —(CH$_2$)$_b$-Nucleoside, —(CH$_2$)$_b$-[Nucleoside Triphosphate], —(CH$_2$)$_b$NH-Nucleoside, —(CH$_2$)$_b$NH-[Nucleoside Triphosphate], —(CH$_2$)$_b$NHC(O)(CH$_2$)$_b$-Nucleoside, —(CH$_2$)$_b$NHC(O) (CH$_2$)$_b$-[Nucleoside Triphosphate], where b is 1, 2, 3, 4, 5, 6, 7, 8, 9 or 10;

EWG is an electron withdrawing group;

R$^{22}$ and R$^{23}$ are independently selected from —CH$_3$, —CH$_2$CH$_3$, —CH(CH$_3$)$_2$ or R$^{22}$ and R$^{23}$ together form a heterocycle.

In other aspects, the present invention provides:

A compound of the structure below:

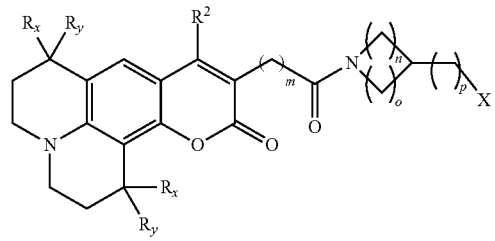

where
m is 0, 1, 2, 3, 4, 5, 6, 7, 8, 9 or 10;
n is 0, 1, 2 or 3;
o is 0, 1, 2 or 3;
p is 0, 1, 2, 3, 4, 5, 6, 7, 8, 9 or 10;
$R^2$ is selected from a group consisting of —H or —CH$_3$;
X is —OH, —NH$_2$, —SH, —OR$^{11}$, —NHR$^{12}$, —NR$^{13}$R$^{14}$, —OC(O)R$^{15}$, —NHC(O)R$^{16}$, —SC(O)R$^{17}$, —C(O)OH, —C(O)OR$^{18}$, —C(O)NHR$^{19}$, —C(O)NR$^{20}$R$^{21}$, —N$_3$;

R$^{11}$, R$^{12}$, R$^{13}$, R$^{14}$, R$^{15}$, R$^{16}$, R$^{17}$, R$^{18}$, R$^{19}$, R$^{20}$ and R$^{21}$ are independently selected from (C$_1$-C$_8$)alkyl, (C$_1$-C$_8$)substituted alkyl, —CH$_2$CH(OH)CH$_2$(OH), —CH(CH$_2$OH)$_2$, —CH$_2$CCH, —(CH$_2$CH$_2$O)$_a$—CH$_2$CH$_2$OH where a is 1, 2, 3, 4, 5, 6, 7, 8, 9 or 10, —P(NR$^{22}$R$^{23}$)OCH$_2$CH$_2$-EWG, —P(O)(O—)-Oligonucleotide, —(CH$_2$)$_b$CC-Nucleoside, —(CH$_2$)$_b$CC-[Nucleoside Triphosphate], —(CH$_2$)$_b$-Nucleoside, —(CH$_2$)$_b$-[Nucleoside Triphosphate], —(CH$_2$)$_b$NH-Nucleoside, —(CH$_2$)$_b$NH-[Nucleoside Triphosphate], —(CH$_2$)$_b$NHC(O)(CH$_2$)$_b$-Nucleoside, —(CH$_2$)$_b$NHC(O)(CH$_2$)$_b$-[Nucleoside Triphosphate], where b is 1, 2, 3, 4, 5, 6, 7, 8, 9 or 10;

EWG is an electron withdrawing group;

R$_x$ and R$_y$ are independently H or CH$_3$;

R$^{22}$ and R$^{23}$ are independently selected from —CH$_3$, —CH$_2$CH$_3$, —CH(CH$_3$)$_2$ or R$^{22}$ and R$^{23}$ together form a heterocycle.

The compound listed above, wherein m is 0, 1, 2 or 3, n is 1 or 2, o is 1 or 2, and p is 0, 1, 2 or 3.

The compound listed above, wherein X is —OH, —OR$^{11}$, or —OC(O)R$^{15}$.

The compound listed above, wherein X is —NH$_2$, —NHR$^{12}$, —NR$^{13}$R$^{14}$, —NHC(O)R$^{16}$.

A compound of the structure below:

where m is 0, 1, 2, 3, 4, 5, 6, 7, 8, 9 or 10;

n is 0, 1, 2 or 3;

o is 0, 1, 2 or 3;

p is 0, 1, 2, 3, 4, 5, 6, 7, 8, 9 or 10;

R$^2$ is selected from a group consisting of —H or —CH$_3$;

R$^7$ and R$^8$ are independently selected from H, (C$_1$-C$_8$)alkyl, (C$_1$-C$_8$)substituted alkyl, or R$^7$ and R$^8$ together form a five-, six-, or seven-membered heterocycle;

X is —OH, —NH$_2$, —SH, —OR$^{11}$, —NHR$^{12}$, —NR$^{13}$R$^{14}$, —OC(O)R$^{15}$, —NHC(O)R$^{16}$, —SC(O)R$^{17}$, —C(O)OH, —C(O)OR$^{18}$, —C(O)NHR$^{19}$, —C(O)NR$^{20}$R$^{21}$, —N$_3$;

R$^{11}$, R$^{12}$, R$^{13}$, R$^{14}$, R$^{15}$, R$^{16}$, R$^{17}$, R$^{18}$, R$^{19}$, R$^{20}$ and R$^{21}$ are independently selected from (C$_1$-C$_8$)alkyl, (C$_1$-C$_8$)substituted alkyl, —CH$_2$CH(OH)CH$_2$(OH), —CH(CH$_2$OH)$_2$, —CH$_2$CCH, —(CH$_2$CH$_2$O)$_a$—CH$_2$CH$_2$OH where a is 1, 2, 3, 4, 5, 6, 7, 8, 9 or 10, —P(NR$^{22}$R$^{23}$)OCH$_2$CH$_2$-EWG, —P(O)(O—)-Oligonucleotide, —(CH$_2$)$_b$CC-Nucleoside, —(CH$_2$)$_b$CC-[Nucleoside Triphosphate], —(CH$_2$)$_b$-Nucleoside, —(CH$_2$)$_b$-[Nucleoside Triphosphate], —(CH$_2$)$_b$NH-Nucleoside, —(CH$_2$)$_b$NH-[Nucleoside Triphosphate], —(CH$_2$)$_b$NHC(O)(CH$_2$)$_b$-Nucleoside, —(CH$_2$)$_b$NHC(O)(CH$_2$)$_b$-[Nucleoside Triphosphate], where b is 1, 2, 3, 4, 5, 6, 7, 8, 9 or 10;

EWG is an electron withdrawing group;

R$^{22}$ and R$^{23}$ are independently selected from —CH$_3$, —CH$_2$CH$_3$, —CH(CH$_3$)$_2$ or R$^{22}$ and R$^{23}$ together form a heterocycle.

The compound listed above, wherein m is 0, 1, 2 or 3, n is 1 or 2, o is 1 or 2, p is 0, 1, 2 or 3.

The compound listed above, wherein R$^7$ and R$^8$ are independently selected from H or (C$_1$-C$_8$)alkyl.

The compound listed above, wherein X is —OH, —OR$^{11}$, or —OC(O)R$^{15}$.

The compound listed above, wherein X is —NH$_2$, —NHR$^{12}$, —NR$^{13}$R$^{14}$, —NHC(O)R$^{16}$.

A compound of the structure below:

where m is 0, 1, 2, 3, 4, 5, 6, 7, 8, 9 or 10;

n is 0, 1, 2 or 3;

o is 0, 1, 2 or 3;

p is 0, 1, 2, 3, 4, 5, 6, 7, 8, 9 or 10;

R$^2$ is selected from a group consisting of —H or —CH$_3$;

the dashed line represents an optional double bond;

X is —OH, —NH$_2$, —SH, —OR$^{11}$, —NHR$^{12}$, —NR$^{13}$R$^{14}$, —OC(O)R$^{15}$, —NHC(O)R$^{16}$, —SC(O)R$^{17}$, —C(O)OH, —C(O)OR$^{18}$, —C(O)NHR$^{19}$, —C(O)NR$^{20}$R$^{21}$, —N$_3$;

R$^{11}$, R$^{12}$, R$^{13}$, R$^{14}$, R$^{15}$, R$^{16}$, R$^{17}$, R$^{18}$, R$^{19}$, R$^{20}$ and R$^{21}$ are independently selected from (C$_1$-C$_8$)alkyl, (C$_1$-C$_8$)substituted alkyl, —CH$_2$CH(OH)CH$_2$(OH), —CH(CH$_2$OH)$_2$, —CH$_2$CCH, —(CH$_2$CH$_2$O)$_a$—CH$_2$CH$_2$OH where a is 1, 2, 3, 4, 5, 6, 7, 8, 9 or 10, —P(NR$^{22}$R$^{23}$)OCH$_2$CH$_2$-EWG, —P(O)(O—)-Oligonucleotide, —(CH$_2$)$_b$CC-Nucleoside, —(CH$_2$)$_b$CC-[Nucleoside Triphosphate], —(CH$_2$)$_b$-Nucleoside, —(CH$_2$)$_b$-[Nucleoside Triphosphate], —(CH$_2$)$_b$NH-Nucleoside, —(CH$_2$)$_b$NH-[Nucleoside Triphosphate], —(CH$_2$)$_b$NHC(O)(CH$_2$)$_b$-Nucleoside, —(CH$_2$)$_b$NHC(O)(CH$_2$)$_b$-[Nucleoside Triphosphate], where b is 1, 2, 3, 4, 5, 6, 7, 8, 9 or 10;

EWG is an electron withdrawing group;

R$^{22}$ and R$^{23}$ are independently selected from —CH$_3$, —CH$_2$CH$_3$, —CH(CH$_3$)$_2$ or R$^{22}$ and R$^{23}$ together form a heterocycle;

R$^{24}$ is (C$_1$-C$_8$)alkyl or (C$_1$-C$_8$)substituted alkyl;

R$^{25}$ is (C$_1$-C$_8$)alkyl, (C$_1$-C$_8$)substituted alkyl or CH$_2$SO$_3$H.

The compound listed above, wherein m is 0, 1, 2, or 3, n is 1 or 2, o is 1 or 2, p is 0, 1, 2 or 3.

The compound listed above, wherein X is —OH, —OR$^{11}$, or —OC(O)R$^{15}$.

The compound listed above, wherein R$^{24}$ and R$^{25}$ are (C$_1$-C$_8$)alkyl.

A compound of the structure below:

where m is 0, 1, 2, 3, 4, 5, 6, 7, 8, 9 or 10;

n is 0, 1, 2 or 3;

o is 0, 1, 2 or 3;

p is 0, 1, 2, 3, 4, 5, 6, 7, 8, 9 or 10;

R$^1$ is selected from a group consisting of —H or —CH$_3$;

R³ is selected from a group consisting of —H, -halogen, —CF₃, —OH, —NH₂, —CCH, —CN, —NO₂, (C₁-C₈) alkyl, (C₁-C₈)substituted alkyl, (C₁-C₈)alkylthio, (C₁-C₈) substituted alkylthio, (C₁-C₈)alkoxy, (C₁-C₈)substituted alkoxy, —NR⁷R⁸ where R⁷ and R⁸ are independently selected from H, (C₁-C₈)alkyl, or R⁷ and R⁸ together form a four-, five-, six-, or seven-membered heterocycle, (C₁-C₈) heteroalkyl, (C₁-C₈)substituted heteroalkyl, aryl, substituted aryl, heteroaryl, substituted heteroaryl, or R³ together with R⁴ form a five- or six-membered carbocyclic or heterocyclic ring (e.g., piperidinyl);

R⁴ is selected from a group consisting of —H, -halogen, —CF₃, —OH, —NH₂, —CCH, —CN, —NO₂, (C₁-C₈) alkyl, (C₁-C₈)substituted alkyl, (C₁-C₈)alkylthio, (C₁-C₈) substituted alkylthio, (C₁-C₈)alkoxy, (C₁-C₈)substituted alkoxy, —NR⁷R⁸ where R⁷ and R⁸ are independently selected from H, (C₁-C₈)alkyl, or R⁷ and R⁸ together form a four-, five-, six-, or seven-membered heterocycle, (C₁-C₈) heteroalkyl, (C₁-C₈)substituted heteroalkyl, aryl, substituted aryl, heteroaryl, substituted heteroaryl, or R⁴ together with R⁵ form a five- or six-membered carbocyclic or heterocyclic ring (e.g., piperidinyl);

R⁵ is selected from a group consisting of —H, -halogen, —CF₃, —OH, —NH₂, —CCH, —CN, —NO₂, (C₁-C₈) alkyl, (C₁-C₈)substituted alkyl, (C₁-C₈)alkylthio, (C₁-C₈) substituted alkylthio, (C₁-C₈)alkoxy, (C₁-C₈)substituted alkoxy, —NR⁷R⁸ where R⁷ and R⁸ are independently selected from H, (C₁-C₈)alkyl, or R⁷ and R⁸ together form a four-, five-, six-, or seven-membered heterocycle, (C₁-C₈) heteroalkyl, (C₁-C₈)substituted heteroalkyl, aryl, substituted aryl, heteroaryl, substituted heteroaryl, or R⁵ together with R⁶ form a five- or six-membered carbocyclic or heterocyclic ring (e.g., piperidinyl); or R⁴, R⁵ and R⁶ together form fused carbocyclic or heterocyclic ring systems having five- or six-membered rings;

R⁶ is selected from a group consisting of —H, -halogen, —CF₃, —OH, —NH₂, —CCH, —CN, —NO₂, (C₁-C₈) alkyl, (C₁-C₈)substituted alkyl, (C₁-C₈)alkylthio, (C₁-C₈) substituted alkylthio, (C₁-C₈)alkoxy, (C₁-C₈)substituted alkoxy, —NR⁷R⁸ where R⁷ and R⁸ are independently selected from H, (C₁-C₈)alkyl, (C₁-C₈)substituted alkyl, or R⁷ and R⁸ together form a four-, five-, six-, or seven-membered heterocycle, (C₁-C₈)heteroalkyl, (C₁-C₈)substituted heteroalkyl, aryl, substituted aryl, heteroaryl, substituted heteroaryl;

X is —OH, —NH₂, —SH, —OR¹¹, —NHR¹², —NR¹³R¹⁴, —OC(O)R¹⁵, —NHC(O)R¹⁶, —SC(O)R¹⁷, —C(O)OH, —C(O)OR¹⁸, —C(O)NHR¹⁹, —C(O)NR²⁰R²¹, —N₃;

R¹¹, R¹², R¹³, R¹⁴, R¹⁵, R¹⁶, R¹⁷, R¹⁸, R¹⁹, R²⁰ and R²¹ are independently selected from (C₁-C₈)alkyl, (C₁-C₈)substituted alkyl, —CH₂CH(OH)CH₂(OH), —CH(CH₂OH)₂, —CH₂CCH, —(CH₂CH₂O)ₐ—CH₂CH₂OH where a is 1, 2, 3, 4, 5, 6, 7, 8, 9 or 10, —P(NR²²R²³)OCH₂CH₂-EWG, —P(O)(O—)-Oligonucleotide, —(CH₂)ᵦCC-Nucleoside, —(CH₂)ᵦCC-[Nucleoside Triphosphate], —(CH₂)ᵦ-Nucleoside, —(CH₂)ᵦ-[Nucleoside Triphosphate], —(CH₂)ᵦNH-Nucleoside, —(CH₂)ᵦNH-[Nucleoside Triphosphate], —(CH₂)ᵦNHC(O)(CH₂)ᵦ-Nucleoside, —(CH₂)ᵦNHC(O) (CH₂)ᵦ-[Nucleoside Triphosphate], where b is 1, 2, 3, 4, 5, 6, 7, 8, 9 or 10;

EWG is an electron withdrawing group;

R²² and R²³ are independently selected from —CH₃, —CH₂CH₃, —CH(CH₃)₂ or R²² and R²³ together form a heterocycle.

The compound listed above, wherein m is 0, 1, 2, or 3, n is 1 or 2, o is 1 or 2, p is 0, 1, 2 or 3.

The compound listed above, wherein R³ is —H or (C₁-C₈)alkyl.

The compound listed above, wherein X is —OH, —OR¹¹, or —OC(O)R¹⁵.

A compound of the structure below:

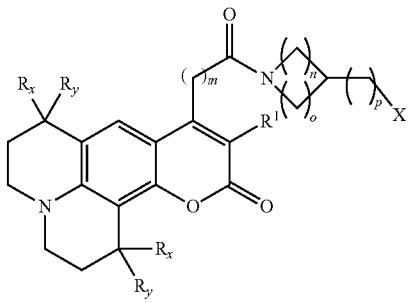

where
m is 0, 1, 2, 3, 4, 5, 6, 7, 8, 9 or 10;
n is 0, 1, 2 or 3;
o is 0, 1, 2 or 3;
p is 0, 1, 2, 3, 4, 5, 6, 7, 8, 9 or 10;
R¹ is selected from a group consisting of —H or —CH₃;
X is —OH, —NH₂, —SH, —OR¹¹, —NHR¹², —NR¹³R¹⁴, —OC(O)R¹⁵, —NHC(O)R¹⁶, —SC(O)R¹⁷, —C(O)OH, —C(O)OR¹⁸, —C(O)NHR¹⁹, —C(O)NR²⁰R²¹, —N₃;
R¹¹, R¹², R¹³, R¹⁴, R¹⁵, R¹⁶, R¹⁷, R¹⁸, R¹⁹, R²⁰ and R²¹ are independently selected from (C₁-C₈)alkyl, (C₁-C₈)substituted alkyl, —CH₂CH(OH)CH₂(OH), —CH(CH₂OH)₂, —CH₂CCH, —(CH₂CH₂O)ₐ—CH₂CH₂OH where a is 1, 2, 3, 4, 5, 6, 7, 8, 9 or 10, —P(NR²²R²³)OCH₂CH₂-EWG, —P(O)(O—)-Oligonucleotide, —(CH₂)ᵦCC-Nucleoside, —(CH₂)ᵦCC-[Nucleoside Triphosphate], —(CH₂)ᵦ-Nucleoside, —(CH₂)ᵦ-[Nucleoside Triphosphate], —(CH₂)ᵦNH-Nucleoside, —(CH₂)ᵦNH-[Nucleoside Triphosphate], —(CH₂)ᵦNHC(O)(CH₂)ᵦ-Nucleoside, —(CH₂)ᵦNHC(O) (CH₂)ᵦ-[Nucleoside Triphosphate], where b is 1, 2, 3, 4, 5, 6, 7, 8, 9 or 10;
R²² and R²³ are independently selected from —CH₃, —CH₂CH₃, —CH(CH₃)₂ or R²² and R²³ together form a heterocycle;
Rₓ and Rᵧ are independently H or CH₃;
EWG is an electron withdrawing group.

The compound listed above, wherein m is 0, 1, 2, or 3, n is 1 or 2, o is 1 or 2, p is 0, 1, 2 or 3.

The compound listed above, wherein X is —OH, —OR¹¹, or —OC(O)R¹⁵.

A compound of the structure below:

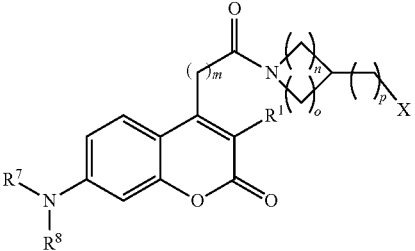

where
    m is 0, 1, 2, 3, 4, 5, 6, 7, 8, 9 or 10;
    n is 0, 1, 2 or 3;
    o is 0, 1, 2 or 3;
    p is 0, 1, 2, 3, 4, 5, 6, 7, 8, 9 or 10;
    $R^1$ is selected from a group consisting of —H or —CH$_3$;
    $R^7$ and $R^8$ are independently selected from H, (C$_1$-C$_8$)alkyl, (C$_1$-C$_8$)substituted alkyl, or $R^7$ and $R^8$ together form a five-, six-, or seven-membered heterocycle;
    X is —OH, —NH$_2$, —SH, —OR$^{11}$, —NHR$^{12}$, —NR$^{13}$R$^{14}$, —OC(O)R$^{15}$, —NHC(O)R$^{16}$, —SC(O)R$^{17}$, —C(O)OH, —C(O)OR$^{18}$, —C(O)NHR$^{19}$, —C(O)NR$^{20}$R$^{21}$, —N$_3$;
    $R^{11}$, $R^{12}$, $R^{13}$, $R^{14}$, $R^{15}$, $R^{16}$, $R^{17}$, $R^{18}$, $R^{19}$ and $R^{20}$ are independently selected from (C$_1$-C$_8$)alkyl, (C$_1$-C$_8$)substituted alkyl, —CH$_2$CH(OH)CH$_2$(OH), —CH(CH$_2$OH)$_2$, —CH$_2$CCH, —(CH$_2$CH$_2$O)$_a$—CH$_2$CH$_2$OH where a is 1, 2, 3, 4, 5, 6, 7, 8, 9 or 10, —P(NR$^{22}$R$^{23}$)OCH$_2$CH$_2$-EWG, —P(O)(O—)-Oligonucleotide, —(CH$_2$)$_b$CC-Nucleoside, —(CH$_2$)$_b$CC-[Nucleoside Triphosphate], —(CH$_2$)$_b$-Nucleoside, —(CH$_2$)$_b$-[Nucleoside Triphosphate], —(CH$_2$)$_b$NH-Nucleoside, —(CH$_2$)$_b$NH-[Nucleoside Triphosphate], —(CH$_2$)$_b$NHC(O)(CH$_2$)$_b$-Nucleoside, —(CH$_2$)$_b$NHC(O)(CH$_2$)$_b$-[Nucleoside Triphosphate], where b is 1, 2, 3, 4, 5, 6, 7, 8, 9 or 10;
    EWG is an electron withdrawing group;
    $R^{22}$ and $R^{23}$ are independently selected from —CH$_3$, —CH$_2$CH$_3$, —CH(CH$_3$)$_2$ or $R^{22}$ and $R^{23}$ together form a heterocycle.

The compound listed above, wherein m is 0, 1, 2, or 3, n is 1 or 2, o is 1 or 2, p is 0, 1, 2 or 3.

The compound listed above, wherein $R^7$ and $R^8$ are independently selected from H and (C$_1$-C$_8$)alkyl.

The compound listed above, wherein X is —OH, —OR$^{11}$, or —OC(O)R$^{15}$.

A compound of the structure below:

where
    m is 0, 1, 2, 3, 4, 5, 6, 7, 8, 9 or 10;
    n is 0, 1, 2 or 3;
    o is 0, 1, 2 or 3;
    p is 0, 1, 2, 3, 4, 5, 6, 7, 8, 9 or 10;
    $R^1$ is selected from a group consisting of —H or —CH$_3$;
    the dashed line represents an optional double bond;
    X is —OH, —NH$_2$, —SH, —OR$^{11}$, —NHR$^{12}$, —NR$^{13}$R$^{14}$, —OC(O)R$^{15}$, —NHC(O)R$^{16}$, —SC(O)R$^{17}$, —C(O)OH, —C(O)OR$^{18}$, —C(O)NHR$^{19}$, —C(O)NR$^{20}$R$^{21}$, —N$_3$;
    $R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from (C$_1$-C$_8$)alkyl, (C$_1$-C$_8$)substituted alkyl, —CH$_2$CH(OH)CH$_2$(OH), —CH(CH$_2$OH)$_2$, —CH$_2$CCH, —(CH$_2$CH$_2$O)$_a$—CH$_2$CH$_2$OH where a is 1, 2, 3, 4, 5, 6, 7, 8, 9 or 10, —P(NR$^{22}$R$^{23}$)OCH$_2$CH$_2$-EWG, —P(O)(O—)-Oligonucleotide, —(CH$_2$)$_b$CC-Nucleoside, —(CH$_2$)$_b$CC-[Nucleoside Triphosphate], —(CH$_2$)$_b$-Nucleoside, —(CH$_2$)$_b$-[Nucleoside Triphosphate], —(CH$_2$)$_b$NH-Nucleoside, —(CH$_2$)$_b$NH-[Nucleoside Triphosphate], —(CH$_2$)$_b$NHC(O)(CH$_2$)$_b$-Nucleoside, —(CH$_2$)$_b$NHC(O)(CH$_2$)$_b$-[Nucleoside Triphosphate], where b is 1, 2, 3, 4, 5, 6, 7, 8, 9 or 10;
    EWG is an electron withdrawing group;
    $R^{22}$ and $R_{23}$ are independently selected from —CH$_3$, —CH$_2$CH$_3$, —CH(CH$_3$)$_2$ or $R^{22}$ and $R^{23}$ together form a heterocycle;
    $R^{24}$ is (C$_1$-C$_8$)alkyl or (C$_1$-C$_8$)substituted alkyl;
    $R^{25}$ is (C$_1$-C$_8$)alkyl, (C$_1$-C$_8$)substituted alkyl or CH$_2$SO$_3$H.

The compound listed above, wherein m is 0, 1, 2, or 3, n is 1 or 2, o is 1 or 2, p is 0, 1, 2 or 3.

The compound listed above, wherein X is —OH, —OR$^{11}$, or —OC(O)R$^{15}$.

The compound listed above, wherein $R^{24}$ and $R^{25}$ are (C$_1$-C$_8$)alkyl.

A compound of the structure below:

where
    m is 0, 1, 2, 3, 4, 5, 6, 7, 8, 9 or 10;
    $R^2$ is selected from a group consisting of —H or —CH$_3$;
    $R^3$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where $R^7$ and $R^8$ are independently selected from H, (C$_1$-C$_8$)alkyl, or $R^7$ and $R^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or $R^3$ together with $R^4$ form a five- or six-membered carbocyclic or heterocyclic ring (e.g., piperidinyl);
    $R^4$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where $R^7$ and $R^8$ are independently selected from H, (C$_1$-C$_8$)alkyl, or $R^7$ and $R^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or $R^4$ together with $R^5$ form a five- or six-membered carbocyclic or heterocyclic ring (e.g., piperidinyl);
    $R^5$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where $R^7$ and $R^8$ are independently selected from H, (C$_1$-C$_8$)alkyl, or $R^7$ and $R^8$ together form a four-, five-, six-, or seven-membered heterocycle, (C$_1$-C$_8$)heteroalkyl, (C$_1$-C$_8$)substituted heteroalkyl, aryl, heteroaryl, substituted heteroaryl, or $R^5$ together with $R^6$ form a four-, five- or six-membered carbocyclic or heterocyclic ring (e.g., piperidinyl); or $R^4$, $R^5$ and $R^6$ together form fused carbocyclic or heterocyclic ring systems having five- or six-membered rings;

$R^6$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, ($C_1$-$C_8$)substituted alkyl, or $R^7$ and $R^8$ together form a four-, five-, six-, or seven-membered heterocycle, ($C_1$-$C_8$)heteroalkyl, ($C_1$-$C_8$)substituted heteroalkyl, aryl, substituted aryl, heteroaryl, substituted heteroaryl;

X is —OH, —$NH_2$, —SH, —$OR^{11}$, —$NHR^{12}$, —$NR^{13}R^{14}$, —$OC(O)R^{15}$, —$NHC(O)R^{16}$, —$SC(O)R^{17}$, —$C(O)OH$, —$C(O)OR^{18}$, —$C(O)NHR^{19}$, —$C(O)NR^{20}R^{21}$, —$N_3$;

$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from ($C_1$-$C_8$)alkyl, ($C_1$-$C_8$)substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —$P(O)(O—)$-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O) $(CH_2)_b$-[Nucleoside Triphosphate], where b is 1, 2, 3, 4, 5, 6, 7, 8, 9 or 10;

EWG is an electron withdrawing group;

$R^{22}$ and $R^{23}$ are independently selected from —$CH_3$, —$CH_2CH_3$, —$CH(CH_3)_2$ or $R^{22}$ and $R^{23}$ together form a heterocycle.

The compound listed above, wherein m is 0, 1, 2 or 3.

The compound listed above, wherein $R^3$ is —H or ($C_1$-$C_8$)alkyl.

The compound listed above, wherein X is —OH, —$OR^{11}$, or —$OC(O)R^{15}$.

A compound of the structure below:

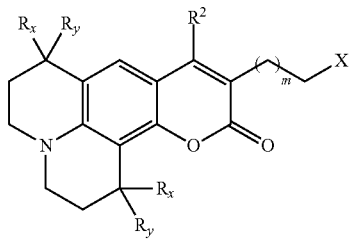

where m is 0, 1, 2, 3, 4, 5, 6, 7, 8, 9 or 10;

$R^2$ is selected from a group consisting of —H or —$CH_3$;

X is —OH, —$NH_2$, —SH, —$OR^{11}$, —$NHR^{12}$, —$NR^{13}R^{14}$, —$OC(O)R^{15}$, —$NHC(O)R^{16}$, —$SC(O)R^{17}$, —$C(O)OH$, —$C(O)OR^{18}$, —$C(O)NHR^{19}$, —$C(O)NR^{20}R^{21}$, —$N_3$;

$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from ($C_1$-$C_8$)alkyl, ($C_1$-$C_8$)substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —$P(O)(O—)$-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O) $(CH_2)_b$-[Nucleoside Triphosphate], where b is 1, 2, 3, 4, 5, 6, 7, 8, 9 or 10;

EWG is an electron withdrawing group;

$R_x$ and $R_y$ are independently H or $CH_3$;

$R^{22}$ and $R^{23}$ are independently selected from —$CH_3$, —$CH_2CH_3$, —$CH(CH_3)_2$ or $R^{22}$ and $R^{23}$ together form a heterocycle.

The compound listed above, wherein m is 0, 1, 2 or 3.

The compound listed above, wherein X is —OH, —$OR^{11}$, or —$OC(O)R^{15}$.

The compound of the structure below:

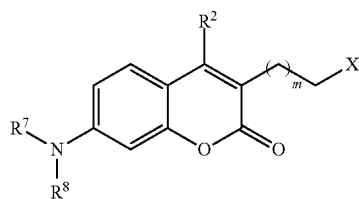

where m is 0, 1, 2, 3, 4, 5, 6, 7, 8, 9 or 10;

$R^2$ is selected from a group consisting of —H or —$CH_3$;

$R^7$ and $R^8$ are independently selected from H, ($C_1$-$C_8$) alkyl, ($C_1$-$C_8$)substituted alkyl, or $R^7$ and $R^8$ together form a five-, six-, or seven-membered heterocycle;

X is —OH, —$NH_2$, —SH, —$OR^{11}$, —$NHR^{12}$, —$NR^{13}R^{14}$, —$OC(O)R^{15}$, —$NHC(O)R^{16}$, —$SC(O)R^{17}$, —$C(O)OH$, —$C(O)OR^{18}$, —$C(O)NHR^{19}$, —$C(O)NR^{20}R^{21}$, —$N_3$;

$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from ($C_1$-$C_8$)alkyl, ($C_1$-$C_8$)substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —$P(O)(O—)$-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O) $(CH_2)_b$-[Nucleoside Triphosphate], where b is 1, 2, 3, 4, 5, 6, 7, 8, 9 or 10;

EWG is an electron withdrawing group;

$R^{22}$ and $R^{23}$ are independently selected from —$CH_3$, —$CH_2CH_3$, —$CH(CH_3)_2$ or $R^{22}$ and $R^{23}$ together form a heterocycle.

The compound listed above, wherein m is 0, 1, 2 or 3.

The compound listed above, wherein $R^7$ and $R^8$ are ($C_1$-$C_8$)alkyl.

The compound listed above, wherein X is —OH, —$OR^{11}$, or —$OC(O)R^{15}$.

A compound of the structure below:

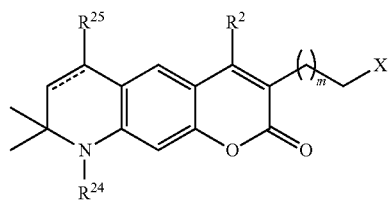

where
m is 0, 1, 2, 3, 4, 5, 6, 7, 8, 9 or 10;
$R^2$ is selected from a group consisting of —H or —$CH_3$;
the dashed line represents an optional double bond;
X is —OH, —$NH_2$, —SH, —$OR^{11}$, —$NHR^{12}$, —$NR^{13}R^{14}$, —$OC(O)R^{15}$, —$NHC(O)R^{16}$, —$SC(O)R^{17}$, —C(O)OH, —$C(O)OR^{18}$, —$C(O)NHR^{19}$, —$C(O)NR^{20}R^{21}$, —$N_3$;
$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from ($C_1$-$C_8$)alkyl, ($C_1$-$C_8$)substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —P(O)(O—)-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O)$(CH_2)_b$-[Nucleoside Triphosphate], where b is 1, 2, 3, 4, 5, 6, 7, 8, 9 or 10;
EWG is an electron withdrawing group;
$R^{22}$ and $R^{23}$ are independently selected from —$CH_3$, —$CH_2CH_3$, —$CH(CH_3)_2$ or $R^{22}$ and $R^{23}$ together form a heterocycle;
$R^{24}$ is ($C_1$-$C_8$)alkyl or ($C_1$-$C_8$)substituted alkyl;
$R^{25}$ is ($C_1$-$C_8$)alkyl, ($C_1$-$C_8$)substituted alkyl or $CH_2SO_3H$.

The compound listed above, wherein $R^{24}$ and $R^{25}$ are ($C_1$-$C_8$) substituted alkyl.

The compound listed above, wherein X is —OH, —$OR^{11}$, or —$OC(O)R^{15}$.

A compound of the structure below:

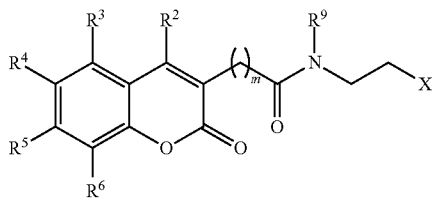

where
m is 0, 1, 2, 3, 4, 5, 6, 7, 8, 9 or 10;
$R^2$ is selected from a group consisting of —H or —$CH_3$;
$R^3$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl, or $R^3$ together with $R^4$ form a five- or six-membered carbocyclic or heterocyclic ring (e.g., piperidinyl);
$R^4$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl, or $R^4$ together with $R^5$ form a five- or six-membered carbocyclic or heterocyclic ring (e.g., piperidinyl);
$R^5$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl, or $R^5$ together with $R^6$ form a five- or six-membered carbocyclic or heterocyclic ring (e.g., piperidinyl); or $R^4$, $R^5$ and $R^6$ together form fused carbocyclic or heterocyclic ring systems having five- or six-membered rings;
$R^6$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, ($C_1$-$C_8$)substituted alkyl, or $R^7$ and $R^8$ together form a four-, five-, six-, or seven-membered heterocycle, ($C_1$-$C_8$)heteroalkyl, ($C_1$-$C_8$)substituted heteroalkyl, aryl, substituted aryl, heteroaryl, substituted heteroaryl;
$R^9$ is —H, —$CH_3$, —$CH_2CH_3$, —$CH(CH_3)_2$;
X is —OH, —$NH_2$, —SH, —$OR^{11}$, —$NHR^{12}$, —$NR^{13}R^{14}$, —$OC(O)R^{15}$, —$NHC(O)R^{16}$, —$SC(O)R^{17}$, —C(O)OH, —$C(O)OR^{18}$, —$C(O)NHR^{19}$, —$C(O)NR^{20}R^{21}$, —$N_3$;
$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from ($C_1$-$C_8$)alkyl, ($C_1$-$C_8$)substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —P(O)(O—)-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O)$(CH_2)_b$-[Nucleoside Triphosphate], where b is 1, 2, 3, 4, 5, 6, 7, 8, 9 or 10;
EWG is an electron withdrawing group;
$R^{22}$ and $R^{23}$ are independently selected from —$CH_3$, —$CH_2CH_3$, —$CH(CH_3)_2$ or $R^{22}$ and $R^{23}$ together form a heterocycle.

The compound listed above, wherein m is 0, 1, 2 or 3.

The compound listed above, wherein $R^3$ is —H or ($C_1$-$C_8$)alkyl.

The compound listed above, wherein X is —OH, —$OR^{11}$, or —$OC(O)R^{15}$.

A compound of the structure below:

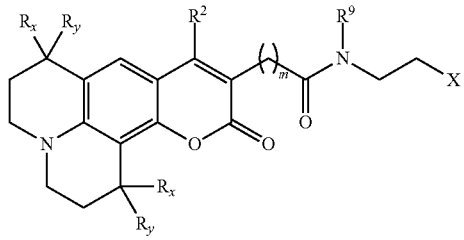

where
m is 0, 1, 2, 3, 4, 5, 6, 7, 8, 9 or 10;
$R^2$ is selected from a group consisting of —H or —$CH_3$;
$R^9$ is —H, —$CH_3$, —$CH_2CH_3$, —$CH(CH_3)_2$;
X is —OH, —$NH_2$, —SH, —$OR^{11}$, —$NHR^{12}$, —$NR^{13}R^{14}$, —$OC(O)R^{15}$, —$NHC(O)R^{16}$, —$SC(O)R^{17}$, —C(O)OH, —$C(O)OR^{18}$, —$C(O)NHR^{19}$, —$C(O)NR^{20}R^{21}$, —$N_3$;
$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from ($C_1$-$C_8$)alkyl, ($C_1$-$C_8$)substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —P(O)(O—)-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O)$(CH_2)_b$-[Nucleoside Triphosphate], where b is 1, 2, 3, 4, 5, 6, 7, 8, 9 or 10;
EWG is an electron withdrawing group;
$R_x$ and $R_y$ are independently H and $CH_3$;
$R^{22}$ and $R^{23}$ are independently selected from —$CH_3$, —$CH_2CH_3$, —$CH(CH_3)_2$ or $R^{22}$ and $R^{23}$ together form a heterocycle.

The compound listed above, wherein m is 0, 1, 2 or 3.
The compound listed above, wherein $R^9$ is —H or —$CH_3$.
The compound listed above, wherein X is —OH, —$OR^{11}$, or —$OC(O)R^{15}$.

A compound of the structure below:

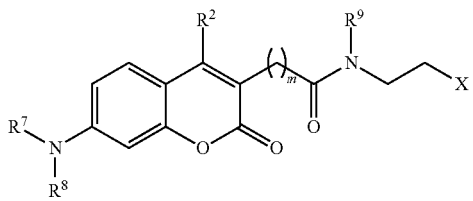

where
m is 0, 1, 2, 3, 4, 5, 6, 7, 8, 9 or 10;
$R^2$ is selected from a group consisting of —H or —$CH_3$;
$R^7$ and $R^8$ are independently selected from H, ($C_1$-$C_8$) alkyl, ($C_1$-$C_8$)substituted alkyl, or $R^7$ and $R^8$ together form a five-, six-, or seven-membered heterocycle;
$R^9$ is —H, —$CH_3$, —$CH_2CH_3$, —$CH(CH_3)_2$;
X is —OH, —$NH_2$, —SH, —$OR^{11}$, —$NHR^{12}$, —$NR^{13}R^{14}$, —$OC(O)R^{15}$, —$NHC(O)R^{16}$, —$SC(O)R^{17}$, —C(O)OH, —$C(O)OR^{18}$, —$C(O)NHR^{19}$, —$C(O)NR^{20}R^{21}$, —$N_3$;
$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from ($C_1$-$C_8$)alkyl, ($C_1$-$C_8$)substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —P(O)(O—)-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O)$(CH_2)_b$-[Nucleoside Triphosphate], where b is 1, 2, 3, 4, 5, 6, 7, 8, 9 or 10;
EWG is an electron withdrawing group;
$R^{22}$ and $R^{23}$ are independently selected from —$CH_3$, —$CH_2CH_3$, —$CH(CH_3)_2$ or $R^{22}$ and $R^{23}$ together form a heterocycle.

The compound listed above, wherein m is 0, 1, 2 or 3.
The compound listed above, wherein $R^9$ is —H or —$CH_3$.
The compound listed above, wherein X is —OH, —$OR^{11}$, or —$OC(O)R^{15}$.

A compound of the structure below:

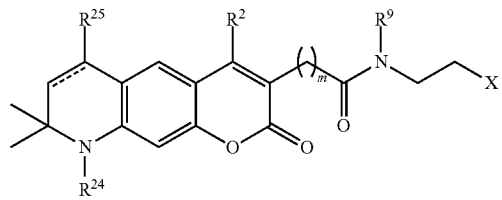

where
m is 0, 1, 2, 3, 4, 5, 6, 7, 8, 9 or 10;
$R^2$ is selected from a group consisting of —H or —$CH_3$;
$R^9$ is —H, —$CH_3$, —$CH_2CH_3$, —$CH(CH_3)_2$;
the dashed line represents an optional double bond;
X is —OH, —$NH_2$, —SH, —$OR^{11}$, —$NHR^{12}$, —$NR^{13}R^{14}$, —$OC(O)R^{15}$, —$NHC(O)R^{16}$, —$SC(O)R^{17}$, —C(O)OH, —$C(O)OR^{18}$, —$C(O)NHR^{19}$, —$C(O)NR^{20}R^{21}$, —$N_3$;
$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from ($C_1$-$C_8$)alkyl, ($C_1$-$C_8$)substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —P(O)(O—)-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O)$(CH_2)_b$-[Nucleoside Triphosphate], where b is 1, 2, 3, 4, 5, 6, 7, 8, 9 or 10;
EWG is an electron withdrawing group;
$R^{22}$ and $R^{23}$ are independently selected from —$CH_3$, —$CH_2CH_3$, —$CH(CH_3)_2$ or $R^{22}$ and $R^{23}$ together form a heterocycle;
$R^{24}$ is ($C_1$-$C_8$)alkyl or ($C_1$-$C_8$)substituted alkyl;
$R^{25}$ is ($C_1$-$C_8$)alkyl, ($C_1$-$C_8$)substituted alkyl or $CH_2SO_3H$.

The compound listed above, wherein m is 0, 1, 2, or 3.
The compound listed above, wherein $R^9$ is —H or —$CH_3$.
The compound listed above, wherein $R^{24}$ and $R^{25}$ are ($C_1$-$C_8$)alkyl.
The compound listed above, wherein X is —OH, —$OR^{11}$, or —$OC(O)R^{15}$.

A compound of the structure below:

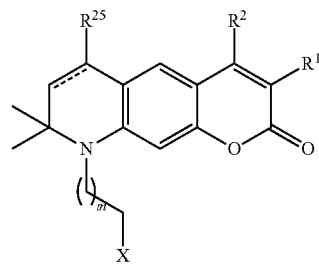

where
m is 0, 1, 2, 3, 4, 5, 6, 7, 8, 9 or 10;
$R^1$ is selected from a group consisting of —H or $CH_3$;
$R^2$ is selected from a group consisting of —H or —$CH_3$;
X is —OH, —$NH_2$, —SH, —$OR^{11}$, —$NHR^{12}$, —$NR^{13}R^{14}$, —$OC(O)R^{15}$, —$NHC(O)R^{16}$, —$SC(O)R^{17}$, —C(O)OH, —$C(O)OR^{18}$, —$C(O)NHR^{19}$, —$C(O)NR^{20}R^{21}$, —$N_3$;
$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from ($C_1$-$C_8$)alkyl, ($C_1$-$C_8$)substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —P(O)(O—)-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O)$(CH_2)_b$-[Nucleoside Triphosphate], where b is 1, 2, 3, 4, 5, 6, 7, 8, 9 or 10;
EWG is an electron withdrawing group;
$R^{22}$ and $R^{23}$ are independently selected from —$CH_3$, —$CH_2CH_3$, —$CH(CH_3)_2$ or $R^{22}$ and $R^{23}$ together form a heterocycle;
$R^{25}$ is ($C_1$-$C_8$)alkyl, ($C_1$-$C_8$)substituted alkyl or $CH_2SO_3H$.

The compound listed above, wherein m is 0, 1, 2 or 3.
The compound listed above, wherein $R^{25}$ is ($C_1$-$C_8$)alkyl.
The compound listed above, wherein X is —OH, —$OR^{11}$, or —$OC(O)R^{15}$.

A compound of the structure below:

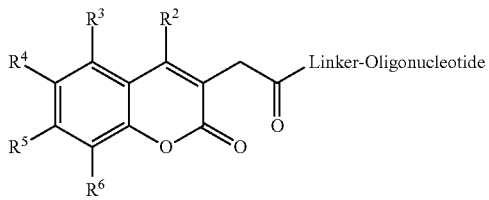

where
$R^2$ is selected from a group consisting of —H, —$CH_3$, —$(CH_2)_mC(O)NR^9R^{10}$ where m is 0, 1, 2, 3, 4, 5, 6, 7, 8, 9 or 10, and $R^9$ and $R^{10}$ are independently selected from —H, —$CH_2CCH$, —$(CH_2CH_2O)_oCH_2CCH$, —$CH_2N_3$, —$(CH_2CH_2O)_pCH_2N_3$, —$(CH_2)_xOH$, —$(CH_2CH_2O)_qCH_2CH_2OH$, where o is 1, 2, 3, 4, 5, 6, 7, 8, 9 or 10, p is 1, 2, 3, 4, 5, 6, 7, 8, 9 or 10, x is 2, 3, 4, 5, 6, 7, 8, 9, or 10 and q is 1, 2, 3, 4, 5, 6, 7, 8, 9 or 10, or $R^9$ and $R^{10}$ together form a five-, six- or seven-membered heterocycle (e.g., piperidinyl) substituted with a hydroxyl group;
$R^3$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl;
$R^4$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl;
$R^5$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl, or $R^4$, $R^5$ and $R^6$ together form fused ring systems having five- or six-membered rings;
$R^6$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl.

The compound listed above, wherein $R^2$ is —H or —$CH_3$.
The compound listed above, wherein $R^3$ is —H or —$CH_3$.
The compound listed above, wherein $R^4$ is —H or $R^4$, $R^5$ and $R^6$ together form fused ring systems having five- or six-membered rings.
The compound listed above, wherein $R^5$ is —$NR^7R^8$ or $R^4$, $R^5$ and $R^6$ together form fused ring systems having five- or six-membered rings.
The compound listed above, wherein $R^6$ is —H or $R^4$, $R^5$ and $R^6$ together form fused ring systems having five- or six-membered rings.

A compound of the structure below:

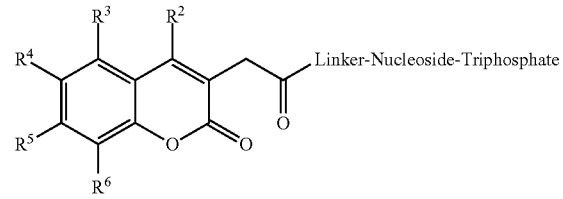

where
$R^2$ is selected from a group consisting of —H, —$CH_3$, —$(CH_2)_mC(O)NR^9R^{10}$ where m is 0, 1, 2, 3, 4, 5, 6, 7, 8, 9 or 10, and $R^9$ and $R^{10}$ are independently selected from —H, —$CH_2CCH$, —$(CH_2CH_2O)_oCH_2CCH$, —$CH_2N_3$, —$(CH_2CH_2O)_pCH_2N_3$, —$(CH_2)_xOH$, —$(CH_2CH_2O)_qCH_2CH_2OH$, where o is 1, 2, 3, 4, 5, 6, 7, 8, 9 or 10, p is 1, 2, 3, 4, 5, 6, 7, 8, 9 or 10, x is 2, 3, 4, 5, 6, 7, 8, 9, or 10 and q is 1, 2, 3, 4, 5, 6, 7, 8, 9 or 10, or $R^9$ and $R^{10}$ together form a five-, six- or seven-membered heterocycle (e.g., piperidinyl) substituted with a hydroxyl group;
$R^3$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl;

$R^4$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl;

$R^5$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or R$^4$, R$^5$ and R$^6$ together form fused ring systems having five- or six-membered rings;

$R^6$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl.

The compound listed above, wherein R$^2$ is —H or —CH$_3$.

The compound listed above, wherein R$^4$ is —H or R$^4$, R$^5$ and R$^6$ together form fused ring systems having five- or six-membered rings.

The compound listed above, wherein R$^5$ is —NR$^7$R$^8$ or R$^4$, R$^5$ and R$^6$ together form fused ring systems having five- or six-membered rings.

The compound listed above, wherein R$^6$ is —H or R$^4$, R$^5$ and R$^6$ together form fused ring systems having five- or six-membered rings.

A method of making an oligonucleotide probe comprising a coumarin moiety, wherein the method comprises the steps of:

1) synthesizing an oligonucleotide using a solid phase synthesis method to provide a solid support bound oligonucleotide;

2) reacting the solid support bound oligonucleotide with a coumarin compound comprising a phosphoramidite moiety to provide a solid support bound oligonucleotide probe comprising a coumarin moiety;

3) removing the probe from the solid support at a temperature between 50° C. and 70° C., in concentrated ammonia, for a period of 2 h to 8 h;

4) isolating the probe wherein the coumarin moiety of the isolated probe is degraded to an extent less than 5.0 percent.

The method listed above, wherein the coumarin moiety of the isolated probe is degraded to an extent less than 2.5 percent.

The method listed above, wherein the coumarin compound comprising a phosphoramidite moiety is of the following structure:

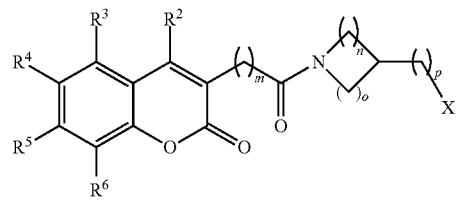

wherein m is 1, 2, 3, 4 or 5;

n is 1, 2 or 3;

o is 1, 2 or 3;

p is 0, 1, 2, 3, 4, 5, 7, 8, 9 or 10;

$R^2$ is selected from a group consisting of —H, —CH$_3$, —(CH$_2$)$_m$C(O)NR$^9$R$^{10}$ where m is 0, 1, 2, 3, 4, 5, 6, 7, 8, 9 or 10, and R$^9$ and R$^{10}$ are independently selected from —H, —CH$_2$CCH, —(CH$_2$CH$_2$O)$_o$CH$_2$CCH, —CH$_2$N$_3$, —(CH$_2$CH$_2$O)$_p$CH$_2$N$_3$, —(CH$_2$)$_x$OH, —(CH$_2$CH$_2$O)$_q$CH$_2$CH$_2$OH, where o is 1, 2, 3, 4, 5, 6, 7, 8, 9 or 10, p is 1, 2, 3, 4, 5, 6, 7, 8, 9 or 10, x is 2, 3, 4, 5, 6, 7, 8, 9, or 10 and q is 1, 2, 3, 4, 5, 6, 7, 8, 9 or 10, or R$^9$ and R$^{10}$ together form a five-, six- or seven-membered heterocycle (e.g., piperidinyl) substituted with a hydroxyl group;

$R^3$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl;

$R^4$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl;

$R^5$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or R$^4$, R$^5$ and R$^6$ together form fused ring systems having five- or six-membered rings;

$R^6$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl;

X is —O—P(NR$^{22}$R$^{23}$)OCH$_2$CH$_2$-EWG or (CH$_2$CH$_2$O)$_a$—CH$_2$CH$_2$OP(NR$^{22}$R$^{23}$)OCH$_2$CH$_2$-EWG, wherein a is 0, 1, 2, 3, 4, 5, 6, 7, 8, 9 or 10;

EWG is an electron withdrawing group;

R$^{22}$ and R$_{23}$ are independently selected from —CH$_3$, —CH$_2$CH$_3$, —CH(CH$_3$)$_2$ or R$^{22}$ and R$^{23}$ together form a heterocycle.

The method listed above, wherein the coumarin compound comprising a phosphoramidite moiety is of the following structure:

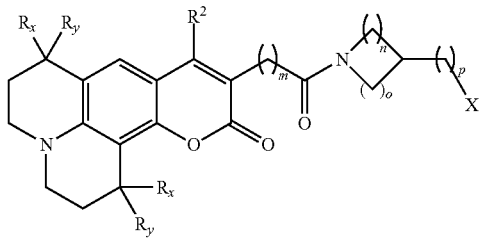

wherein m is 1, 2, 3, 4 or 5;
n is 1, 2 or 3;
o is 1, 2 or 3;
p is 0, 1, 2, 3, 4, 5, 6, 7, 8, 9 or 10;
R$^2$ is —H or —CH$_3$;
X is —O—P(NR$^{22}$R$^{23}$)OCH$_2$CH$_2$-EWG or (CH$_2$CH$_2$O)$_a$—CH$_2$CH$_2$OP(NR$^{22}$R$^{23}$)OCH$_2$CH$_2$-EWG, wherein a is 0, 1, 2, 3, 4, 5, 6, 7, 8, 9 or 10;
EWG is an electron withdrawing group;
R$_x$ and R$_y$ are independently H or CH$_3$;
R$^{22}$ and R$^{23}$ are independently selected from —CH$_3$, —CH$_2$CH$_3$, —CH(CH$_3$)$_2$ or R$^{22}$ and R$^{23}$ together form a heterocycle.

The method listed above, wherein the coumarin compound comprising a phosphoramidite moiety is of the following structure:

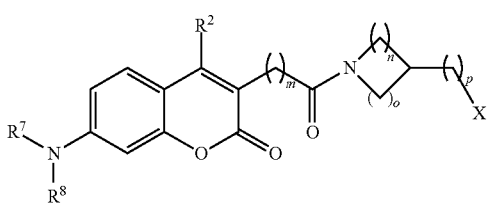

wherein m is 1, 2, 3, 4 or 5;
n is 1, 2 or 3;
o is 1, 2 or 3;
p is 0, 1, 2, 3, 4, 5, 6, 7, 8, 9 or 10;
R$^2$ is —H or —CH$_3$;
X is —O—P(NR$^{22}$R$^{23}$)OCH$_2$CH$_2$-EWG or (CH$_2$CH$_2$O)$_a$—CH$_2$CH$_2$OP(NR$^{22}$R$^{23}$)OCH$_2$CH$_2$-EWG, wherein a is 0, 1, 2, 3, 4, 5, 6, 7, 8, 9 or 10;
EWG is an electron withdrawing group;
R$^7$ and R$^8$ are independently selected from H, (C$_1$-C$_8$)alkyl, (C$_1$-C$_8$)substituted alkyl, or R$^7$ and R$^8$ together form a five-, six-, or seven-membered heterocycle;
R$^{22}$ and R$^{23}$ are independently selected from —CH$_3$, —CH$_2$CH$_3$, —CH(CH$_3$)$_2$ or R$^{22}$ and R$^{23}$ together form a heterocycle.

The method listed above, wherein the coumarin compound comprising a phosphoramidite moiety is of the following structure:

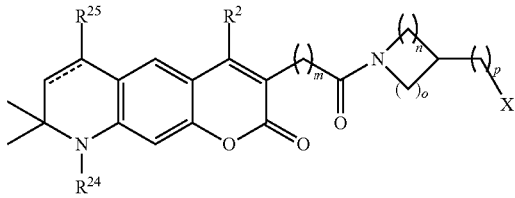

wherein m is 1, 2, 3, 4 or 5;
n is 1, 2 or 3;
o is 1, 2 or 3;
p is 0, 1, 2, 3, 4, 5, 6, 7, 8, 9 or 10;
R$^2$ is —H or —CH$_3$;
X is —O—P(NR$^{22}$R$^{23}$)OCH$_2$CH$_2$-EWG or (CH$_2$CH$_2$O)$_a$—CH$_2$CH$_2$OP(NR$^{22}$R$^{23}$)OCH$_2$CH$_2$-EWG, wherein a is 0, 1, 2, 3, 4, 5, 6, 7, 8, 9 or 10;
EWG is an electron withdrawing group;
R$^{22}$ and R$^{23}$ are independently selected from —CH$_3$, —CH$_2$CH$_3$, —CH(CH$_3$)$_2$ or R$^{22}$ and R$^{23}$ together form a heterocycle;
R$^{24}$ is (C$_1$-C$_8$)alkyl or (C$_1$-C$_8$)substituted alkyl;
R$^{25}$ is (C$_1$-C$_8$)alkyl, (C$_1$-C$_8$)substituted alkyl or CH$_2$SO$_3$H.

A coumarin-CPG compound of the following structure:

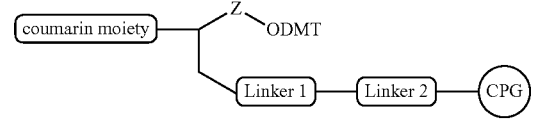

wherein the coumarin moiety is of the structure

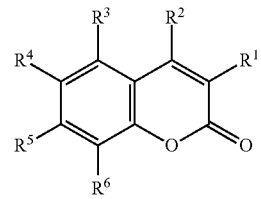

R$^1$ is selected from a group consisting of —H, —CH$_3$, —(CH$_2$)$_m$C(O)NR$^9$R$^{10}$ where m is 0, 1, 2, 3, 4, 5, 6, 7, 8, 9 or 10, and R$^9$ and R$^{10}$ are independently selected from a radical, —H, —CH$_2$CCH, —(CH$_2$CH$_2$O)$_o$CH$_2$CCH, —CH$_2$N$_3$, —(CH$_2$CH$_2$O)$_p$CH$_2$N$_3$, —(CH$_2$)$_x$OH, —(CH$_2$CH$_2$O)$_q$CH$_2$CH$_2$OH, where o is 1, 2, 3, 4, 5, 6, 7, 8, 9 or 10, p is 1, 2, 3, 4, 5, 6, 7, 8, 9 or 10, x is 2, 3, 4, 5, 6, 7, 8, 9, or 10 and q is 1, 2, 3, 4, 5, 6, 7, 8, 9 or 10, or R$^9$ and R$^{10}$ together form a five-, six- or seven-membered heterocycle (e.g., piperidinyl) substituted with a hydroxyl group;

R$^2$ is selected from a group consisting of —H, —CH$_3$, —(CH$_2$)$_m$C(O)NR$^9$R$^{10}$ where m is 0, 1, 2, 3, 4, 5, 6, 7, 8, 9 or 10, and R$^9$ and R$^{10}$ are independently selected from a radical, —H, —CH$_2$CCH, —(CH$_2$CH$_2$O)$_o$CH$_2$CCH, —CH$_2$N$_3$, —(CH$_2$CH$_2$O)$_p$CH$_2$N$_3$, —(CH$_2$)$_x$OH, —(CH$_2$CH$_2$O)$_q$CH$_2$CH$_2$OH, where o is 1, 2, 3, 4, 5, 6, 7, 8, 9 or 10, p is 1, 2, 3, 4, 5, 6, 7, 8, 9 or 10, x is 2, 3, 4, 5, 6, 7, 8, 9, or 10 and q is 1, 2, 3, 4, 5, 6, 7, 8, 9 or 10, or R$^9$ and R$^{10}$ together form a five-, six- or seven-membered heterocycle (e.g., piperidinyl) substituted with a hydroxyl group;

$R^3$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl;

$R^4$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl;

$R^5$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl, or $R^4$, $R^5$ and $R^6$ together form fused ring systems having five- or six-membered rings;

$R^6$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl;

wherein the coumarin moiety is attached to the coumarin-CPG compound through either $R^1$ or $R^2$;

wherein Z is $(CH_2)_x$, wherein x is 1, 2, 3, 4, 5, 6, 7, 8, 9 or 10;

wherein Linker 1 is selected from $OC(O)(CH_2)_y$, $O(CH_2)_z(CO)$,
$NHC(O)(CH_2)_yO(CH_2)_z(CO)$, wherein y is 1, 2, 3, 4, 5, 6, 7, 8, 9 or 10, and wherein z is 1, 2, 3, 4, 5, 6, 7, 8, 9 or 10;

wherein Linker 2 is selected from $NH(CH_2)_a$ and $O(CH_2)_a$, wherein a is 1, 2, 3, 4, 5, 6, 7, 8, 9 or 10.

The coumarin-CPG compound listed above, wherein the coumarin moiety is of the structure

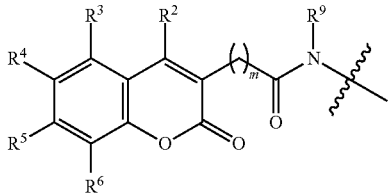

m is 0, 1, 2, 3, 4, 5, 6, 7, 8, 9 or 10;
$R^2$ is H or $CH_3$;
$R^3$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl;

$R^4$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl;

$R^5$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl, or $R^4$, $R^5$ and $R^6$ together form fused ring systems having five- or six-membered rings;

$R^6$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl;

$R^9$ is H, $CH_3$, $CH_2CH_3$ or $CH(CH_3)_2$.

The coumarin-CPG compound listed above, wherein the coumarin moiety is of the structure

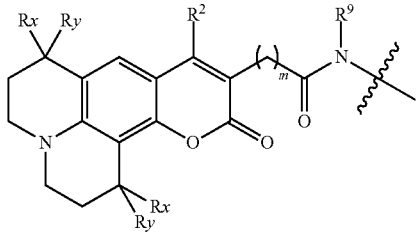

m is 0, 1, 2, 3, 4, 5, 6, 7, 8, 9 or 10;
$R^2$ is H or $CH_3$;
$R_x$ and $R_y$ and independently H or $CH_3$;
$R^9$ is H, $CH_3$, $CH_2CH_3$ or $CH(CH_3)_2$.

The coumarin-CPG compound listed above, wherein the coumarin moiety is of the structure

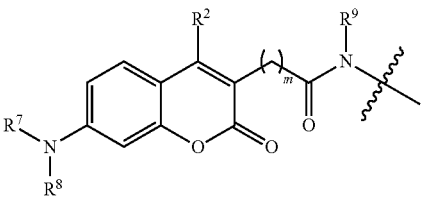

m is 0, 1, 2, 3, 4, 5, 6, 7, 8, 9 or 10;

$R^2$ is H or $CH_3$;

$R^7$ and $R^8$ are independently selected from H, ($C_1$-$C_8$) alkyl, ($C_1$-$C_8$)substituted alkyl, or $R^7$ and $R^8$ together form a four-, five-, six-, or seven-membered heterocycle;

$R^9$ is H, $CH_3$, $CH_2CH_3$ or $CH(CH_3)_2$.

The coumarin-CPG compound listed above, wherein the coumarin moiety is of the structure

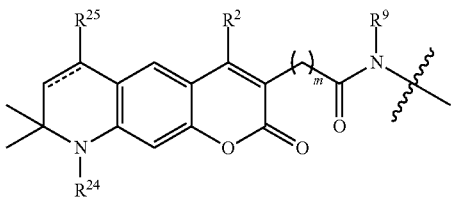

m is 0, 1, 2, 3, 4, 5, 6, 7, 8, 9 or 10;

$R^2$ is H or $CH_3$;

$R^9$ is H, $CH_3$, $CH_2CH_3$ or $CH(CH_3)_2$;

$R^{24}$ is ($C_1$-$C_8$)alkyl or ($C_1$-$C_8$)substituted alkyl;

$R^{25}$ is ($C_1$-$C_8$)alkyl, ($C_1$-$C_8$)substituted alkyl or $CH_2SO_3H$.

A method of making a coumarin-CPG compound, wherein the method comprises the following steps:

a) preparing a first coumarin-based compound of the structure

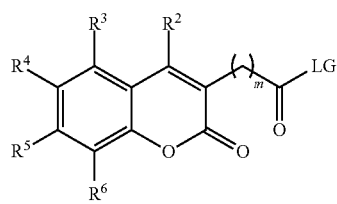

wherein m is 0, 1, 2, 3, 4, 5, 6, 7, 8, 9 or 10;

$R^2$ is H or $CH_3$;

LG is a leaving group;

$R^3$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl;

$R^4$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from —H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl;

$R^5$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl, or $R^4$, $R^5$ and $R^6$ together form fused ring systems having five- or six-membered rings;

$R^6$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl;

b) reacting the first coumarin-based compound with an amine of the structure

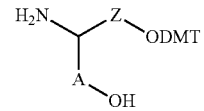

wherein Z is $(CH_2)_x$, wherein x is 1, 2, 3, 4, 5, 6, 7, 8, 9 or 10;

A is $(CH_2)_y$, wherein y is 1, 2, 3, 4, 5, 6, 7, 8, 9 or 10;

to provide a second coumarin-based compound of the structure

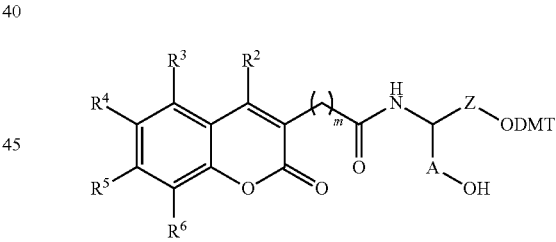

c) reacting the second coumarin-based compound with a first linker group of the structure

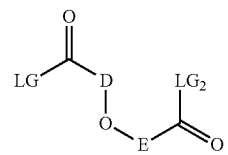

wherein LG is a first leaving group, $LG_2$ is a second leaving group, D is $(CH_2)x$ where x is 1, 2, 3, 4, 5, 6, 7, 8, 9 or 10, E is $(CH_2)y$ where y is 1, 2, 3, 4, 5, 6, 7, 8, 9 or 10;

to provide a third coumarin-based compound of the structure

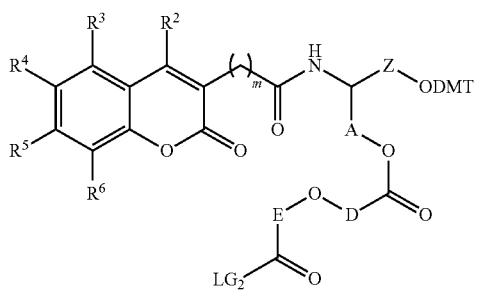

d) reacting the third coumarin-based structure with CPG functionalized with a nucleophile

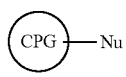

to provide the coumarin-CPG compound.

The method of making a coumarin-CPG compound listed above, wherein the first coumarin-based compound is of the structure

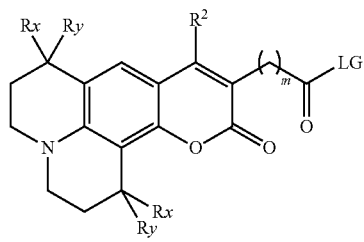

LG is a leaving group;
m is 0, 1, 2, 3, 4, 5, 6, 7, 8, 9 or 10;
$R^2$ is H or $CH_3$;
$R_x$ and $R_y$ and independently H or $CH_3$.

The method of making a coumarin-CPG compound listed above, wherein the first coumarin-based compound is of the structure

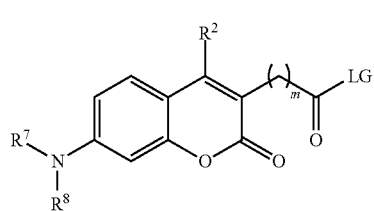

LG is a leaving group;
m is 0, 1, 2, 3, 4, 5, 6, 7, 8, 9 or 10;
$R^2$ is H or $CH_3$;
$R^7$ and $R^8$ are independently selected from H, $(C_1-C_8)$ alkyl, $(C_1-C_8)$substituted alkyl, or $R^7$ and $R^8$ together form a four-, five-, six-, or seven-membered heterocycle.

The method of making a coumarin-CPG compound listed above, wherein the first coumarin-based compound is of the structure

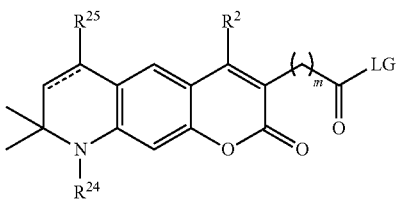

m is 0, 1, 2, 3, 4, 5, 6, 7, 8, 9 or 10;
LG is a leaving group;
$R^2$ is H or $CH_3$;
$R^{24}$ is $(C_1-C_8)$alkyl or $(C_1-C_8)$substituted alkyl;
$R^{25}$ is $(C_1-C_8)$alkyl, $(C_1-C_8)$substituted alkyl or $CH_2SO_3H$.

DETAILED DESCRIPTION OF THE INVENTION

Unless otherwise stated, the following terms used in the specification and claims have the meanings given below:
Definitions Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well-known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and synthetic organic chemistry described below are those well-known and commonly employed in the art. Standard techniques, or modifications thereof, are used for chemical syntheses and chemical analyses.

"Analyte", as used herein means any compound or molecule of interest for which a diagnostic test is performed. An analyte can be, for example, a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc., without limitation.

As used herein, "energy transfer" refers to the process by which the excited state energy of an excited group is altered by a modifying group, such as a quencher. If the excited state energy-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena.

As used herein, "energy transfer pair" refers to any two molecules that participate in energy transfer. Typically, one of the molecules acts as a fluorescent group, and the other acts as a fluorescence-modifying group. The preferred energy transfer pair of the instant invention comprises a fluorescent group and a quenching group of the invention. There is no limitation on the identity of the individual members of the energy transfer pair in this application. All that is required is that the spectroscopic properties of the energy transfer pair as a whole change in some measurable way if the distance between the individual members is altered by some critical amount. "Energy transfer pair" is used to refer to a group of molecules that form a complex within which energy transfer occurs. Such complexes may include, for example, two fluorescent groups, which may be different from one another and one quenching group, two quenching groups and one fluorescent group, or multiple fluorescent groups and multiple quenching groups. In cases where there are multiple fluorescent groups and/or multiple quenching groups, the individual groups may be different from one another.

As used herein, "fluorescence-modifying group" refers to a molecule of the invention that can alter in any way the fluorescence emission from a fluorescent group. A fluorescence-modifying group generally accomplishes this through an energy transfer mechanism. Depending on the identity of the fluorescence-modifying group, the fluorescence emission can undergo a number of alterations, including, but not limited to, attenuation, complete quenching, enhancement, a shift in wavelength, a shift in polarity, and a change in fluorescence lifetime. One example of a fluorescence-modifying group is a quenching group.

As used herein, "quenching group" refers to any fluorescence-modifying group of the invention that can attenuate at least partly the light emitted by a fluorescent group. This attenuation is referred to herein as "quenching". Hence, illumination of the fluorescent group in the presence of the quenching group leads to an emission signal that is less intense than expected, or even completely absent. Quenching typically occurs through energy transfer between the fluorescent group and the quenching group.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a BHQ, a fluorophore or another moiety.

"Peptide" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

"Bioactive species," refers to molecules that, when administered to an organism, affect that organism. Exemplary bioactive species include pharmaceuticals, pesticides, herbicides, growth regulators and the like. Bioactive species encompasses small molecules (i.e., approximately <1000 daltons), oligomers, polymers and the like. Also included are nucleic acids and their analogues, peptides and their analogues and the like.

The term "alkyl" is used herein to refer to a branched or unbranched, saturated or unsaturated, monovalent and divalent hydrocarbon radical, generally having from about 1-30 carbons and preferably, from 4-20 carbons and more preferably from 6-18 carbons. When the alkyl group has from 1-6 carbon atoms, it is referred to as a "lower alkyl." Suitable alkyl radicals include, for example, structures containing one or more methylene, methine and/or methyne groups. Branched structures have a branching motif similar to i-propyl, t-butyl, i-butyl, 2-ethylpropyl, etc. As used herein, the term encompasses "substituted alkyls," and "cyclic alkyl." The term $(C_1-C_8)$alkyl refers to an alkyl that has between one and eight carbon atoms.

"Substituted alkyl" refers to alkyl as just described including one or more substituents such as, for example, lower alkyl, aryl, acyl, halogen (i.e., alkylhalos, e.g., $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl moiety. Additionally, these groups may be pendent from, or integral to, the alkyl chain.

The term "aryl" is used herein to refer to an aromatic substituent, which may be a single aromatic ring or multiple aromatic rings which are fused together, linked covalently, or linked to a common group such as a diazo, methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl" and "substituted aryl."

"Substituted aryl" refers to aryl as just described including one or more functional groups such as lower alkyl, acyl, halogen, alkylhalos (e.g. $CF_3$), hydroxy, amino, alkoxy, alkylamino, acylamino, acyloxy, phenoxy, mercapto and both saturated and unsaturated cyclic hydrocarbons which are fused to the aromatic ring(s), linked covalently or linked to a common group such as a diazo, methylene or ethylene moiety. The linking group may also be a carbonyl such as in cyclohexyl phenyl ketone. The term "substituted aryl" encompasses "substituted arylalkyl."

The term "arylalkyl" is used herein to refer to a subset of "aryl" in which the aryl group is attached to another group by an alkyl group as defined herein.

"Substituted arylalkyl" defines a subset of "substituted aryl" wherein the substituted aryl group is attached to another group by an alkyl group as defined herein.

The term "acyl" is used to describe a ketone substituent, C(O)R, where R is alkyl or substituted alkyl, aryl or substituted aryl as defined herein.

The term "halogen" is used herein to refer to fluorine, bromine, chlorine and iodine atoms.

The term "hydroxy" is used herein to refer to the group —OH.

The term "amino" is used to —NRR', wherein R and R' are independently H, alkyl, aryl or substituted analogues thereof "Amino" encompasses "alkylamino" denoting secondary and tertiary amines and "acylamino" describing the group RC(O)NR'.

The term "alkoxy" is used herein to refer to the —OR group, where R is alkyl, or a substituted analogue thereof. Suitable alkoxy radicals include, for example, methoxy, ethoxy, t-butoxy, etc.

As used herein, the term "aryloxy" denotes aromatic groups that are linked to another group directly through an oxygen atom. This term encompasses "substituted aryloxy" moieties in which the aromatic group is substituted as described above for "substituted aryl." Exemplary aryloxy moieties include phenoxy, substituted phenoxy, benzyloxy, phenethyloxy, etc.

As used herein "aryloxyalkyl" defines aromatic groups attached, through an oxygen atom to an alkyl group, as defined herein. The term "aryloxyalkyl" encompasses "substituted aryloxyalkyl" moieties in which the aromatic group is substituted as described for "substituted aryl."

As used herein, the term "mercapto" defines moieties of the general structure —S—R wherein R is H, alkyl, aryl or heterocyclic as described herein.

The term "saturated cyclic hydrocarbon" denotes groups such as the cyclopropyl, cyclobutyl, cyclopentyl, etc., and substituted analogues of these structures. These cyclic hydrocarbons can be single- or multi-ring structures.

The term "unsaturated cyclic hydrocarbon" is used to describe a monovalent non-aromatic group with at least one double bond, such as cyclopentene, cyclohexene, etc. and substituted analogues thereof. These cyclic hydrocarbons can be single- or multi-ring structures.

The term "heteroaryl" as used herein refers to aromatic rings in which one or more carbon atoms of the aromatic ring(s) are replaced by a heteroatom such as nitrogen, oxygen or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as a diazo, methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" defines a subset of "heteroaryl" wherein an alkyl group, as defined herein, links the heteroaryl group to another group.

"Substituted heteroaryl" refers to heteroaryl as just described wherein the heteroaryl nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

"Substituted heteroarylalkyl" refers to a subset of "substituted heteroaryl" as described above in which an alkyl group, as defined herein, links the heteroaryl group to another group.

The term "heterocyclic" is used herein to describe a monovalent saturated or unsaturated non-aromatic group having a single ring or multiple condensed rings from 1-12 carbon atoms and from 1-4 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, alkylhalos (e.g., $CF_3$), hydroxy, amino, alkoxy, alkylamino, acylamino, acyloxy, mercapto, etc.

The term "heterocyclicalkyl" defines a subset of "heterocyclic" wherein an alkyl group, as defined herein, links the heterocyclic group to another group Compounds In one aspect, the present invention is directed to compounds. One set of compounds is represented by Structure 13, below:

Structure 13

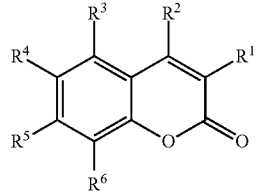

where $R^1$ is selected from a group consisting of —H, —$CH_3$, —$(CH_2)_mC(O)NR^9R^{10}$ where m is 0, 1, 2, 3, 4, 5, 6, 7, 8, 9 or 10, and $R^9$ and $R^{10}$ are independently selected from —H, —$CH_2CCH$, —$(CH_2CH_2O)_oCH_2CCH$, —$CH_2N_3$, —$(CH_2CH_2O)_pCH_2N_3$, —$(CH_2)_xOH$, —$(CH_2CH_2O)_qCH_2CH_2OH$, where o is 1, 2, 3, 4, 5, 6, 7, 8, 9 or 10, p is 1, 2, 3, 4, 5, 6, 7, 8, 9 or 10, x is 2, 3, 4, 5, 6, 7, 8, 9, or 10 and q is 1, 2, 3, 4, 5, 6, 7, 8, 9 or 10, or $R^9$ and $R^{10}$ together form a five-, six- or seven-membered heterocycle (e.g., piperidinyl) substituted with a hydroxyl group;

$R^2$ is selected from a group consisting of —H, —$CH_3$, —$(CH_2)_mC(O)NR^9R^{10}$ where m is 0, 1, 2, 3, 4, 5, 6, 7, 8, 9 or 10, and $R^9$ and $R^{10}$ are independently selected from —H, —$CH_2CCH$, —$(CH_2CH_2O)_oCH_2CCH$, —$CH_2N_3$, —$(CH_2CH_2O)_pCH_2N_3$, —$(CH_2)_xOH$, —$(CH_2CH_2O)_qCH_2CH_2OH$, where o is 1, 2, 3, 4, 5, 6, 7, 8, 9 or 10, p is 1, 2, 3, 4, 5, 6, 7, 8, 9 or 10, x is 2, 3, 4, 5, 6, 7, 8, 9, or 10 and q is 1, 2, 3, 4, 5, 6, 7, 8, 9 or 10, or $R^9$ and $R^{10}$ together form a five-, six- or seven-membered heterocycle (e.g., piperidinyl) substituted with a hydroxyl group;

$R^3$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl;

$R^4$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$)

heteroalkyl, $(C_1\text{-}C_8)$substituted heteroalkyl, aryl, substituted aryl, heteroaryl, substituted heteroaryl;

$R^5$ is selected from a group consisting of —H, -halogen, —$CF_3$, —OH, —$NH_2$, —CCH, —CN, —$NO_2$, $(C_1\text{-}C_8)$ alkyl, $(C_1\text{-}C_8)$substituted alkyl, $(C_1\text{-}C_8)$alkylthio, $(C_1\text{-}C_8)$ substituted alkylthio, $(C_1\text{-}C_8)$alkoxy, $(C_1\text{-}C_8)$substituted alkoxy, —$NR^7R^8$ where $R^7$ and $R^8$ are independently selected from H, $(C_1\text{-}C_8)$alkyl, or $R^7$ and $R^8$ together form a four-, five-, six-, or seven-membered heterocycle, $(C_1\text{-}C_8)$ heteroalkyl, $(C_1\text{-}C_8)$substituted heteroalkyl, aryl, substituted aryl, heteroaryl, substituted heteroaryl, or $R^4$, $R^5$ and $R^6$ together form fused ring systems having five- or six-membered rings;

$R^6$ is selected from a group consisting of —H, -halogen, —$CF_3$, —OH, —$NH_2$, —CCH, —CN, —$NO_2$, $(C_1\text{-}C_8)$ alkyl, $(C_1\text{-}C_8)$substituted alkyl, $(C_1\text{-}C_8)$alkylthio, $(C_1\text{-}C_8)$ substituted alkylthio, $(C_1\text{-}C_8)$alkoxy, $(C_1\text{-}C_8)$substituted alkoxy, —$NR^7R^8$ where $R^7$ and $R^8$ are independently selected from H, $(C_1\text{-}C_8)$alkyl, or $R^7$ and $R^8$ together form a four-, five-, six-, or seven-membered heterocycle, $(C_1\text{-}C_8)$ heteroalkyl, $(C_1\text{-}C_8)$substituted heteroalkyl, aryl, substituted aryl, heteroaryl, substituted heteroaryl.

Another set of compounds is represented by Structure 14, below:

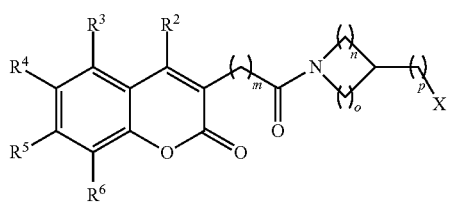

Structure 14 where
m is 0, 1, 2, 3, 4, 5, 6, 7, 8, 9 or 10;
n is 0, 1, 2 or 3;
o is 0, 1, 2 or 3;
p is 0, 1, 2, 3, 4, 5, 6, 7, 8, 9 or 10;
$R^2$ is selected from a group consisting of —H or —$CH_3$;
$R^3$ is selected from a group consisting of —H, -halogen, —$CF_3$, —OH, —$NH_2$, —CCH, —CN, —$NO_2$, $(C_1\text{-}C_8)$ alkyl, $(C_1\text{-}C_8)$substituted alkyl, $(C_1\text{-}C_8)$alkylthio, $(C_1\text{-}C_8)$ substituted alkylthio, $(C_1\text{-}C_8)$alkoxy, $(C_1\text{-}C_8)$substituted alkoxy, —$NR^7R^8$ where $R^7$ and $R^8$ are independently selected from H, $(C_1\text{-}C_8)$alkyl, or $R^7$ and $R^8$ together form a four-, five-, six-, or seven-membered heterocycle, $(C_1\text{-}C_8)$ heteroalkyl, $(C_1\text{-}C_8)$substituted heteroalkyl, aryl, substituted aryl, heteroaryl, substituted heteroaryl, or $R^3$ together with $R^4$ form a five- or six-membered carbocyclic or heterocyclic ring (e.g., piperidinyl);

$R^4$ is selected from a group consisting of —H, -halogen, —$CF_3$, —OH, —$NH_2$, —CCH, —CN, —$NO_2$, $(C_1\text{-}C_8)$ alkyl, $(C_1\text{-}C_8)$substituted alkyl, $(C_1\text{-}C_8)$alkylthio, $(C_1\text{-}C_8)$ substituted alkylthio, $(C_1\text{-}C_8)$alkoxy, $(C_1\text{-}C_8)$substituted alkoxy, —$NR^7R^8$ where $R^7$ and $R^8$ are independently selected from H, $(C_1\text{-}C_8)$alkyl, or $R^7$ and $R^8$ together form a four-, five-, six-, or seven-membered heterocycle, $(C_1\text{-}C_8)$ heteroalkyl, $(C_1\text{-}C_8)$substituted heteroalkyl, aryl, substituted aryl, heteroaryl, substituted heteroaryl, or $R^4$ together with $R^5$ form a five- or six-membered carbocyclic or heterocyclic ring (e.g., piperidinyl);

$R^5$ is selected from a group consisting of —H, -halogen, —$CF_3$, —OH, —$NH_2$, —CCH, —CN, —$NO_2$, $(C_1\text{-}C_8)$ alkyl, $(C_1\text{-}C_8)$substituted alkyl, $(C_1\text{-}C_8)$alkylthio, $(C_1\text{-}C_8)$ substituted alkylthio, $(C_1\text{-}C_8)$alkoxy, $(C_1\text{-}C_8)$substituted alkoxy, —$NR^7R^8$ where $R^7$ and $R^8$ are independently selected from H, $(C_1\text{-}C_8)$alkyl, or $R^7$ and $R^8$ together form a four-, five-, six-, or seven-membered heterocycle, $(C_1\text{-}C_8)$ heteroalkyl, $(C_1\text{-}C_8)$substituted heteroalkyl, aryl, substituted aryl, heteroaryl, substituted heteroaryl, or $R^5$ together with $R^6$ form a five- or six-membered carbocyclic or heterocyclic ring (e.g., piperidinyl); or $R^4$, $R^5$ and $R^6$ together form fused carbocyclic or heterocyclic ring systems having five- or six-membered rings;

$R^6$ is selected from a group consisting of —H, -halogen, —$CF_3$, —OH, —$NH_2$, —CCH, —CN, —$NO_2$, $(C_1\text{-}C_8)$ alkyl, $(C_1\text{-}C_8)$substituted alkyl, $(C_1\text{-}C_8)$alkylthio, $(C_1\text{-}C_8)$ substituted alkylthio, $(C_1\text{-}C_8)$alkoxy, $(C_1\text{-}C_8)$substituted alkoxy, —$NR^7R^8$ where $R^7$ and $R^8$ are independently selected from H, $(C_1\text{-}C_8)$alkyl, $(C_1\text{-}C_8)$substituted alkyl, or $R^7$ and $R^8$ together form a four-, five-, six-, or seven-membered heterocycle, $(C_1\text{-}C_8)$heteroalkyl, $(C_1\text{-}C_8)$substituted heteroalkyl, aryl, substituted aryl, heteroaryl, substituted heteroaryl;

X is —OH, —$NH_2$, —SH, —$OR^{11}$, —$NHR^{12}$, —$NR^{13}R^{14}$, —$OC(O)R^{15}$, —$NHC(O)R^{16}$, —$SC(O)R^{17}$, —$C(O)OH$, —$C(O)OR^{18}$, —$C(O)NHR^{19}$, —$C(O)NR^{20}R^{21}$, —$N_3$;

$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from $(C_1\text{-}C_8)$alkyl, $(C_1\text{-}C_8)$substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —$P(O)(O\text{—})$-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O)$(CH_2)_b$-[Nucleoside Triphosphate], where b is 1, 2, 3, 4, 5, 6, 7, 8, 9 or 10;

EWG is an electron withdrawing group;

$R^{22}$ and $R^{23}$ are independently selected from —$CH_3$, —$CH_2CH_3$, —$CH(CH_3)_2$ or $R^{22}$ and $R^{23}$ together form a heterocycle.

Another set of compounds is represented by Structure 15, below:

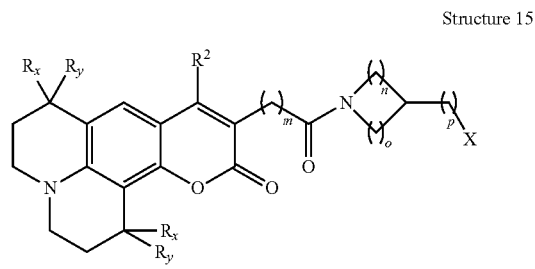

Structure 15 where
m is 0, 1, 2, 3, 4, 5, 6, 7, 8, 9 or 10;
n is 0, 1, 2 or 3;
o is 0, 1, 2 or 3;
p is 0, 1, 2, 3, 4, 5, 6, 7, 8, 9 or 10;
$R^2$ is selected from a group consisting of —H or —$CH_3$;
X is —OH, —$NH_2$, —SH, —$OR^{11}$, —$NHR^{12}$, —$NR^{13}R^{14}$, —$OC(O)R^{15}$, —$NHC(O)R^{16}$, —$SC(O)R^{17}$, —$C(O)OH$, —$C(O)OR^{18}$, —$C(O)NHR^{19}$, —$C(O)NR^{20}R^{21}$, —$N_3$;

$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from $(C_1-C_8)$alkyl, $(C_1-C_8)$substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —P(O)(O—)-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O)$(CH_2)_b$-[Nucleoside Triphosphate], where b is 1, 2, 3, 4, 5, 6, 7, 8, 9 or 10;

EWG is an electron withdrawing group;

$R^{22}$ and $R^{23}$ are independently selected from —$CH_3$, —$CH_2CH_3$, —$CH(CH_3)_2$ or $R^{22}$ and $R^{23}$ together form a heterocycle;

$R_x$ and $R_y$ are independently H or $CH_3$.

Another set of compounds is represented by Structure 16, below:

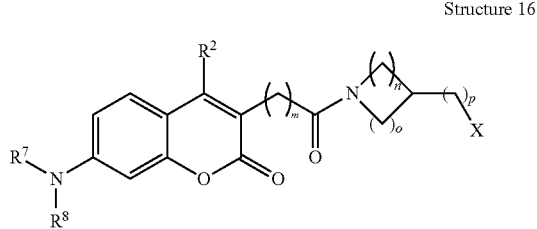

Structure 16 where m is 0, 1, 2, 3, 4, 5, 6, 7, 8, 9 or 10;

n is 0, 1, 2 or 3;

o is 0, 1, 2 or 3;

p is 0, 1, 2, 3, 4, 5, 6, 7, 8, 9 or 10;

$R^2$ is selected from a group consisting of —H or —$CH_3$;

$R^7$ and $R^8$ are independently selected from H, $(C_1-C_8)$alkyl, $(C_1-C_8)$substituted alkyl, or $R^7$ and $R^8$ together form a five-, six-, or seven-membered heterocycle;

X is —OH, —$NH_2$, —SH, —$OR^{11}$, —$NHR^{12}$, —$NR^{13}R^{14}$, —$OC(O)R^{15}$, —$NHC(O)R^{16}$, —$SC(O)R^{17}$, —C(O)OH, —$C(O)OR^{18}$, —$C(O)NHR^{19}$, —$C(O)NR^{20}R^{21}$, —$N_3$;

$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from $(C_1-C_8)$alkyl, $(C_1-C_8)$substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —P(O)(O—)-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O)$(CH_2)_b$-[Nucleoside Triphosphate], where b is 1, 2, 3, 4, 5, 6, 7, 8, 9 or 10;

EWG is an electron withdrawing group;

$R^{22}$ and $R^{23}$ are independently selected from —$CH_3$, —$CH_2CH_3$, —$CH(CH_3)_2$ or $R^{22}$ and $R^{23}$ together form a heterocycle.

Another set of compounds is represented by Structure 17, below:

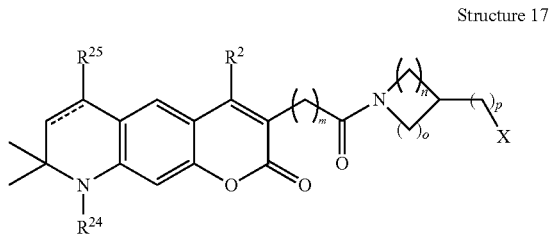

Structure 17 where m is 0, 1, 2, 3, 4, 5, 6, 7, 8, 9 or 10;

n is 0, 1, 2 or 3;

o is 0, 1, 2 or 3;

p is 0, 1, 2, 3, 4, 5, 6, 7, 8, 9 or 10;

$R^2$ is selected from a group consisting of —H or —$CH_3$;

the dashed line represents an optional double bond;

X is —OH, —$NH_2$, —SH, —$OR^{11}$, —$NHR^{12}$, —$NR^{13}R^{14}$, —$OC(O)R^{15}$, —$NHC(O)R^{16}$, —$SC(O)R^{17}$, —C(O)OH, —$C(O)OR^{18}$, —$C(O)NHR^{19}$, —$C(O)NR^{20}R^{21}$, —$N_3$;

$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from $(C_1-C_8)$alkyl, $(C_1-C_8)$substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —P(O)(O—)-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O)$(CH_2)_b$-[Nucleoside Triphosphate], where b is 1, 2, 3, 4, 5, 6, 7, 8, 9 or 10;

EWG is an electron withdrawing group;

$R^{22}$ and $R^{23}$ are independently selected from —$CH_3$, —$CH_2CH_3$, —$CH(CH_3)_2$ or $R^{22}$ and $R^{23}$ together form a heterocycle;

$R^{24}$ is $(C_1-C_8)$alkyl or $(C_1-C_8)$substituted alkyl;

$R^{25}$ is $(C_1-C_8)$alkyl, $(C_1-C_8)$substituted alkyl or $CH_2SO_3H$.

Another set of compounds is represented by Structure 18, below:

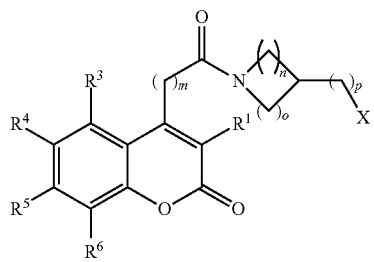

Structure 18 where m is 0, 1, 2, 3, 4, 5, 6, 7, 8, 9 or 10;

n is 0, 1, 2 or 3;

o is 0, 1, 2 or 3;

p is 0, 1, 2, 3, 4, 5, 6, 7, 8, 9 or 10;

$R^1$ is selected from a group consisting of —H or —$CH_3$;

$R^3$ is selected from a group consisting of —H, -halogen, —$CF_3$, —OH, —$NH_2$, —CCH, —CN, —$NO_2$, $(C_1-C_8)$alkyl, $(C_1-C_8)$substituted alkyl, $(C_1-C_8)$alkylthio, $(C_1-C_8)$ substituted alkylthio, (C₁-C₈)alkoxy, (C₁-C₈)substituted alkoxy, —NR⁷R⁸ where R⁷ and R⁸ are independently selected from H, (C₁-C₈)alkyl, or R⁷ and R⁸ together form a four-, five-, six-, or seven-membered heterocycle, (C₁-C₈)heteroalkyl, (C₁-C₈)substituted heteroalkyl, aryl, substituted aryl, heteroaryl, substituted heteroaryl, or R³ together with R⁴ form a five- or six-membered carbocyclic or heterocyclic ring (e.g., piperidinyl);

R⁴ is selected from a group consisting of —H, -halogen, —CF₃, —OH, —NH₂, —CCH, —CN, —NO₂, (C₁-C₈)alkyl, (C₁-C₈)substituted alkyl, (C₁-C₈)alkylthio, (C₁-C₈)substituted alkylthio, (C₁-C₈)alkoxy, (C₁-C₈)substituted alkoxy, —NR⁷R⁸ where R⁷ and R⁸ are independently selected from H, (C₁-C₈)alkyl, or R⁷ and R⁸ together form a four-, five-, six-, or seven-membered heterocycle, (C₁-C₈)heteroalkyl, (C₁-C₈)substituted heteroalkyl, aryl, substituted aryl, heteroaryl, substituted heteroaryl, or R⁴ together with R⁵ form a five- or six-membered carbocyclic or heterocyclic ring (e.g., piperidinyl);

R⁵ is selected from a group consisting of —H, -halogen, —CF₃, —OH, —NH₂, —CCH, —CN, —NO₂, (C₁-C₈)alkyl, (C₁-C₈)substituted alkyl, (C₁-C₈)alkylthio, (C₁-C₈)substituted alkylthio, (C₁-C₈)alkoxy, (C₁-C₈)substituted alkoxy, —NR⁷R⁸ where R⁷ and R⁸ are independently selected from H, (C₁-C₈)alkyl, or R⁷ and R⁸ together form a four-, five-, six-, or seven-membered heterocycle, (C₁-C₈)heteroalkyl, (C₁-C₈)substituted heteroalkyl, aryl, substituted aryl, heteroaryl, substituted heteroaryl, or R⁵ together with R⁶ form a five- or six-membered carbocyclic or heterocyclic ring (e.g., piperidinyl); or R⁴, R⁵ and R⁶ together form fused carbocyclic or heterocyclic ring systems having five- or six-membered rings;

R⁶ is selected from a group consisting of —H, -halogen, —CF₃, —OH, —NH₂, —CCH, —CN, —NO₂, (C₁-C₈)alkyl, (C₁-C₈)substituted alkyl, (C₁-C₈)alkylthio, (C₁-C₈)substituted alkylthio, (C₁-C₈)alkoxy, (C₁-C₈)substituted alkoxy, —NR⁷R⁸ where R⁷ and R⁸ are independently selected from H, (C₁-C₈)alkyl, (C₁-C₈)substituted alkyl, or R⁷ and R⁸ together form a four-, five-, six-, or seven-membered heterocycle, (C₁-C₈)heteroalkyl, (C₁-C₈)substituted heteroalkyl, aryl, substituted aryl, heteroaryl, substituted heteroaryl;

X is —OH, —NH₂, —SH, —OR¹¹, —NHR¹², —NR¹³R¹⁴, —OC(O)R¹⁵, —NHC(O)R¹⁶, —SC(O)R¹⁷, —C(O)OH, —C(O)OR¹⁸, —C(O)NHR¹⁹, —C(O)NR²⁰R²¹, —N₃;

R¹¹, R¹², R¹³, R¹⁴, R¹⁵, R¹⁶, R¹⁷, R¹⁸, R¹⁹, R²⁰ and R²¹ are independently selected from (C₁-C₈)alkyl, (C₁-C₈)substituted alkyl, —CH₂CH(OH)CH₂(OH), —CH(CH₂OH)₂, —CH₂CCH, —(CH₂CH₂O)ₐ—CH₂CH₂OH where a is 1, 2, 3, 4, 5, 6, 7, 8, 9 or 10, —P(NR²²R²³)OCH₂CH₂-EWG, —P(O)(O—)-Oligonucleotide, —(CH₂)ᵦCC-Nucleoside, —(CH₂)ᵦCC-[Nucleoside Triphosphate], —(CH₂)ᵦ-Nucleoside, —(CH₂)ᵦ-[Nucleoside Triphosphate], —(CH₂)ᵦNH-Nucleoside, —(CH₂)ᵦNH-[Nucleoside Triphosphate], —(CH₂)ᵦNHC(O)(CH₂)ᵦ-Nucleoside, —(CH₂)ᵦNHC(O)(CH₂)ᵦ-[Nucleoside Triphosphate], where b is 1, 2, 3, 4, 5, 6, 7, 8, 9 or 10;

EWG is an electron withdrawing group;

R²² and R²³ are independently selected from —CH₃, —CH₂CH₃, —CH(CH₃)₂ or R²² and R²³ together form a heterocycle.

Another set of compounds is represented by Structure 19, below:

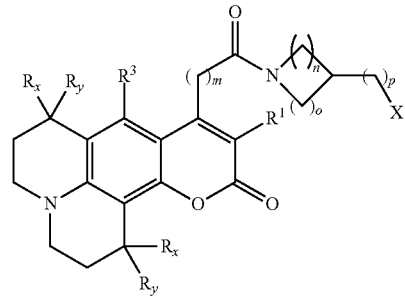

Structure 19 where
m is 0, 1, 2, 3, 4, 5, 6, 7, 8, 9 or 10;
n is 0, 1, 2 or 3;
o is 0, 1, 2 or 3;
p is 0, 1, 2, 3, 4, 5, 6, 7, 8, 9 or 10;
R¹ is selected from a group consisting of —H or —CH₃;
X is —OH, —NH₂, —SH, —OR¹¹, —NHR¹², —NR¹³R¹⁴, —OC(O)R¹⁵, —NHC(O)R¹⁶, —SC(O)R¹⁷, —C(O)OH, —C(O)OR¹⁸, —C(O)NHR¹⁹, —C(O)NR²⁰R²¹, —N₃;

R¹¹, R¹², R¹³, R¹⁴, R¹⁵, R¹⁶, R¹⁷, R¹⁸, R¹⁹, R²⁰ and R²¹ are independently selected from (C₁-C₈)alkyl, (C₁-C₈)substituted alkyl, —CH₂CH(OH)CH₂(OH), —CH(CH₂OH)₂, —CH₂CCH, —(CH₂CH₂O)ₐ—CH₂CH₂OH where a is 1, 2, 3, 4, 5, 6, 7, 8, 9 or 10, —P(NR²²R²³)OCH₂CH₂-EWG, —P(O)(O—)-Oligonucleotide, —(CH₂)ᵦCC-Nucleoside, —(CH₂)ᵦCC-[Nucleoside Triphosphate], —(CH₂)ᵦ-Nucleoside, —(CH₂)ᵦ-[Nucleoside Triphosphate], —(CH₂)ᵦNH-Nucleoside, —(CH₂)ᵦNH-[Nucleoside Triphosphate], —(CH₂)ᵦNHC(O)(CH₂)ᵦ-Nucleoside, —(CH₂)ᵦNHC(O)(CH₂)ᵦ-[Nucleoside Triphosphate], where b is 1, 2, 3, 4, 5, 6, 7, 8, 9 or 10;

R²² and R²³ are independently selected from —CH₃, —CH₂CH₃, —CH(CH₃)₂ or R²² and R²³ together form a heterocycle;

Rₓ and Rᵧ are independently H or CH₃;
EWG is an electron withdrawing group.

Another set of compounds is represented by Structure 20, below:

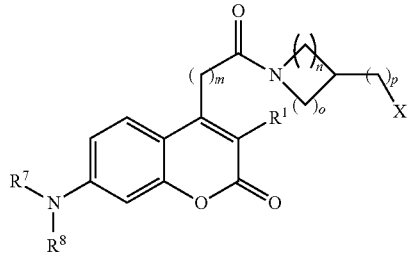

Structure 20 where
m is 0, 1, 2, 3, 4, 5, 6, 7, 8, 9 or 10;
n is 0, 1, 2 or 3;
o is 0, 1, 2 or 3;
p is 0, 1, 2, 3, 4, 5, 6, 7, 8, 9 or 10;
R¹ is selected from a group consisting of —H or —CH₃;
R⁷ and R⁸ are independently selected from H, (C₁-C₈)alkyl, (C₁-C₈)substituted alkyl, or R⁷ and R⁸ together form a five-, six-, or seven-membered heterocycle;

X is —OH, —NH$_2$, —SH, —OR$^{11}$, —NHR$^{12}$, —NR$^{13}$R$^{14}$, —OC(O)R$^{15}$, —NHC(O)R$^{16}$, —SC(O)R$^{17}$, —C(O)OH, —C(O)OR$^{18}$, —C(O)NHR$^{19}$, —C(O)NR$^{20}$R$^{21}$, —N$_3$;

R$^{11}$, R$^{12}$, R$^{13}$, R$^{14}$, R$^{15}$, R$^{16}$, R$^{17}$, R$^{18}$, R$^{19}$, R$^{20}$ and R$^{21}$ are independently selected from (C$_1$-C$_8$)alkyl, (C$_1$-C$_8$)substituted alkyl, —CH$_2$CH(OH)CH$_2$(OH), —CH(CH$_2$OH)$_2$, —CH$_2$CCH, —(CH$_2$CH$_2$O)$_a$—CH$_2$CH$_2$OH where a is 1, 2, 3, 4, 5, 6, 7, 8, 9 or 10, —P(NR$^{22}$R$^{23}$)OCH$_2$CH$_2$-EWG, —P(O)(O—)-Oligonucleotide, —(CH$_2$)$_b$CC-Nucleoside, —(CH$_2$)$_b$CC-[Nucleoside Triphosphate], —(CH$_2$)$_b$-Nucleoside, —(CH$_2$)$_b$-[Nucleoside Triphosphate], —(CH$_2$)$_b$NH-Nucleoside, —(CH$_2$)$_b$NH-[Nucleoside Triphosphate], —(CH$_2$)$_b$NHC(O)(CH$_2$)$_b$-Nucleoside, —(CH$_2$)$_b$NHC(O)(CH$_2$)$_b$-[Nucleoside Triphosphate], where b is 1, 2, 3, 4, 5, 6, 7, 8, 9 or 10;

EWG is an electron withdrawing group;

R$^{22}$ and R$^{23}$ are independently selected from —CH$_3$, —CH$_2$CH$_3$, —CH(CH$_3$)$_2$ or R$^{22}$ and R$^{23}$ together form a heterocycle.

Another set of compounds is represented by Structure 21, below:

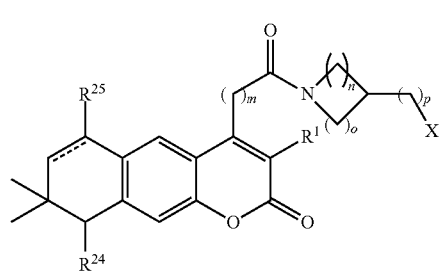

Structure 21 where
m is 0, 1, 2, 3, 4, 5, 6, 7, 8, 9 or 10;
n is 0, 1, 2 or 3;
o is 0, 1, 2 or 3;
p is 0, 1, 2, 3, 4, 5, 6, 7, 8, 9 or 10;
R$^1$ is selected from a group consisting of —H or —CH$_3$;
the dashed line represents an optional double bond;
X is —OH, —NH$_2$, —SH, —OR$^{11}$, —NHR$^{12}$, —NR$^{13}$R$^{14}$, —OC(O)R$^{15}$, —NHC(O)R$^{16}$, —SC(O)R$^{17}$, —C(O)OH, —C(O)OR$^{18}$, —C(O)NHR$^{19}$, —C(O)NR$^{20}$R$^{21}$, —N$_3$;

R$^{11}$, R$^{12}$, R$^{13}$, R$^{14}$, R$^{15}$, R$^{16}$, R$^{17}$, R$^{18}$, R$^{19}$, R$^{20}$ and R$^{21}$ are independently selected from (C$_1$-C$_8$)alkyl, (C$_1$-C$_8$)substituted alkyl, —CH$_2$CH(OH)CH$_2$(OH), —CH(CH$_2$OH)$_2$, —CH$_2$CCH, —(CH$_2$CH$_2$O)$_a$—CH$_2$CH$_2$OH where a is 1, 2, 3, 4, 5, 6, 7, 8, 9 or 10, —P(NR$^{22}$R$^{23}$)OCH$_2$CH$_2$-EWG, —P(O)(O—)-Oligonucleotide, —(CH$_2$)$_b$CC-Nucleoside, —(CH$_2$)$_b$CC-[Nucleoside Triphosphate], —(CH$_2$)$_b$-Nucleoside, —(CH$_2$)$_b$-[Nucleoside Triphosphate], —(CH$_2$)$_b$NH-Nucleoside, —(CH$_2$)$_b$NH-[Nucleoside Triphosphate], —(CH$_2$)$_b$NHC(O)(CH$_2$)$_b$-Nucleoside, —(CH$_2$)$_b$NHC(O)(CH$_2$)$_b$-[Nucleoside Triphosphate], where b is 1, 2, 3, 4, 5, 6, 7, 8, 9 or 10;

EWG is an electron withdrawing group;

R$^{22}$ and R$^{23}$ are independently selected from —CH$_3$, —CH$_2$CH$_3$, —CH(CH$_3$)$_2$ or R$^{22}$ and R$^{23}$ together form a heterocycle;

R$^{24}$ is (C$_1$-C$_8$)alkyl or (C$_1$-C$_8$)substituted alkyl;
R$^{25}$ is (C$_1$-C$_8$)alkyl, (C$_1$-C$_8$)substituted alkyl or CH$_2$SO$_3$H.

Another set of compounds is represented by Structure 22, below:

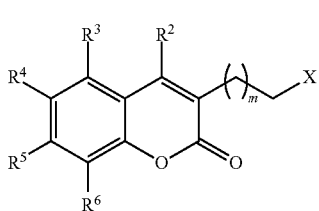

Structure 22 where
m is 0, 1, 2, 3, 4, 5, 6, 7, 8, 9 or 10;
R$^2$ is selected from a group consisting of —H or —CH$_3$;
R$^3$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or R$^3$ together with R$^4$ form a five- or six-membered carbocyclic or heterocyclic ring (e.g., piperidinyl);

R$^4$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or R$^4$ together with R$^5$ form a five- or six-membered carbocyclic or heterocyclic ring (e.g., piperidinyl);

R$^5$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or R$^5$ together with R$^6$ form a five- or six-membered carbocyclic or heterocyclic ring (e.g., piperidinyl); or R$^4$, R$^5$ and R$^6$ together form fused carbocyclic or heterocyclic ring systems having five- or six-membered rings;

R$^6$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, (C$_1$-C$_8$)substituted alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl;

X is —OH, —NH$_2$, —SH, —OR$^{11}$, —NHR$^{12}$, —NR$^{13}$R$^{14}$, —OC(O)R$^{15}$, —NHC(O)R$^{16}$, —SC(O)R$^{17}$, —C(O)OH, —C(O)OR$^{18}$, —C(O)NHR$^{19}$, —C(O)NR$^{20}$R$^{21}$, —N$_3$;

$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from ($C_1$-$C_8$)alkyl, ($C_1$-$C_8$)substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —P(O)(O—)-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O)$(CH_2)_b$-[Nucleoside Triphosphate], where b is 1, 2, 3, 4, 5, 6, 7, 8, 9 or 10;

EWG is an electron withdrawing group;

$R^{22}$ and $R^{23}$ are independently selected from —$CH_3$, —$CH_2CH_3$, —$CH(CH_3)_2$ or $R^{22}$ and $R^{23}$ together form a heterocycle.

Another set of compounds is represented by Structure 23, below:

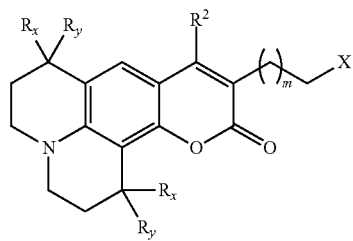

Structure 23 where m is 0, 1, 2, 3, 4, 5, 6, 7, 8, 9 or 10;

$R^2$ is selected from a group consisting of —H or —$CH_3$;

X is —OH, —$NH_2$, —SH, —$OR^{11}$, —$NHR^{12}$, —$NR^{13}R^{14}$, —$OC(O)R^{15}$, —$NHC(O)R^{16}$, —$SC(O)R^{17}$, —C(O)OH, —$C(O)OR^{18}$, —$C(O)NHR^{19}$, —$C(O)NR^{20}R^{21}$, —$N_3$;

$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from ($C_1$-$C_8$)alkyl, ($C_1$-$C_8$)substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —P(O)(O—)-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O)$(CH_2)_b$-[Nucleoside Triphosphate], where b is 1, 2, 3, 4, 5, 6, 7, 8, 9 or 10;

EWG is an electron withdrawing group;

$R_x$ and $R_y$ are independently H or $CH_3$;

$R^{22}$ and $R^{23}$ are independently selected from —$CH_3$, —$CH_2CH_3$, —$CH(CH_3)_2$ or $R^{22}$ and $R^{23}$ together form a heterocycle.

Another set of compounds is represented by Structure 24, below:

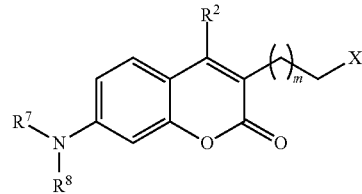

Structure 24 where m is 0, 1, 2, 3, 4, 5, 6, 7, 8, 9 or 10;

$R^2$ is selected from a group consisting of —H or —$CH_3$;

$R^7$ and $R^8$ are independently selected from H, ($C_1$-$C_8$) alkyl, ($C_1$-$C_8$)substituted alkyl, or $R^7$ and $R^8$ together form a five-, six-, or seven-membered heterocycle;

X is —OH, —$NH_2$, —SH, —$OR^{11}$, —$NHR^{12}$, —$NR^{13}R^{14}$, —$OC(O)R^{15}$, —$NHC(O)R^{16}$, —$SC(O)R^{17}$, —C(O)OH, —$C(O)OR^{18}$, —$C(O)NHR^{19}$, —$C(O)NR^{20}R^{21}$, —$N_3$;

$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from ($C_1$-$C_8$)alkyl, ($C_1$-$C_8$)substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —P(O)(O—)-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O)$(CH_2)_b$-[Nucleoside Triphosphate], where b is 1, 2, 3, 4, 5, 6, 7, 8, 9 or 10;

EWG is an electron withdrawing group;

$R^{22}$ and $R^{23}$ are independently selected from —$CH_3$, —$CH_2CH_3$, —$CH(CH_3)_2$ or $R^{22}$ and $R^{23}$ together form a heterocycle.

Another set of compounds is represented by Structure 25, below:

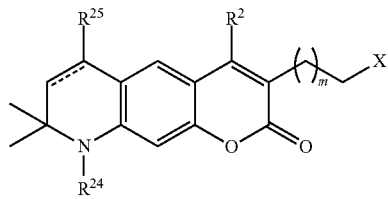

Structure 25 where m is 0, 1, 2, 3, 4, 5, 6, 7, 8, 9 or 10;

$R^2$ is selected from a group consisting of —H or —$CH_3$;

the dashed line represents an optional double bond;

X is —OH, —$NH_2$, —SH, —$OR^{11}$, —$NHR^{12}$, —$NR^{13}R^{14}$, —$OC(O)R^{15}$, —$NHC(O)R^{16}$, —$SC(O)R^{17}$, —C(O)OH, —$C(O)OR^{18}$, —$C(O)NHR^{19}$, —$C(O)NR^{20}R^{21}$, —$N_3$;

$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from ($C_1$-$C_8$)alkyl, ($C_1$-$C_8$)substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —P(O)(O—)-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH- Nucleoside, —(CH$_2$)$_b$NH-[Nucleoside Triphosphate], —(CH$_2$)$_b$NHC(O)(CH$_2$)$_b$-Nucleoside, —(CH$_2$)$_b$NHC(O)(CH$_2$)$_b$-[Nucleoside Triphosphate], where b is 1, 2, 3, 4, 5, 6, 7, 8, 9 or 10;

EWG is an electron withdrawing group;

R$^{22}$ and R$^{23}$ are independently selected from —CH$_3$, —CH$_2$CH$_3$, —CH(CH$_3$)$_2$ or R$^{22}$ and R$^{23}$ together form a heterocycle;

R$^{24}$ is (C$_1$-C$_8$)alkyl or (C$_1$-C$_8$)substituted alkyl;

R$^{25}$ is (C$_1$-C$_8$)alkyl, (C$_1$-C$_8$)substituted alkyl or CH$_2$SO$_3$H.

Another set of compounds is represented by Structure 26, below:

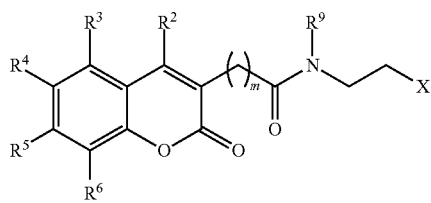

Structure 26 where m is 0, 1, 2, 3, 4, 5, 6, 7, 8, 9 or 10;

R$^2$ is selected from a group consisting of —H or —CH$_3$;

R$^3$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or R$^3$ together with R$^4$ form a five- or six-membered carbocyclic or heterocyclic ring (e.g., piperidinyl);

R$^4$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or R$^4$ together with R$^5$ form a five- or six-membered carbocyclic or heterocyclic ring (e.g., piperidinyl);

R$^5$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or R$^5$ together with R$^6$ form a five- or six-membered carbocyclic or heterocyclic ring (e.g., piperidinyl); or R$^4$, R$^5$ and R$^6$ together form fused carbocyclic or heterocyclic ring systems having five- or six-membered rings;

R$^6$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, (C$_1$-C$_8$)substituted alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl;

R$^9$ is —H, —CH$_3$, —CH$_2$CH$_3$, —CH(CH$_3$)$_2$;

X is —OH, —NH$_2$, —SH, —OR$^{11}$, —NHR$^{12}$, —NR$^{13}$R$^{14}$, —OC(O)R$^{15}$, —NHC(O)R$^{16}$, —SC(O)R$^{17}$, —C(O)OH, —C(O)OR$^{18}$, —C(O)NHR$^{19}$, —C(O)NR$^{20}$R$^{21}$, —N$_3$;

R$^{11}$, R$^{12}$, R$^{13}$, R$^{14}$, R$^{15}$, R$^{16}$, R$^{17}$, R$^{18}$, R$^{19}$, R$^{20}$ and R$^{21}$ are independently selected from (C$_1$-C$_8$)alkyl, (C$_1$-C$_8$)substituted alkyl, —CH$_2$CH(OH)CH$_2$(OH), —CH(CH$_2$OH)$_2$, —CH$_2$CCH, —(CH$_2$CH$_2$O)$_a$—CH$_2$CH$_2$OH where a is 1, 2, 3, 4, 5, 6, 7, 8, 9 or 10, —P(NR$^{22}$R$^{23}$)OCH$_2$CH$_2$-EWG, —P(O)(O—)-Oligonucleotide, —(CH$_2$)$_b$CC-Nucleoside, —(CH$_2$)$_b$CC-[Nucleoside Triphosphate], —(CH$_2$)$_b$-Nucleoside, —(CH$_2$)$_b$-[Nucleoside Triphosphate], —(CH$_2$)$_b$NH-Nucleoside, —(CH$_2$)$_b$NH-[Nucleoside Triphosphate], —(CH$_2$)$_b$NHC(O)(CH$_2$)$_b$-Nucleoside, —(CH$_2$)$_b$NHC(O)(CH$_2$)$_b$-[Nucleoside Triphosphate], where b is 1, 2, 3, 4, 5, 6, 7, 8, 9 or 10;

EWG is an electron withdrawing group;

R$^{22}$ and R$^{23}$ are independently selected from —CH$_3$, —CH$_2$CH$_3$, —CH(CH$_3$)$_2$ or R$^{22}$ and R$^{23}$ together form a heterocycle.

Another set of compounds is represented by Structure 27, below:

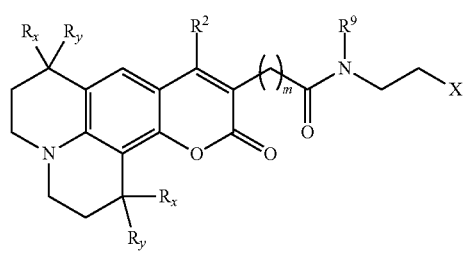

Structure 27 where m is 0, 1, 2, 3, 4, 5, 6, 7, 8, 9 or 10;

R$^2$ is selected from a group consisting of —H or —CH$_3$;

R$^9$ is —H, —CH$_3$, —CH$_2$CH$_3$, —CH(CH$_3$)$_2$;

X is —OH, —NH$_2$, —SH, —OR$^{11}$, —NHR$^{12}$, —NR$^{13}$R$^{14}$, —OC(O)R$^{15}$, —NHC(O)R$^{16}$, —SC(O)R$^{17}$, —C(O)OH, —C(O)OR$^{18}$, —C(O)NHR$^{19}$, —C(O)NR$^{20}$R$^{21}$, —N$_3$;

R$^{11}$, R$^{12}$, R$^{13}$, R$^{14}$, R$^{15}$, R$^{16}$, R$^{17}$, R$^{18}$, R$^{19}$, R$^{20}$ and R$^{21}$ are independently selected from (C$_1$-C$_8$)alkyl, (C$_1$-C$_8$)substituted alkyl, —CH$_2$CH(OH)CH$_2$(OH), —CH(CH$_2$OH)$_2$, —CH$_2$CCH, —(CH$_2$CH$_2$O)$_a$—CH$_2$CH$_2$OH where a is 1, 2, 3, 4, 5, 6, 7, 8, 9 or 10, —P(NR$^{22}$R$^{23}$)OCH$_2$CH$_2$-EWG, —P(O)(O—)-Oligonucleotide, —(CH$_2$)$_b$CC-Nucleoside, —(CH$_2$)$_b$CC-[Nucleoside Triphosphate], —(CH$_2$)$_b$-Nucleoside, —(CH$_2$)$_b$-[Nucleoside Triphosphate], —(CH$_2$)$_b$NH-Nucleoside, —(CH$_2$)$_b$NH-[Nucleoside Triphosphate], —(CH$_2$)$_b$NHC(O)(CH$_2$)$_b$-Nucleoside, —(CH$_2$)$_b$NHC(O)(CH$_2$)$_b$-[Nucleoside Triphosphate], where b is 1, 2, 3, 4, 5, 6, 7, 8, 9 or 10;

EWG is an electron withdrawing group;

R$_x$ and R$_y$ are independently H and CH$_3$;

$R^{22}$ and $R^{23}$ are independently selected from —$CH_3$, —$CH_2CH_3$, —$CH(CH_3)_2$ or $R^{22}$ and $R^{23}$ together form a heterocycle.

Another set of compounds is represented by Structure 28, below:

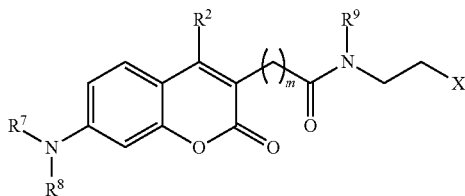

Structure 28 where
m is 0, 1, 2, 3, 4, 5, 6, 7, 8, 9 or 10;
$R^2$ is selected from a group consisting of —H or —$CH_3$;
$R^7$ and $R^8$ are independently selected from H, ($C_1$-$C_8$) alkyl, ($C_1$-$C_8$)substituted alkyl, or $R^7$ and $R^8$ together form a five-, six-, or seven-membered heterocycle;
$R^9$ is —H, —$CH_3$, —$CH_2CH_3$, —$CH(CH_3)_2$;
X is —OH, —$NH_2$, —SH, —$OR^{11}$, —$NHR^{12}$, —$NR^{13}R^{14}$, —$OC(O)R^{15}$, —$NHC(O)R^{16}$, —$SC(O)R^{17}$, —$C(O)OH$, —$C(O)OR^{18}$, —$C(O)NHR^{19}$, —$C(O)NR^{20}R^{21}$, —$N_3$;
$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from ($C_1$-$C_8$)alkyl, ($C_1$-$C_8$)substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —$P(O)(O—)$-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O)$(CH_2)_b$-[Nucleoside Triphosphate], where b is 1, 2, 3, 4, 5, 6, 7, 8, 9 or 10;
EWG is an electron withdrawing group;
$R^{22}$ and $R^{23}$ are independently selected from —$CH_3$, —$CH_2CH_3$, —$CH(CH_3)_2$ or $R^{22}$ and $R^{23}$ together form a heterocycle.

Another set of compounds is represented by Structure 29, below:

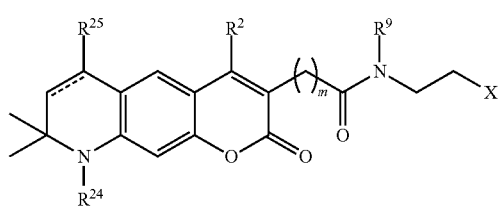

Structure 29 where
m is 0, 1, 2, 3, 4, 5, 6, 7, 8, 9 or 10;
$R^2$ is selected from a group consisting of —H or —$CH_3$;
$R^9$ is —H, —$CH_3$, —$CH_2CH_3$, —$CH(CH_3)_2$;
the dashed line represents an optional double bond;
X is —OH, —$NH_2$, —SH, —$OR^{11}$, —$NHR^{12}$, —$NR^{13}R^{14}$, —$OC(O)R^{15}$, —$NHC(O)R^{16}$, —$SC(O)R^{17}$, —$C(O)OH$, —$C(O)OR^{18}$, —$C(O)NHR^{19}$, —$C(O)NR^{20}R^{21}$, —$N_3$;

$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from ($C_1$-$C_8$)alkyl, ($C_1$-$C_8$)substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —$P(O)(O—)$-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O)$(CH_2)_b$-[Nucleoside Triphosphate], where b is 1, 2, 3, 4, 5, 6, 7, 8, 9 or 10;
EWG is an electron withdrawing group;
$R^{22}$ and $R^{23}$ are independently selected from —$CH_3$, —$CH_2CH_3$, —$CH(CH_3)_2$ or $R^{22}$ and $R^{23}$ together form a heterocycle;
$R^{24}$ is ($C_1$-$C_8$)alkyl or ($C_1$-$C_8$)substituted alkyl;
$R^{25}$ is ($C_1$-$C_8$)alkyl, ($C_1$-$C_8$)substituted alkyl or $CH_2SO_3H$.

Another set of compounds is represented by Structure 30, below:

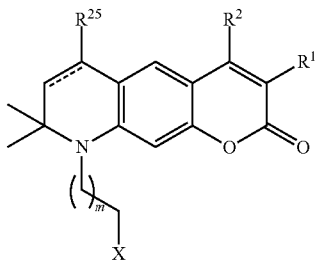

Structure 30 where
m is 0, 1, 2, 3, 4, 5, 6, 7, 8, 9 or 10;
$R^1$ is selected from a group consisting of —H or $CH_3$;
$R^2$ is selected from a group consisting of —H or —$CH_3$;
X is —OH, —$NH_2$, —SH, —$OR^{11}$, —$NHR_{12}$, —$NR^{13}R^{14}$, —$OC(O)R^{15}$, —$NHC(O)R^{16}$, —$SC(O)R^{17}$, —$C(O)OH$, —$C(O)OR^{18}$, —$C(O)NHR^{19}$, —$C(O)NR^{20}R^{21}$, —$N_3$;
$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from ($C_1$-$C_8$)alkyl, ($C_1$-$C_8$)substituted alkyl, —$CH_2CH(OH)CH_2(OH)$, —$CH(CH_2OH)_2$, —$CH_2CCH$, —$(CH_2CH_2O)_a$—$CH_2CH_2OH$ where a is 1, 2, 3, 4, 5, 6, 7, 8, 9 or 10, —$P(NR^{22}R^{23})OCH_2CH_2$-EWG, —$P(O)(O—)$-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O)$(CH_2)_b$-[Nucleoside Triphosphate], where b is 1, 2, 3, 4, 5, 6, 7, 8, 9 or 10;
EWG is an electron withdrawing group;
$R^{22}$ and $R^{23}$ are independently selected from —$CH_3$, —$CH_2CH_3$, —$CH(CH_3)_2$ or $R^{22}$ and $R^{23}$ together form a heterocycle;
$R^{25}$ is ($C_1$-$C_8$)alkyl, ($C_1$-$C_8$)substituted alkyl or $CH_2SO_3H$.

Another set of compounds is represented by Structure 31, below:

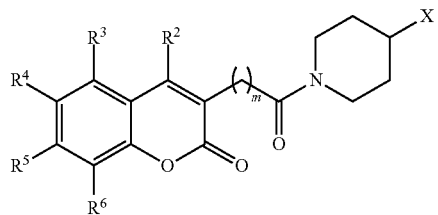

Structure 31 where
m is 0, 1, 2, 3, 4, 5, 6, 7, 8, 9 or 10;
$R^2$ is selected from a group consisting of —H or —CH$_3$;
$R^3$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or R$^3$ together with R$^4$ form a five- or six-membered carbocyclic or heterocyclic ring (e.g., piperidinyl);
$R^4$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or R$^4$ together with R$^5$ form a five- or six-membered carbocyclic or heterocyclic ring (e.g., piperidinyl);
$R^5$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or R$^5$ together with R$^6$ form a five- or six-membered carbocyclic or heterocyclic ring (e.g., piperidinyl); or R$^4$, R$^5$ and R$^6$ together form fused carbocyclic or heterocyclic ring systems having five- or six-membered rings;
$R^6$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where R$^7$ and R$^8$ are independently selected from H, (C$_1$-C$_8$)alkyl, (C$_1$-C$_8$)substituted alkyl, or R$^7$ and R$^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl;
X is —OH, —NH$_2$, —SH, —OR$^{11}$, —NHR$^{12}$, —NR$^{13}$R$^{14}$, —OC(O)R$^{15}$, —NHC(O)R$^{16}$, —SC(O)R$^{17}$, —C(O)OH, —C(O)OR$^{18}$, —C(O)NHR$^{19}$, —C(O)NR$^{20}$R$^{21}$, —N$_3$;
$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from (C$_1$-C$_8$)alkyl, (C$_1$-C$_8$)substituted alkyl, —CH$_2$CH(OH)CH$_2$(OH), —CH(CH$_2$OH)$_2$, —CH$_2$CCH, —(CH$_2$CH$_2$O)$_a$—CH$_2$CH$_2$OH where a is 1, 2, 3, 4, 5, 6, 7, 8, 9 or 10, —P(NR$^{22}$R$^{23}$)OCH$_2$CH$_2$-EWG, —P(O)(O—)-Oligonucleotide, —(CH$_2$)$_b$CC-Nucleoside, —(CH$_2$)$_b$CC-[Nucleoside Triphosphate], —(CH$_2$)$_b$-Nucleoside, —(CH$_2$)$_b$-[Nucleoside Triphosphate], —(CH$_2$)$_b$NH-Nucleoside, —(CH$_2$)$_b$NH-[Nucleoside Triphosphate], —(CH$_2$)$_b$NHC(O)(CH$_2$)$_b$-Nucleoside, —(CH$_2$)$_b$NHC(O)(CH$_2$)$_b$-[Nucleoside Triphosphate], where b is 1, 2, 3, 4, 5, 6, 7, 8, 9 or 10;
EWG is an electron withdrawing group;
$R^{22}$ and $R^{23}$ are independently selected from —CH$_3$, —CH$_2$CH$_3$, —CH(CH$_3$)$_2$ or R$^{22}$ and R$^{23}$ together form a heterocycle.

Another set of compounds is represented by Structure 32, below:

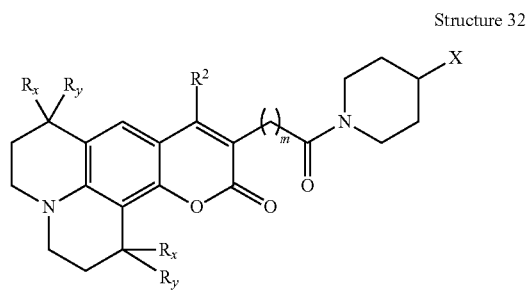

Structure 32 where
m is 0, 1, 2, 3, 4, 5, 6, 7, 8, 9 or 10;
$R^2$ is selected from a group consisting of —H or —CH$_3$;
X is —OH, —NH$_2$, —SH, —OR$^{11}$, —NHR$^{12}$, —NR$^{13}$R$^{14}$, —OC(O)R$^{15}$, —NHC(O)R$^{16}$, —SC(O)R$^{17}$, —C(O)OH, —C(O)OR$^{18}$, —C(O)NHR$^{19}$, —C(O)NR$^{20}$R$^{21}$, —N$_3$;
$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from (C$_1$-C$_8$)alkyl, (C$_1$-C$_8$)substituted alkyl, —CH$_2$CH(OH)CH$_2$(OH), —CH(CH$_2$OH)$_2$, —CH$_2$CCH, —(CH$_2$CH$_2$O)$_a$—CH$_2$CH$_2$OH where a is 1, 2, 3, 4, 5, 6, 7, 8, 9 or 10, —P(NR$^{22}$R$^{23}$)OCH$_2$CH$_2$-EWG, —P(O)(O—)-Oligonucleotide, —(CH$_2$)$_b$CC-Nucleoside, —(CH$_2$)$_b$CC-[Nucleoside Triphosphate], —(CH$_2$)$_b$-Nucleoside, —(CH$_2$)$_b$-[Nucleoside Triphosphate], —(CH$_2$)$_b$NH-Nucleoside, —(CH$_2$)$_b$NH-[Nucleoside Triphosphate], —(CH$_2$)$_b$NHC(O)(CH$_2$)$_b$-Nucleoside, —(CH$_2$)$_b$NHC(O)(CH$_2$)$_b$-[Nucleoside Triphosphate], where b is 1, 2, 3, 4, 5, 6, 7, 8, 9 or 10;
EWG is an electron withdrawing group;
$R_x$ and $R_y$ are independently H or CH$_3$;
$R^{22}$ and $R^{23}$ are independently selected from —CH$_3$, —CH$_2$CH$_3$, —CH(CH$_3$)$_2$ or R$^{22}$ and R$^{23}$ together form a heterocycle.

Another set of compounds is represented by Structure 33, below:

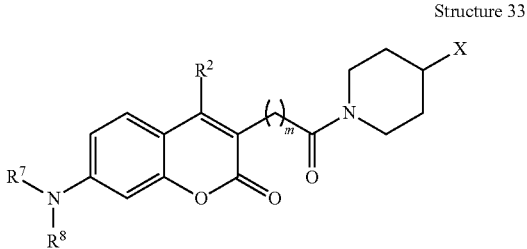

Structure 33 where
m is 0, 1, 2, 3, 4, 5, 6, 7, 8, 9 or 10;
$R^2$ is selected from a group consisting of —H or —CH$_3$;
$R^7$ and $R^8$ are independently selected from H, (C$_1$-C$_8$)alkyl, (C$_1$-C$_8$)substituted alkyl, or $R^7$ and $R^8$ together form a five-, six-, or seven-membered heterocycle;
X is —OH, —NH$_2$, —SH, —OR$^{11}$, —NHR$^{12}$, —NR$^{13}$R$^{14}$, —OC(O)R$^{15}$, —NHC(O)R$^{16}$, —SC(O)R$^{17}$, —C(O)OH, —C(O)OR$^{18}$, —C(O)NHR$^{19}$, —C(O)NR$^{20}$R$^{21}$, —N$_3$;
$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from (C$_1$-C$_8$)alkyl, (C$_1$-C$_8$)substituted alkyl, —CH$_2$CH(OH)CH$_2$(OH), —CH(CH$_2$OH)$_2$, —CH$_2$CCH, —(CH$_2$CH$_2$O)$_a$—CH$_2$CH$_2$OH where a is 1, 2, 3, 4, 5, 6, 7, 8, 9 or 10, —P(NR$^{22}$R$^{23}$)OCH$_2$CH$_2$-EWG, —P(O)(O—)-Oligonucleotide, —(CH$_2$)$_b$CC-Nucleoside, —(CH$_2$)$_b$CC-[Nucleoside Triphosphate], —(CH$_2$)$_b$-Nucleoside, —(CH$_2$)$_b$-[Nucleoside Triphosphate], —(CH$_2$)$_b$NH-Nucleoside, —(CH$_2$)$_b$NH-[Nucleoside Triphosphate], —(CH$_2$)$_b$NHC(O)(CH$_2$)$_b$-Nucleoside, —(CH$_2$)$_b$NHC(O)(CH$_2$)$_b$-[Nucleoside Triphosphate], where b is 1, 2, 3, 4, 5, 6, 7, 8, 9 or 10;
EWG is an electron withdrawing group;
$R^{22}$ and $R^{23}$ are independently selected from —CH$_3$, —CH$_2$CH$_3$, —CH(CH$_3$)$_2$ or $R^{22}$ and $R^{23}$ together form a heterocycle.

Another set of compounds is represented by Structure 34, below:

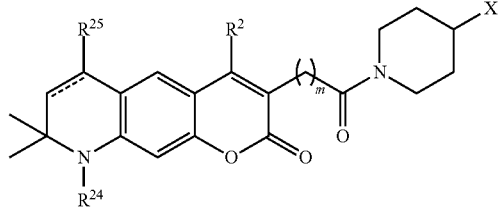

Structure 34 where
m is 0, 1, 2, 3, 4, 5, 6, 7, 8, 9 or 10;
$R^2$ is selected from a group consisting of —H or —CH$_3$;
X is —OH, —NH$_2$, —SH, —OR$^{11}$, —NHR$^{12}$, —NR$^{13}$R$^{14}$, —OC(O)R$^{15}$, —NHC(O)R$^{16}$, —SC(O)R$^{17}$, —C(O)OH, —C(O)OR$^{18}$, —C(O)NHR$^{19}$, —C(O)NR$^{20}$R$^{21}$, —N$_3$;
the dashed line represents an optional double bond;
$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from (C$_1$-C$_8$)alkyl, (C$_1$-C$_8$)substituted alkyl, —CH$_2$CH(OH)CH$_2$(OH), —CH(CH$_2$OH)$_2$, —CH$_2$CCH, —(CH$_2$CH$_2$O)$_a$—CH$_2$CH$_2$OH where a is 1, 2, 3, 4, 5, 6, 7, 8, 9 or 10, —P(NR$^{22}$R$^{23}$)OCH$_2$CH$_2$-EWG, —P(O)(O—)-Oligonucleotide, —(CH$_2$)$_b$CC-Nucleoside, —(CH$_2$)$_b$CC-[Nucleoside Triphosphate], —(CH$_2$)$_b$-Nucleoside, —(CH$_2$)$_b$-[Nucleoside Triphosphate], —(CH$_2$)$_b$NH-Nucleoside, —(CH$_2$)$_b$NH-[Nucleoside Triphosphate], —(CH$_2$)$_b$NHC(O)(CH$_2$)$_b$-Nucleoside, —(CH$_2$)$_b$NHC(O)(CH$_2$)$_b$-[Nucleoside Triphosphate], where b is 1, 2, 3, 4, 5, 6, 7, 8, 9 or 10;
EWG is an electron withdrawing group;
$R^{22}$ and $R^{23}$ are independently selected from —CH$_3$, —CH$_2$CH$_3$, —CH(CH$_3$)$_2$ or $R^{22}$ and $R^{23}$ together form a heterocycle;
$R^{24}$ is (C$_1$-C$_8$)alkyl or (C$_1$-C$_8$)substituted alkyl;

$R^{25}$ is (C$_1$-C$_8$)alkyl, (C$_1$-C$_8$)substituted alkyl or CH$_2$SO$_3$H.

Another set of compounds is represented by Structure 35, below:

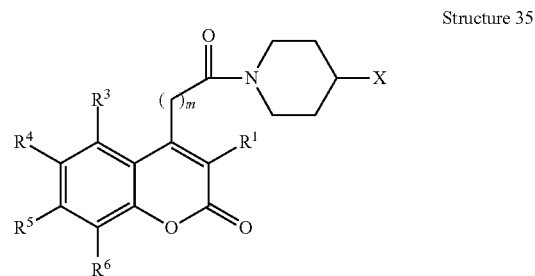

Structure 35 where
m is 0, 1, 2, 3, 4, 5, 6, 7, 8, 9 or 10;
$R^1$ is selected from a group consisting of —H or —CH$_3$;
$R^3$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where $R^7$ and $R^8$ are independently selected from H, (C$_1$-C$_8$)alkyl, or $R^7$ and $R^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or $R^3$ together with $R^4$ form a five- or six-membered carbocyclic or heterocyclic ring (e.g., piperidinyl);
$R^4$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where $R^7$ and $R^8$ are independently selected from H, (C$_1$-C$_8$)alkyl, or $R^7$ and $R^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or $R^4$ together with $R^5$ form a five- or six-membered carbocyclic or heterocyclic ring (e.g., piperidinyl);
$R^5$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where $R^7$ and $R^8$ are independently selected from H, (C$_1$-C$_8$)alkyl, or $R^7$ and $R^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or $R^5$ together with $R^6$ form a five- or six-membered carbocyclic or heterocyclic ring (e.g., piperidinyl); or $R^4$, $R^5$ and $R^6$ together form fused carbocyclic or heterocyclic ring systems having five- or six-membered rings;
$R^6$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where $R^7$ and $R^8$ are independently selected from H, (C$_1$-C$_8$)alkyl, (C$_1$-C$_8$)substituted alkyl, or $R^7$ and $R^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl;

X is —OH, —NR$_2$, —SH, —OR$^{11}$, —NHR$^{12}$, —NR$^{13}$R$^{14}$, —OC(O)R$^{15}$, —NHC(O)R$^{16}$, —SC(O)R$^{17}$, —C(O)OH, —C(O)OR$^{18}$, —C(O)NHR$^{19}$, —C(O)NR$^{20}$R$^{21}$, —N$_3$;

R$^{11}$, R$^{12}$, R$^{13}$, R$^{14}$, R$^{15}$, R$^{16}$, R$^{17}$, R$^{18}$, R$^{19}$, R$^{20}$ and R$^{21}$ are independently selected from (C$_1$-C$_8$)alkyl, (C$_1$-C$_8$)substituted alkyl, —CH$_2$CH(OH)CH$_2$(OH), —CH(CH$_2$OH)$_2$, —CH$_2$CCH, —(CH$_2$CH$_2$O)$_a$—CH$_2$CH$_2$OH where a is 1, 2, 3, 4, 5, 6, 7, 8, 9 or 10, —P(NR$^{22}$R$^{23}$)OCH$_2$CH$_2$-EWG, —P(O)(O—)-Oligonucleotide, —(CH$_2$)$_b$CC-Nucleoside, —(CH$_2$)$_b$CC-[Nucleoside Triphosphate], —(CH$_2$)$_b$-Nucleoside, —(CH$_2$)$_b$-[Nucleoside Triphosphate], —(CH$_2$)$_b$NH-Nucleoside, —(CH$_2$)$_b$NH-[Nucleoside Triphosphate], —(CH$_2$)$_b$NHC(O)(CH$_2$)$_b$-Nucleoside, —(CH$_2$)$_b$NHC(O)(CH$_2$)$_b$-[Nucleoside Triphosphate], where b is 1, 2, 3, 4, 5, 6, 7, 8, 9 or 10;

EWG is an electron withdrawing group;

R$^{22}$ and R$^{23}$ are independently selected from —CH$_3$, —CH$_2$CH$_3$, —CH(CH$_3$)$_2$ or R$^{22}$ and R$^{23}$ together form a heterocycle.

Another set of compounds is represented by Structure 36, below:

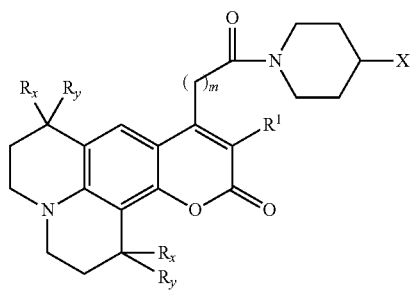

Structure 36 where m is 0, 1, 2, 3, 4, 5, 6, 7, 8, 9 or 10;

R$^1$ is selected from a group consisting of —H or —CH$_3$;

X is —OH, —NH$_2$, —SH, —OR$^{11}$, —NHR$^{12}$, —NR$^{13}$R$^{14}$, —OC(O)R$^{15}$, —NHC(O)R$^{16}$, —SC(O)R$^{17}$, —C(O)OH, —C(O)OR$^{18}$, —C(O)NHR$^{19}$, —C(O)NR$^{20}$R$^{21}$, —N$_3$;

R$^{11}$, R$^{12}$, R$^{13}$, R$^{14}$, R$^{15}$, R$^{16}$, R$^{17}$, R$^{18}$, R$^{19}$, R$^{20}$ and R$^{21}$ are independently selected from (C$_1$-C$_8$)alkyl, (C$_1$-C$_8$)substituted alkyl, —CH$_2$CH(OH)CH$_2$(OH), —CH(CH$_2$OH)$_2$, —CH$_2$CCH, —(CH$_2$CH$_2$O)$_a$—CH$_2$CH$_2$OH where a is 1, 2, 3, 4, 5, 6, 7, 8, 9 or 10, —P(NR$^{22}$R$^{23}$)OCH$_2$CH$_2$-EWG, —P(O)(O—)-Oligonucleotide, —(CH$_2$)$_b$CC-Nucleoside, —(CH$_2$)$_b$CC-[Nucleoside Triphosphate], —(CH$_2$)$_b$-Nucleoside, —(CH$_2$)$_b$-[Nucleoside Triphosphate], —(CH$_2$)$_b$NH-Nucleoside, —(CH$_2$)$_b$NH-[Nucleoside Triphosphate], —(CH$_2$)$_b$NHC(O)(CH$_2$)$_b$-Nucleoside, —(CH$_2$)$_b$NHC(O)(CH$_2$)$_6$-[Nucleoside Triphosphate], where b is 1, 2, 3, 4, 5, 6, 7, 8, 9 or 10;

EWG is an electron withdrawing group;

R$_x$ and R$_y$ are independently H or CH$_3$;

R$^{22}$ and R$^{23}$ are independently selected from —CH$_3$, —CH$_2$CH$_3$, —CH(CH$_3$)$_2$ or R$^{22}$ and R$^{23}$ together form a heterocycle.

Another set of compounds is represented by Structure 37, below:

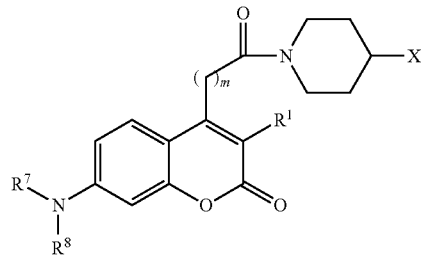

Structure 37 where m is 0, 1, 2, 3, 4, 5, 6, 7, 8, 9 or 10;

R$^1$ is selected from a group consisting of —H or —CH$_3$;

R$^7$ and R$^8$ are independently selected from H, (C$_1$-C$_8$)alkyl, (C$_1$-C$_8$)substituted alkyl, or R$^7$ and R$^8$ together form a five-, six-, or seven-membered heterocycle;

X is —OH, —NH$_2$, —SH, —OR$^{11}$, —NHR$^{12}$, —NR$^{13}$R$^{14}$, —OC(O)R$^{15}$, —NHC(O)R$^{16}$, —SC(O)R$^{17}$, —C(O)OH, —C(O)OR$^{18}$, —C(O)NHR$^{19}$, —C(O)NR$^{20}$R$^{21}$, —N$_3$;

R$^{11}$, R$^{12}$, R$^{13}$, R$^{14}$, R$^{15}$, R$^{16}$, R$^{17}$, R$^{18}$, R$^{19}$, R$^{20}$ and R$^{21}$ are independently selected from (C$_1$-C$_8$)alkyl, (C$_1$-C$_8$)substituted alkyl, —CH$_2$CH(OH)CH$_2$(OH), —CH(CH$_2$OH)$_2$, —CH$_2$CCH, —(CH$_2$CH$_2$O)$_a$—CH$_2$CH$_2$OH where a is 1, 2, 3, 4, 5, 6, 7, 8, 9 or 10, —P(NR$^{22}$R$^{23}$)OCH$_2$CH$_2$-EWG, —P(O)(O—)-Oligonucleotide, —(CH$_2$)$_b$CC-Nucleoside, —(CH$_2$)$_b$CC-[Nucleoside Triphosphate], —(CH$_2$)$_b$-Nucleoside, —(CH$_2$)$_b$-[Nucleoside Triphosphate], —(CH$_2$)$_b$NH-Nucleoside, —(CH$_2$)$_b$NH-[Nucleoside Triphosphate], —(CH$_2$)$_b$NHC(O)(CH$_2$)$_b$-Nucleoside, —(CH$_2$)$_b$NHC(O)(CH$_2$)$_b$-[Nucleoside Triphosphate], where b is 1, 2, 3, 4, 5, 6, 7, 8, 9 or 10;

EWG is an electron withdrawing group;

R$^{22}$ and R$^{23}$ are independently selected from —CH$_3$, —CH$_2$CH$_3$, —CH(CH$_3$)$_2$ or R$^{22}$ and R$^{23}$ together form a heterocycle.

Another set of compounds is represented by Structure 38, below:

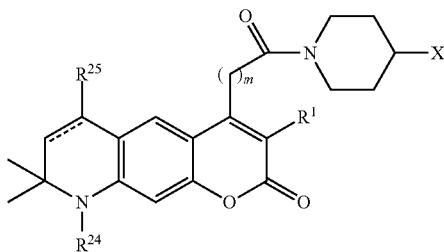

Structure 38 where m is 0, 1, 2, 3, 4, 5, 6, 7, 8, 9 or 10;

R$^1$ is selected from a group consisting of —H or —CH$_3$;

X is —OH, —NH$_2$, —SH, —OR$^{11}$, —NHR$^{12}$, —NR$^{13}$R$^{14}$, —OC(O)R$^{15}$, —NHC(O)R$^{16}$, —SC(O)R$^{17}$, —C(O)OH, —C(O)OR$^{18}$, —C(O)NHR$^{19}$, —C(O)NR$^{20}$R$^{21}$, —N$_3$;

R$^{11}$, R$^{12}$, R$^{13}$, R$^{14}$, R$^{15}$, R$^{16}$, R$^{17}$, R$^{18}$, R$^{19}$, R$^{20}$ and R$^{21}$ are independently selected from (C$_1$-C$_8$)alkyl, (C$_1$-C$_8$)substituted alkyl, —CH$_2$CH(OH)CH$_2$(OH), —CH(CH$_2$OH)$_2$, —CH$_2$CCH, —(CH$_2$CH$_2$O)$_a$—CH$_2$CH$_2$OH where a is 1, 2, 3, 4, 5, 6, 7, 8, 9 or 10, —P(NR$^{22}$R$^{23}$)OCH$_2$CH$_2$-EWG, —P(O)(O-)-Oligonucleotide, —(CH$_2$)$_b$CC-Nucleoside, —(CH$_2$)$_b$CC-[Nucleoside Triphosphate], —(CH$_2$)$_b$-Nucleoside, —(CH$_2$)$_b$-[Nucleoside Triphosphate], —(CH$_2$)$_b$NH-Nucleoside, —(CH$_2$)$_b$NH-[Nucleoside Triphosphate], —(CH$_2$)$_b$NHC(O)(CH$_2$)$_b$-Nucleoside, —(CH$_2$)$_b$NHC(O)(CH$_2$)$_b$-[Nucleoside Triphosphate], where b is 1, 2, 3, 4, 5, 6, 7, 8, 9 or 10;

EWG is an electron withdrawing group;

$R^{22}$ and $R^{23}$ are independently selected from —CH$_3$, —CH$_2$CH$_3$, —CH(CH$_3$)$_2$ or $R^{22}$ and $R^{23}$ together form a heterocycle;

$R^{24}$ is (C$_1$-C$_8$)alkyl or (C$_1$-C$_8$)substituted alkyl;

$R^{25}$ is (C$_1$-C$_8$)alkyl, (C$_1$-C$_8$)substituted alkyl or CH$_2$SO$_3$H;

the dashed line represents an optional double bond.

Another set of compounds is represented by Structure 39, below:

Structure 39

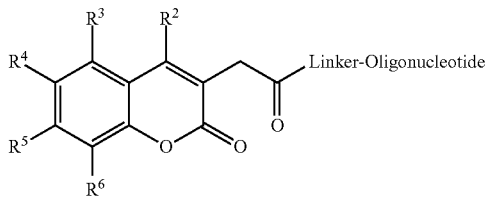

where $R^2$ is selected from a group consisting of —H, —CH$_3$, —(CH$_2$)$_m$C(O)NR$^9$R$^{10}$ where m is 0, 1, 2, 3, 4, 5, 6, 7, 8, 9 or 10, and $R^9$ and $R^{10}$ are independently selected from —H, —CH$_2$CCH, —(CH$_2$CH$_2$O)$_o$CH$_2$CCH, —CH$_2$N$_3$, —(CH$_2$CH$_2$O)$_p$CH$_2$N$_3$, —(CH$_2$)$_x$OH, —(CH$_2$CH$_2$O)$_q$CH$_2$CH$_2$OH, where o is 1, 2, 3, 4, 5, 6, 7, 8, 9 or 10, p is 1, 2, 3, 4, 5, 6, 7, 8, 9 or 10, x is 2, 3, 4, 5, 6, 7, 8, 9, or 10 and q is 1, 2, 3, 4, 5, 6, 7, 8, 9 or 10, or $R^9$ and $R^{10}$ together form a four-, five-, six- or seven-membered heterocycle (e.g., piperidinyl) substituted with a hydroxyl group;

$R^3$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where $R^7$ and $R^8$ are independently selected from H, (C$_1$-C$_8$)alkyl, or $R^7$ and $R^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl;

$R^4$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where $R^7$ and $R^8$ are independently selected from H, (C$_1$-C$_8$)alkyl, or $R^7$ and $R^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl;

$R^5$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where $R^7$ and $R^8$ are independently selected from H, (C$_1$-C$_8$)alkyl, or $R^7$ and $R^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or $R^4$, $R^5$ and $R^6$ together form fused ring systems having five- or six-membered rings;

$R^6$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where $R^7$ and $R^8$ are independently selected from H, (C$_1$-C$_8$)alkyl, or $R^7$ and $R^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl;

"Linker" is a moiety that connects the coumarin portion of the compound with the nucleoside or nucleoside triphosphate portion of the compound. Nonlimiting examples of linkers include: —NHCH$_2$CC—; —NH(CH$_2$)$_b$-, where b is 2, 3, 4, 5, 6, 7, 8, 9 or 10; —NH(CH$_2$)$_b$NH—, where b is 2, 3, 4, 5, 6, 7, 8, 9 or 10; —NHCHCH—; —NH(CH$_2$)$_b$—NHC(O)CHCH—, where b is 2, 3, 4, 5, 6, 7, 8, 9 or 10.

Another set of compounds is represented by Structure 40, below:

Structure 40

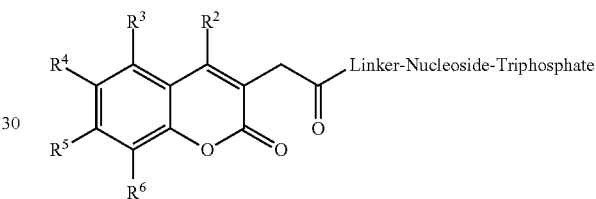

where $R^2$ is selected from a group consisting of —H, —CH$_3$, —(CH$_2$)$_m$C(O)NR$^9$R$^{10}$ where m is 0, 1, 2, 3, 4, 5, 6, 7, 8, 9 or 10, and $R^9$ and $R^{10}$ are independently selected from —H, —CH$_2$CCH, —(CH$_2$CH$_2$O)$_o$CH$_2$CCH, —CH$_2$N$_3$, —(CH$_2$CH$_2$O)$_p$CH$_2$N$_3$, —(CH$_2$)$_x$OH, —(CH$_2$CH$_2$O)$_q$CH$_2$CH$_2$OH, where o is 1, 2, 3, 4, 5, 6, 7, 8, 9 or 10, p is 1, 2, 3, 4, 5, 6, 7, 8, 9 or 10, x is 2, 3, 4, 5, 6, 7, 8, 9, or 10 and q is 1, 2, 3, 4, 5, 6, 7, 8, 9 or 10, or $R^9$ and $R^{10}$ together form a four-, five-, six- or seven-membered heterocycle (e.g., piperidinyl) substituted with a hydroxyl group;

$R^3$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where $R^7$ and $R^8$ are independently selected from H, (C$_1$-C$_8$)alkyl, or $R^7$ and $R^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl;

$R^4$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR$^7$R$^8$ where $R^7$ and $R^8$ are independently selected from H, (C$_1$-C$_8$)alkyl, or $R^7$ and $R^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl;

$R^5$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$)substituted alkylthio, (C$_1$-C$_8$)alkoxy, (C$_1$-C$_8$)substituted alkoxy, —NR⁷R⁸ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl, or $R^4$, $R^5$ and $R^6$ together form fused ring systems having five- or six-membered rings;

$R^6$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —NR⁷R⁸ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl;

"Linker" is a moiety that connects the coumarin portion of the compound with the nucleoside or nucleoside triphosphate portion of the compound. Nonlimiting examples of linkers include: —NHCH₂CC—; —NH(CH₂)$_b$—, where b is 2, 3, 4, 5, 6, 7, 8, 9 or 10; —NH(CH₂)$_b$NH—, where b is 2, 3, 4, 5, 6, 7, 8, 9 or 10; —NHCHCH—; —NH(CH₂)$_b$—NHC(O)CHCH—, where b is 2, 3, 4, 5, 6, 7, 8, 9 or 10.

"Nucleoside Triphosphate" refers to a nucleoside bound to three phosphates.

Another set of compounds is represented by Structure 41, below:

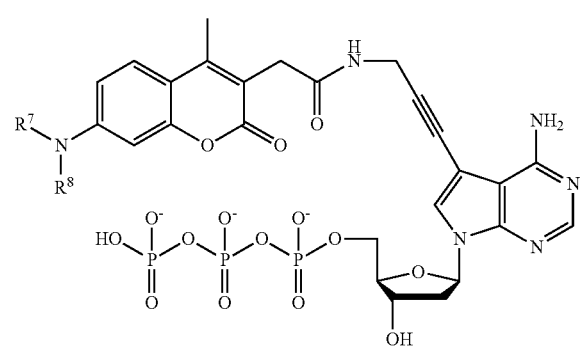

Structure 41 where $R^7$ and $R^8$ are independently selected from H, ($C_1$-$C_8$) alkyl.

Another set of compounds is represented by Structure 42, below:

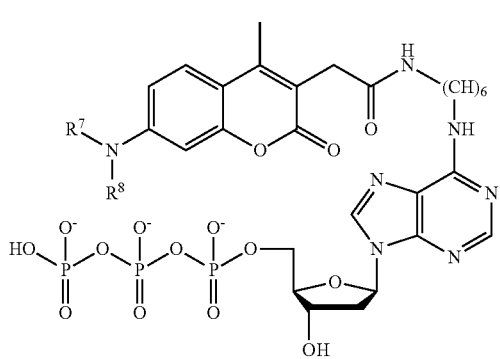

Structure 42 where $R^7$ and $R^8$ are independently selected from H, ($C_1$-$C_8$) alkyl.

Another set of compounds is represented by Structure 43, below:

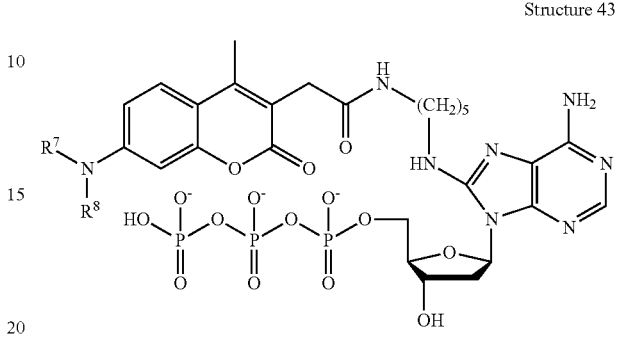

Structure 43 where $R^7$ and $R^8$ are independently selected from H, ($C_1$-$C_8$) alkyl.

Another set of compounds is represented by Structure 44, below:

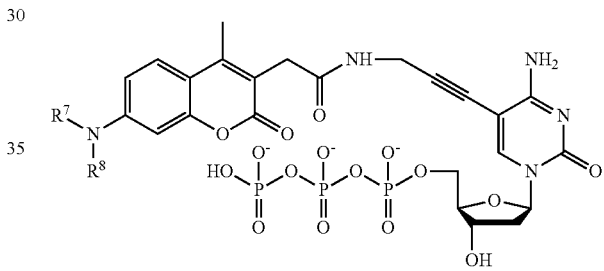

Structure 44 where $R^7$ and $R^8$ are independently selected from H, ($C_1$-$C_8$) alkyl.

Another set of compounds is represented by Structure 45, below:

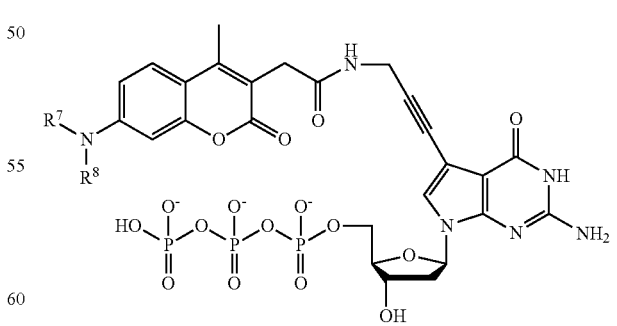

Structure 45 where $R^7$ and $R^8$ are independently selected from H, ($C_1$-$C_8$) alkyl.

Another set of compounds is represented by Structure 46, below:

Structure 46

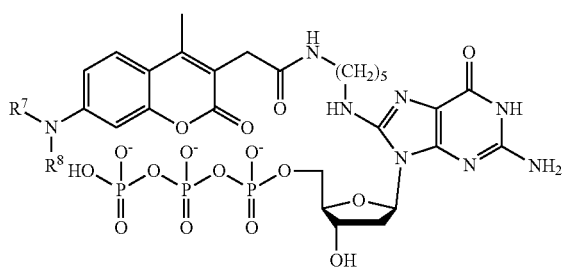

where
$R^7$ and $R^8$ are independently selected from H, $(C_1-C_8)$ alkyl.

Another set of compounds is represented by Structure 47, below:

Structure 47

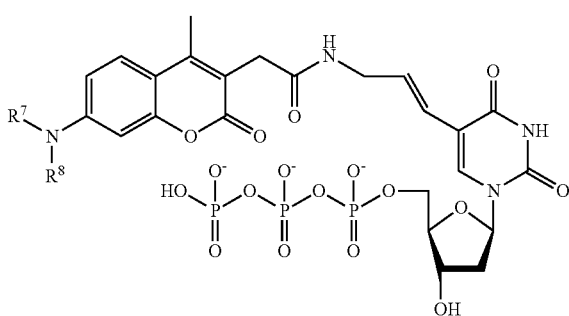

where
$R^7$ and $R^8$ are independently selected from H, $(C_1-C_8)$ alkyl.

Another set of compounds is represented by Structure 48, below:

Structure 48

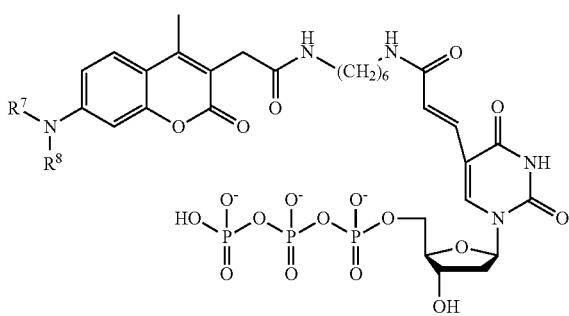

where
$R^7$ and $R^8$ are independently selected from H, $(C_1-C_8)$ alkyl.

Compound Synthesis

A. Coumarin 3-Carboxamides

Coumarin 3-carboxamides of formula 105 are prepared by reaction of a suitably substituted 4-amino-2-hydroxybenzaldehyde 101 with a dialkyl malonate 104 and a suitably substituted aminoalcohol 103 in the presence of a catalyst such as piperidine. Coumarin 3-carboxamides of formula 107 are prepared by using an aminoalcohol 106 containing a carbocyclic moiety.

Reaction Scheme 1
Preparation of Coumarin 3-Carboxamides

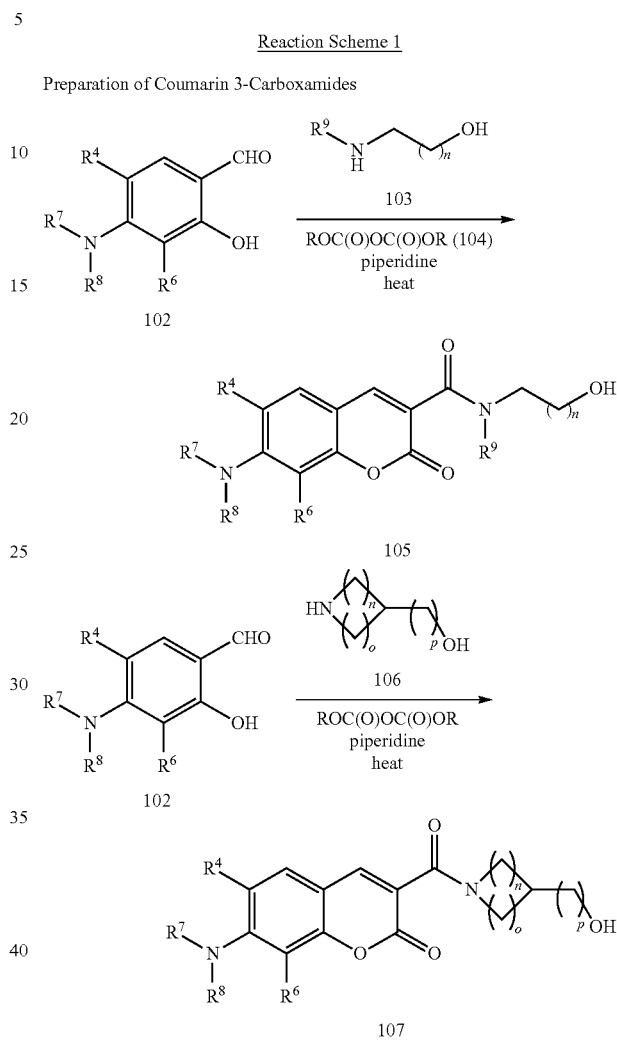

B. Coumarin 3-acetamides

Reaction of a suitably substituted 3-aminophenol 108 with an acetyl dialkyl succinate 109 in the presence of a suitable catalyst such as $ZnCl_2$, $H_2SO_4$ or TFA affords coumarin 3-acetic esters 110 and coumarin 3-acetic acids 111. The coumarin 3-acetic esters 110 are converted into coumarin 3-acetic acids 111 via hydrolysis.

Reaction Scheme 2
Preparation of Coumarin 3-Acetic Esters and Acids

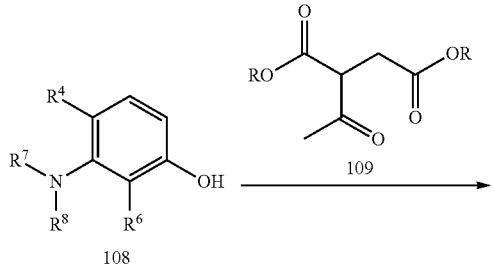

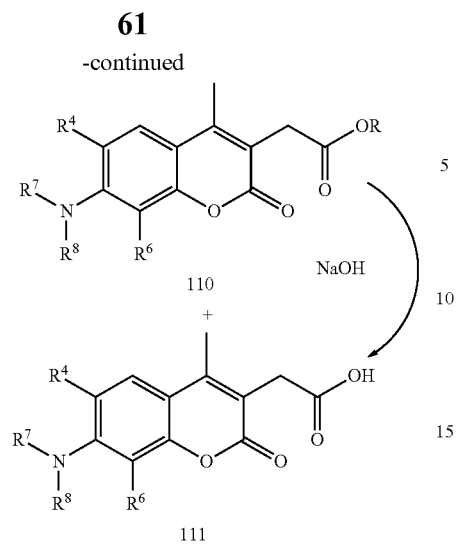

The coumarin 3-acetamides can be prepared by multiple methods starting from the coumarin 3-acetic esters 110 or the coumarin 3-acetic acids 111. In method A the coumarin 3-acetic ester 110 is reacted directly with a suitably substituted aminoalcohol 103 or aminoalcohol 106 containing a carbocyclic moiety to yield the coumarin 3-acetamide 112 or 113.

In method B the coumarin 3-acetic acid 111 is converted into the NHS ester 114 via NHS and a coupling agent such as DCC, EDCI, BOP or with a reagent to directly introduce a NHS moiety such as DSC (disuccinimidyl carbonate). The NHS ester 114 is reacted with a suitably substituted aminoalcohol 103 or aminoalcohol 106 containing a carbocyclic moiety to yield the coumarin 3-acetamide 112 or 113.

Reaction Scheme 3

Preparation of Coumarin 3-Acetamides: Method A

Reaction Scheme 4

Preparation of Coumarin 3-acetamides: Method B

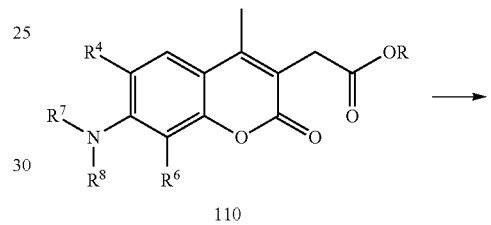

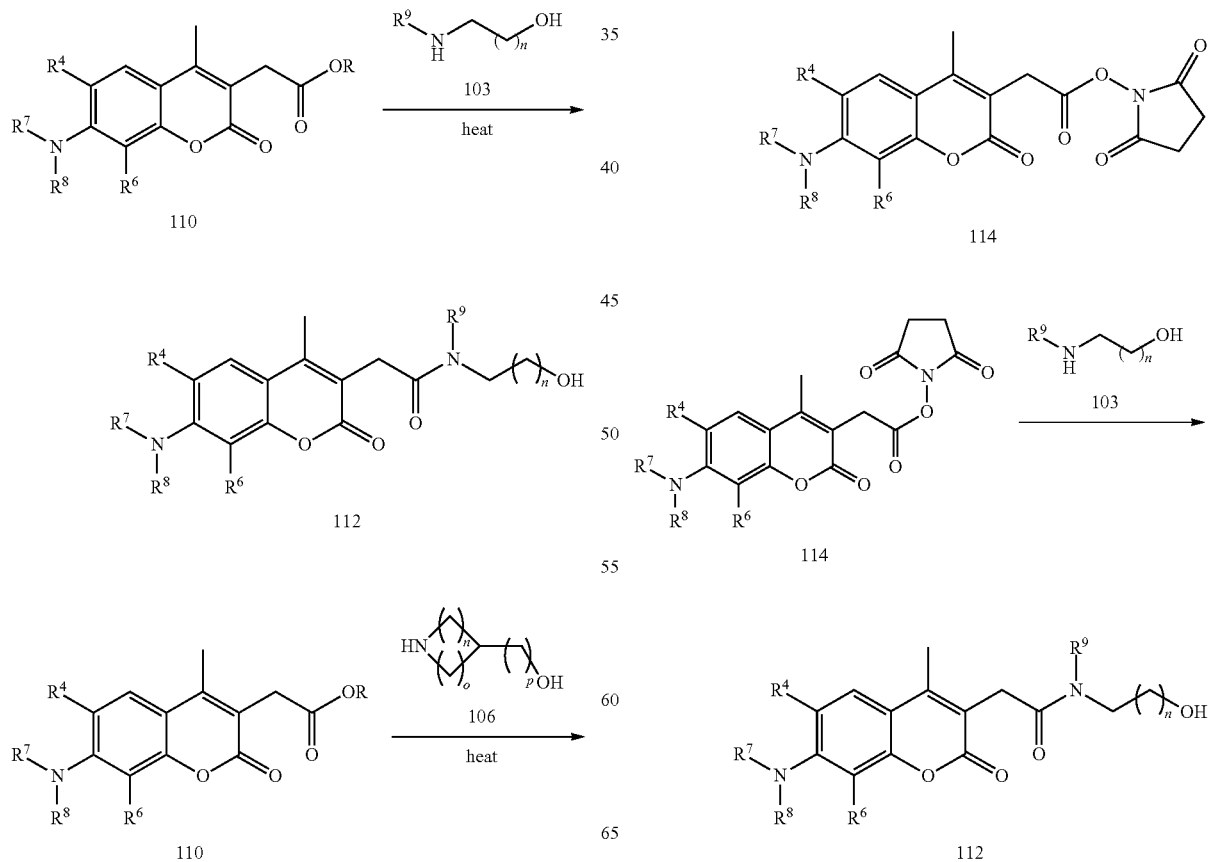

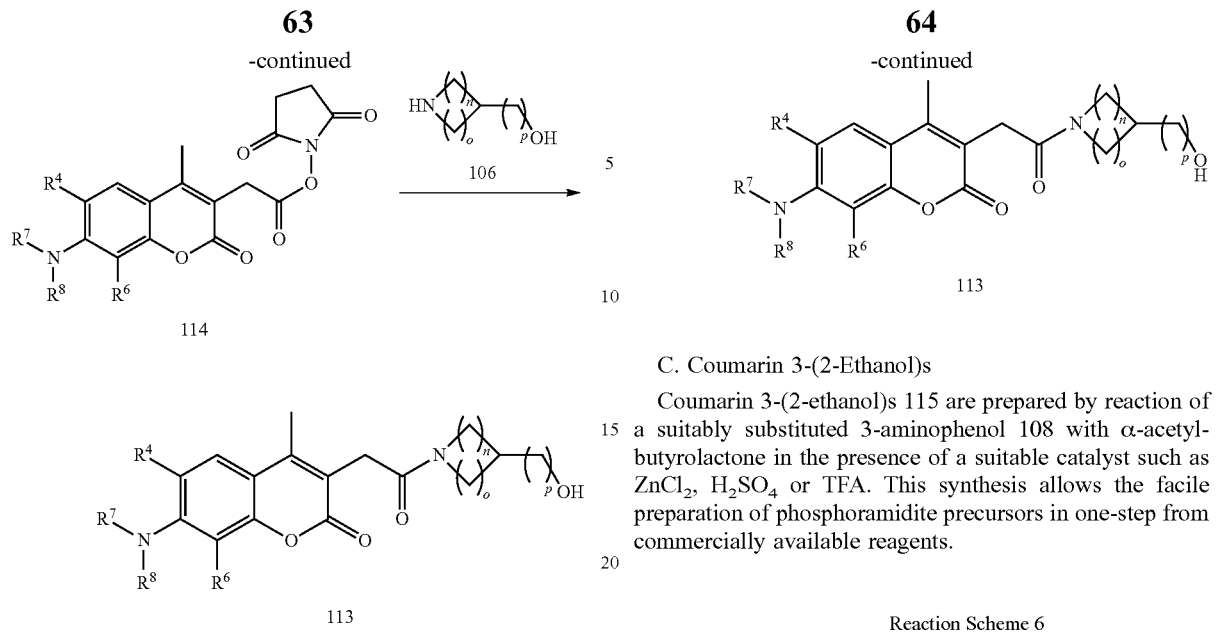

In method C the coumarin 3-acetic acid 111 is directly coupled with a suitably substituted aminoalcohol 103 or aminoalcohol 106 containing a carbocyclic moiety through the use of a coupling agent such as DCC, EDCI or BOP to yield the coumarin 3-acetamide 112 or 113.

C. Coumarin 3-(2-Ethanol)s

Coumarin 3-(2-ethanol)s 115 are prepared by reaction of a suitably substituted 3-aminophenol 108 with α-acetyl-butyrolactone in the presence of a suitable catalyst such as $ZnCl_2$, $H_2SO_4$ or TFA. This synthesis allows the facile preparation of phosphoramidite precursors in one-step from commercially available reagents.

D. Coumarin Phosphoramidites

Coumarin derivatives 105, 107, 112, 113 or 115 are converted into coumarin phosphoramidites by reaction with 3-((bis(diisopropylamino)phosphino)oxy)propanenitrile in the presence of an activator such as 1H-tetrazole or ethyl thiotetrazole.

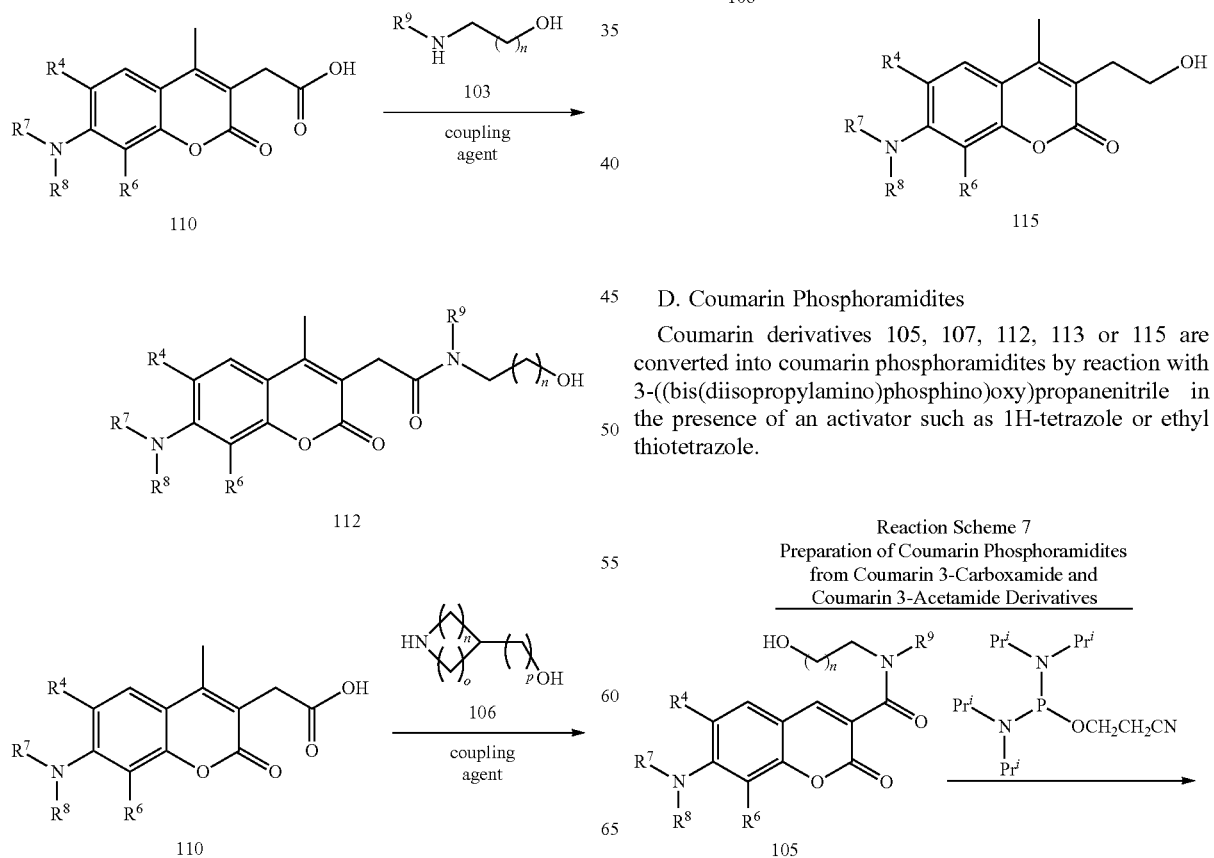

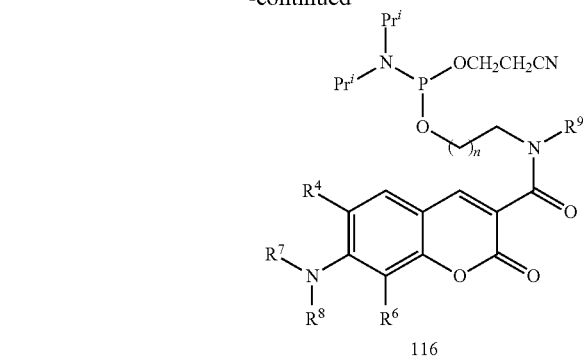

116

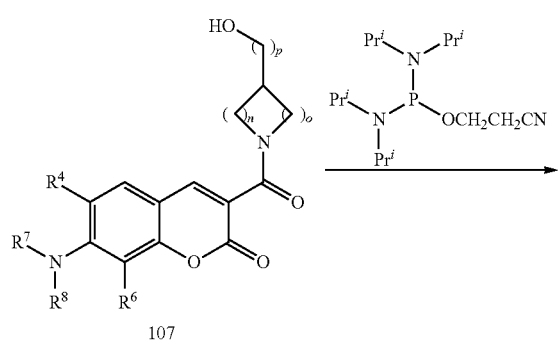

107

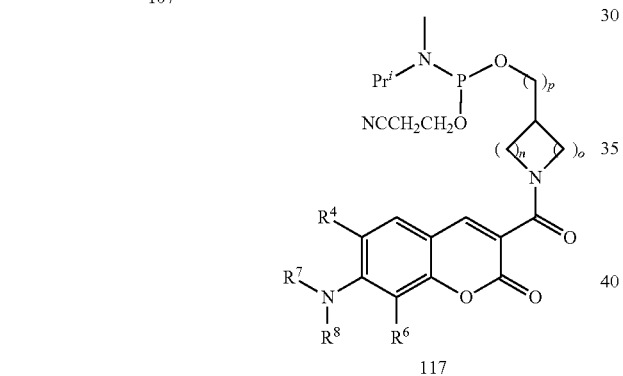

117

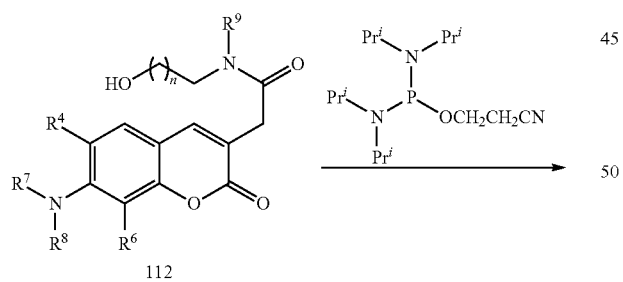

112

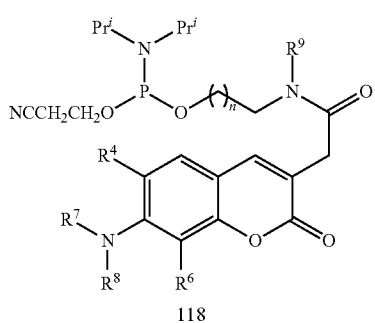

118

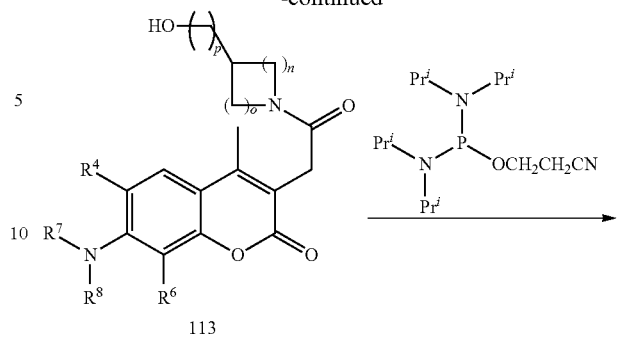

113

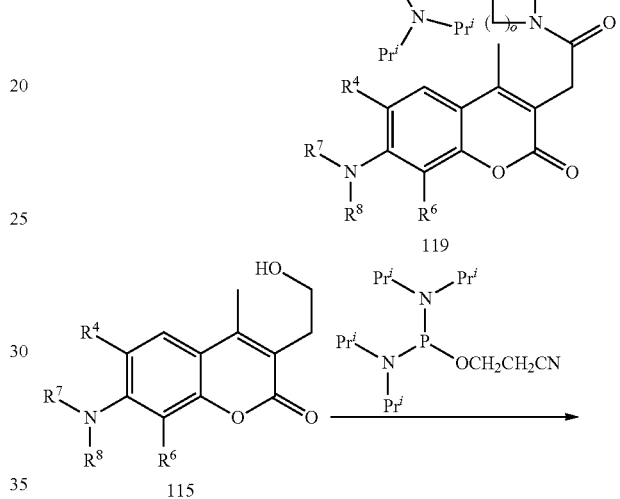

119

115

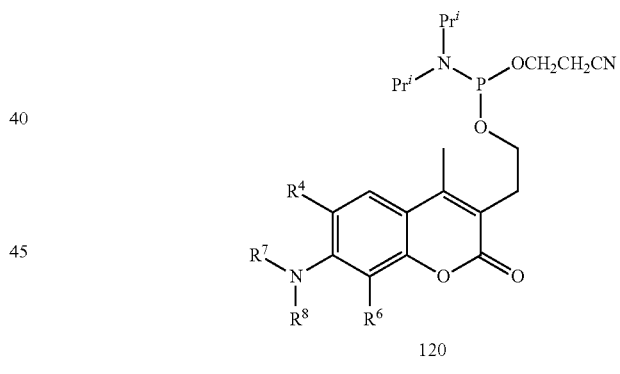

120

Another set of compounds provided by the present invention is probes. Probes include coumarin-based fluorophores—e.g., Structures 13-48 above—conjugated to, for example, a target species (e.g., receptor, enzyme, etc.) a ligand for a target species (e.g., nucleic acid, peptide, etc.), a small molecule (e.g., drug, pesticide, etc.), and the like. The probes can be used for in vitro and in vivo applications.

The fluorophores of the present invention are robust under a variety of synthetic conditions used to attach them to a carrier molecule. For example, many of the coumarin-derived fluorophores survive conditions necessary for automated synthesis of nucleic acids without undergoing any substantial degree of degradation or alteration. In contrast, many art-recognized coumarin derivates require special conditions to assemble the carrier molecule to which they are attached, or they have to be attached after the completion of the carrier molecule synthesis. The additional complexity of the synthesis of a probe increases both the duration of the synthesis and its cost.

In certain cases, when the fluorophores of the present invention are included in the automated synthesis of nucleic acids, the fluorophores are degraded or altered in less than 10.0 percent of the product nucleic acids. In other cases, the fluorophores are degraded or altered in less than 5.0 percent, 2.5 percent, 1.0 percent, or 0.5 percent of the product nucleic acids.

Another set of compounds provided by the present invention is small molecule probes. The coumarin-based fluorophores of the present invention can be used as components of small molecule probes. In a preferred design, a small molecule probe includes a fluorophore according to the present invention, or a precursor of such a molecule, and a quencher. In an exemplary embodiment, an agent, such as an enzyme cleaves the quencher, the fluorophore or both from the small molecule generating fluorescence in the system under investigation (see, for example, Zlokarnik et al., Science 279: 84-88 (1998)).

Another set of compounds provided by the present invention is nucleic acid probes. The coumarin-based fluorophores of the present invention are useful in conjunction with nucleic-acid probes, and they can be used as components of detection agents in a variety of DNA amplification/quantification strategies including, for example, 5'-nuclease assay, Strand Displacement Amplification (SDA), Nucleic Acid Sequence-Based Amplification (NASBA), Rolling Circle Amplification (RCA), as well as for direct detection of targets in solution phase or solid phase (e.g., array) assays. Furthermore, the fluorophore-derivatized nucleic acids can be used in probes of substantially any format, including, for example, format selected from molecular beacons, Scorpion Probes™, Sunrise Probes™, conformationally assisted probes, light up probes, Invader Detection probes, and TaqMan™ probes. See, for example, Cardullo, R., et al., Proc. Natl. Acad. Sci. USA, 85:8790-8794 (1988); Dexter, D. L., J. Chem. Physics, 21:836-850 (1953); Hochstrasser, R. A., et al., Biophysical Chemistry, 45:133-141 (1992); Selvin, P., Methods in Enzymology, 246:300-334 (1995); Steinberg, I., Ann. Rev. Biochem., 40:83-114 (1971); Stryer, L., Ann. Rev. Biochem., 47:819-846 (1978); Wang, G., et al., Tetrahedron Letters, 31:6493-6496 (1990); Wang, Y., et al., Anal. Chem., 67:1197-1203 (1995); Debouck, C., et al., in supplement to nature genetics, 21:48-50 (1999); Rehman, F. N., et al., Nucleic Acids Research, 27:649-655 (1999); Cooper, J. P., et al., Biochemistry, 29:9261-9268 (1990); Gibson, E. M., et al., Genome Methods, 6:995-1001 (1996); Hochstrasser, R. A., et al., Biophysical Chemistry, 45:133-141 (1992); Holland, P. M., et al., Proc Natl. Acad. Sci. USA, 88:7276-7289 (1991); Lee, L. G., et al., Nucleic Acids Rsch., 21:3761-3766 (1993); Livak, K. J., et al., PCR Methods and Applications, Cold Spring Harbor Press (1995); Vamosi, G., et al., Biophysical Journal, 71:972-994 (1996); Wittwer, C. T., et al., Biotechniques, 22:176-181 (1997); Wittwer, C. T., et al., Biotechniques, 22:130-38 (1997); Giesendorf, B. A. J., et al., Clinical Chemistry, 44:482-486 (1998); Kostrikis, L. G., et al., Science, 279:1228-1229 (1998); Matsuo, T., Biochemica et Biophysica Acta, 1379:178-184 (1998); Piatek, A. S., et al., Nature Biotechnology, 16:359-363 (1998); Schofield, P., et al., Appl. Environ. Microbiology, 63:1143-1147 (1997); Tyagi S., et al., Nature Biotechnology, 16:49-53 (1998); Tyagi, S., et al., Nature Biotechnology, 14:303-308 (1996); Nazarenko, I. A., et al., Nucleic Acids Research, 25:2516-2521 (1997); Uehara, H., et al., Biotechniques, 26:552-558 (1999); D. Whitcombe, et al., Nature Biotechnology, 17:804-807 (1999); Lyamichev, V., et al., Nature Biotechnology, 17:292 (1999); Daubendiek, et al., Nature Biotechnology, 15:273-277 (1997); Lizardi, P. M., et al., Nature Genetics, 19:225-232 (1998); Walker, G., et al., Nucleic Acids Res., 20:1691-1696 (1992); Walker, G. T., et al., Clinical Chemistry, 42:9-13 (1996); and Compton, J., Nature, 350:91-92 (1991).

A probe bearing both a quencher and a coumarin-based fluorophore according to the present invention can be used or, alternatively, one or more of the nucleic acids can be singly labeled with a quencher or fluorophore. When a nucleic acid singly labeled with a fluorophore according to the present invention is the probe, the interaction between the first and second nucleic acids can be detected by observing the interaction between the fluorophore and the nucleic acid or, more preferably, the quenching of the fluorescence of the fluorophore by the quencher attached to the second nucleic acid.

In addition to their general utility in probes designed to investigate nucleic acid amplification, detection and quantification, the present fluorophores can be used in substantially any nucleic acid probe format now known or later discovered. For example, the coumarin-based fluorophores of the invention can be incorporated into probe motifs, such as Taqman™ probes (Held et al., Genome Res. 6: 986-994 (1996), Holland et al., Proc. Nat. Acad. Sci. USA 88: 7276-7280 (1991), Lee et al., Nucleic Acids Res. 21: 3761-3766 (1993)), molecular beacons (Tyagi et al., Nature Biotechnology 14:303-308 (1996), Jayasena et al., U.S. Pat. No. 5,989,823, issued Nov. 23, 1999)) scorpion probes (Whitcomb et al., Nature Biotechnology 17: 804-807 (1999)), sunrise probes (Nazarenko et al., Nucleic Acids Res. 25: 2516-2521 (1997)), conformationally assisted probes (Cook, R., U.S. Provisional Application 60/138,376, filed Jun. 9, 1999), peptide nucleic acid (PNA)-based light up probes (Kubista et al., WO 97/45539, December 1997), double-strand specific DNA dyes (Higuchi et al, Bio/Technology 10: 413-417 (1992), Wittwer et al, BioTechniques 22: 130-138 (1997)) and the like. These and other probe motifs with which the present quenchers can be used are reviewed in NONISOTOPIC DNA PROBE TECHNIQUES, Academic Press, Inc. 1992.

The nucleic acids for use in the probes of the invention can be any suitable size, and are preferably in the range of from about 10 to about 100 nucleotides, more preferably from about 10 to about 80 nucleotides and more preferably still, from about 20 to about 40 nucleotides. The precise sequence and length of a nucleic acid probe of the invention depends in part on the nature of the target polynucleotide to which it binds. The binding location and length may be varied to achieve appropriate annealing and melting properties for a particular embodiment. Guidance for making such design choices can be found in many art-recognized references.

Preferably, the 3'-terminal nucleotide of the nucleic acid probe is blocked or rendered incapable of extension by a nucleic acid polymerase. Such blocking is conveniently carried out by the attachment of a donor or acceptor moiety to the terminal 3'-position of the nucleic acid probe, either directly or by a linking moiety.

The nucleic acid can comprise DNA, RNA or chimeric mixtures or derivatives or modified versions thereof. Both the probe and target nucleic acid can be present as a single strand, duplex, triplex, etc. Moreover, the nucleic acid can be modified at the base moiety, sugar moiety, or phosphate backbone with other groups such as radioactive labels, minor groove binders, intercalating agents, donor and/or acceptor moieties and the like.

For example, the nucleic acid can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N.sup.2-carboxypropyl) uracil, (acp3)w, nitroindole, and 2,6-diaminopurine.

In another embodiment, the nucleic acid comprises at least one modified sugar moiety selected from the group including, but not limited to, arabinose, 2-fluoroarabinose, xylulose, and hexose.

In yet another embodiment, the nucleic acid comprises at least one modified phosphate backbone selected from the group including, but not limited to, a peptide nucleic acid hybrid, a phosphorothioate, a phosphorodithioate, a phosphoramidothioate, a phosphoramidate, a phosphordiamidate, a methylphosphonate, an alkyl phosphotriester, and a formacetal or analog thereof Phosphodiester linked nucleic acids of the invention can be synthesized by standard methods known in the art, e.g. by use of an automated DNA synthesizer (such as are commercially available from P.E. Biosystems, etc.) using commercially available amidite chemistries. Nucleic acids bearing modified phosphodiester linking groups can be synthesized by methods known in the art. For example, phosphorothioate nucleic acids may be synthesized by the method of Stein et al. (Nucl. Acids Res. 16:3209 (1988)), methylphosphonate nucleic acids can be prepared by use of controlled pore glass polymer supports (Sarin et al., Proc. Natl. Acad. Sci. U.S.A. 85:7448-7451 (1988)). Other methods of synthesizing both phosphodiester- and modified phosphodiester-linked nucleic acids will be apparent to those of skill in the art.

Nucleic acid probes of the invention can be synthesized by a number of approaches, e.g., Ozaki et al., Nucleic Acids Research, 20: 5205-5214 (1992); Agrawal et al., Nucleic Acids Research, 18: 5419-5423 (1990); or the like. The nucleic acid probes of the invention are conveniently synthesized on an automated DNA synthesizer, e.g., a P.E. Biosystems, Inc. (Foster City, Calif.) model 392 or 394 DNA/RNA Synthesizer, using standard chemistries, such as phosphoramidite chemistry (see, for example, disclosed in the following references, Beaucage et al., Tetrahedron, 48: 2223-2311 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679. Alternative chemistries resulting in non-natural backbone groups, such as phosphorothioate, phosphoramidate, and the like, can also be employed.

When the nucleic acids are synthesized utilizing an automated nucleic acid synthesizer, the donor and acceptor moieties are preferably introduced during automated synthesis. Alternatively, one or more of these moieties can be introduced either before or after the automated synthesis procedure has commenced. For example, donor and/or acceptor groups can be introduced at the 3'-terminus using a solid support modified with the desired group(s). Additionally, donor and/or acceptor groups can be introduced at the 5'-terminus by, for example a derivative of the group that includes a phosphoramidite. In another exemplary embodiment, one or more of the donor and/or acceptor groups is introduced after the automated synthesis is complete.

In the dual labeled probes, the fluorophore is preferably separated from the quencher by at least about 10 nucleotides, and more preferably by at least about 15 nucleotides. The donor moiety is preferably attached to either the 3'- or 5'-terminal nucleotides of the probe. The fluorophore is also preferably attached to either the 3'- or 5'-terminal nucleotides of the probe. More preferably, the donor and acceptor moieties are attached to the 3'- and 5'- or 5'- and 3'-terminal nucleotides of the probe, respectively, although internal placement is also useful.

Once the desired nucleic acid is synthesized, it is preferably cleaved from the solid support on which it was synthesized and treated, by methods known in the art, to remove any protecting groups present (e.g., 60° C., 5 h, concentrated ammonia). In those embodiments in which a base-sensitive group is attached to the nucleic acids (e.g., TAMRA), the deprotection will preferably use milder conditions (e.g., tert-butylamine/water 1:3, 8 hours, 70° C.). Deprotection under these conditions is facilitated by the use of quick deprotect amidites (e.g., dC-acetyl, dG-dmf).

Following cleavage from the support and deprotection, the nucleic acid is purified by any method known in the art, including chromatography, extraction and gel purification. In a preferred embodiment, the nucleic acid is purified using HPLC. The concentration and purity of the isolated nucleic acid is preferably determined by measuring the optical density at 260 nm in a spectrophotometer.

Another set of compounds provided by the present invention is peptide probes. Peptides, proteins and peptide nucleic acids that are labeled with a fluorophore of the present invention and a quencher can be used in both in vivo and in vitro enzymatic assays.

A set of materials provided by the present invention is solid support immobilized, coumarin-based fluorophores. The fluorophores of the present invention can be immobilized on substantially any polymer, biomolecule, and solid or semi-solid material having any useful configuration. Moreover, any conjugate comprising one or more fluorophores can be similarly immobilized. When the support is a solid or semi-solid, examples of preferred types of supports for immobilization of the nucleic acid probe include, but are not limited to, controlled pore glass, glass plates, polystyrene, avidin coated polystyrene beads, cellulose, nylon, acrylamide gel and activated dextran. These solid supports are preferred because of their chemical stability, ease of functionalization and well-defined surface area. Solid supports such as, controlled pore glass (CPG, 500 angstroms, 1000 angstroms) and non-swelling high cross-linked polystyrene (1000 angstroms) are particularly preferred.

According to the present invention, the surface of a solid support is functionalized with a fluorophore of the invention or a species including a fluorophore of the invention. For clarity of illustration, the following discussion focuses on attaching a reactive fluorophore to a solid support. The following discussion is also broadly relevant to attaching a species that includes within its structure a reactive fluorophore to a solid support, and the attachment of such species and reactive fluorophores to other molecules and structures.

The fluorophores are preferably attached to a solid support by forming a bond between a reactive group on the fluorophore and a reactive group on the surface of the solid support or a linker attached to the solid support, thereby derivatizing the solid support with one or more fluorophores. Nonlimiting examples of reactive groups include: amines, hydroxyl groups, carboxylic acids, carboxylic acid derivatives, alkenes, sulfhydryls, siloxanes, etc.

A set of compounds provided by the present invention is nucleic acid capture probes. In one embodiment, an immobilized nucleic acid comprising a coumarin-based fluorophore according to the present invention is used as a capture probe. The nucleic acid probe can be attached directly to a solid support, for example by attachment of the 3'- or 5'-terminal nucleotide of the probe to the solid support. More preferably, however, the probe is attached to the solid support by a linker. The linker serves to distance the probe from the solid support. The linker is most preferably from about 5 to about 30 atoms in length, more preferably from about 10 to about 50 atoms in length.

In yet another preferred embodiment, the solid support is also used as the synthesis support in preparing the probe. The length and chemical stability of the linker between the solid support and the first 3'-unit of nucleic acid play an important role in efficient synthesis and hybridization of support bound nucleic acids. The linker arm should be sufficiently long so that a high yield (>97%) can be achieved during automated synthesis. The required length of the linker will depend on the particular solid support used. For example, a six atom linker is generally sufficient to achieve a >97% yield during automated synthesis of nucleic acids when high cross-linked polystyrene is used as the solid support. The linker arm is preferably at least 20 atoms long in order to attain a high yield (>97%) during automated synthesis when CPG is used as the solid support.

Hybridization of a probe immobilized on a solid support generally requires that the probe be separated from the solid support by at least 30 atoms, more preferably at least 50 atoms. In order to achieve this separation, the linker generally includes a spacer positioned between the linker and the 3'-terminus. For nucleic acid synthesis, the linker arm is usually attached to the 3'-OH of the 3'-terminus by an ester linkage which can be cleaved with basic reagents to free the nucleic acid from the solid support.

A wide variety of linkers are known in the art, which may be used to attach the nucleic acid probe to the solid support. The linker may be formed of any compound, which does not significantly interfere with the hybridization of the target sequence to the probe attached to the solid support. The linker may be formed of, for example, a homopolymeric nucleic acid, which can be readily added on to the linker by automated synthesis. Alternatively, polymers such as functionalized polyethylene glycol can be used as the linker. Such polymers are presently preferred over homopolymeric nucleic acids because they do not significantly interfere with the hybridization of probe to the target nucleic acid. Polyethylene glycol is particularly preferred because it is commercially available, soluble in both organic and aqueous media, easy to functionalize, and completely stable under nucleic acid synthesis and post-synthesis conditions.

The linkages between the solid support, the linker and the probe are preferably not cleaved during synthesis or removal of base protecting groups under basic conditions at high temperature. These linkages can, however, be selected from groups that are cleavable under a variety of conditions. Examples of presently preferred linkages include carbamate, ester and amide linkages.

A set of materials provided by the present invention is acrylamide-immobilized probes. In another preferred embodiment, a species is within a matrix, such as an acrylamide matrix and the species bears a coumarin-based fluorophore according to the present invention, or the presence of the immobilized species is ascertained using a probe bearing a fluorophore. In a preferred embodiment, the immobilization is accomplished in conjunction with the "acrydite" process invented and commercialized by Mosaic Technologies (Cambridge, Mass., see, Rehman et al., Nucleic Acids Research, 27: 649-655 (1999)). The acrydite method allows immobilization of alkene labeled capture probes within a polymerized polyacrylamide network. When target mixes are run past the immobilized probe band under electrophoresis conditions, the target nucleic acid is captured substantially quantitatively. However, detection of this event currently requires a second probe. In one embodiment, probes bearing a fluorophore, and/or a quencher, are immobilized in an acrylamide matrix and subsequently contacted with the target mix. By using fluorescent probes as capture probes, signals from target mixes can be directly detected in real time.

A collection of compounds provided by the present invention is a microarray. The microarrays include immobilized, coumarin-based fluorophores and compounds (e.g., peptides, nucleic acids, bioactive agents, etc.) functionalized with coumarin-based fluorophores. Moreover, the invention provides methods of interrogating microarrays using probes that are functionalized with fluorophores. The immobilized species and the probes are selected from substantially any type of molecule, including, but not limited to, small molecules, peptides, enzymes nucleic acids and the like.

Nucleic acid microarrays consisting of a multitude of immobilized nucleic acids are important tools for the generation of genomic information, see, Debouck et al., in supplement to Nature Genetics, 21:48-50 (1999). The discussion that follows focuses on the use of fluorophores according to the present invention in conjunction with nucleic acid microarrays. This focus is intended to be illustrative and does not limit the scope of materials with which this aspect of the present invention can be practiced.

In another preferred embodiment, the compounds of the present invention are utilized in a microarray format. The fluorophores, or species bearing fluorophores can themselves be components of a microarray or, alternatively they can be utilized as a tool to screen components of a microarray.

One method for making ordered arrays of coumarin-based probes on a substrate is a "dot blot" approach. In this method, a vacuum manifold transfers a plurality, e.g., 96, aqueous samples of probes from 3 millimeter diameter wells to a substrate. The probe is immobilized on the porous membrane by baking the membrane or exposing it to UV radiation. A common variant of this procedure is a "slot-blot" method in which the wells have highly-elongated oval shapes.

Another technique employed for making ordered arrays of probes uses an array of pins dipped into the wells, e.g., the 96 wells of a microtiter plate, for transferring an array of samples to a substrate, such as a porous membrane. One array includes pins that are designed to spot a membrane in a staggered fashion, for creating an array of 9216 spots in a 22×22 cm area. See, Lehrach, et al., HYBRIDIZATION FINGERPRINTING IN GENOME MAPPING AND SEQUENCING, GENOME ANALYSIS, Vol. 1, Davies et al, Eds., Cold Springs Harbor Press, pp. 39-81 (1990).

An alternate method of creating ordered arrays of probes is analogous to that described by Pirrung et al. (U.S. Pat. No. 5,143,854, issued 1992), and also by Fodor et al., (Science, 251: 767-773 (1991)). This method involves synthesizing different probes at different discrete regions of a particle or other substrate. This method is preferably used with relatively short probe molecules, e.g., less than 20 bases. A related method has been described by Southern et al. (Genomics, 13: 1008-1017 (1992)).

Khrapko, et al., DNA Sequence, 1: 375-388 (1991) describes a method of making a nucleic acid matrix by spotting DNA onto a thin layer of polyacrylamide. The spotting is done manually with a micropipette.

The substrate can also be patterned using techniques such as photolithography (Kleinfield et al., J. Neurosci. 8:4098-120 (1998)), photoetching, chemical etching and microcontact printing (Kumar et al., Langmuir 10:1498-511 (1994)). Other techniques for forming patterns on a substrate will be readily apparent to those of skill in the art.

The size and complexity of the pattern on the substrate is limited only by the resolution of the technique utilized and the purpose for which the pattern is intended. For example, using microcontact printing, features as small as 200 nm are layered onto a substrate. See, Xia, Y., J. Am. Chem. Soc. 117:3274-75 (1995). Similarly, using photolithography, patterns with features as small as 1 µm are produced. See, Hickman et al., J. Vac. Sci. Technol. 12:607-16 (1994). Patterns which are useful in the present invention include those which include features such as wells, enclosures, partitions, recesses, inlets, outlets, channels, troughs, diffraction gratings and the like.

In a presently preferred embodiment, the patterning is used to produce a substrate having a plurality of adjacent wells, indentations or holes to contain the probes. In general, each of these substrate features is isolated from the other wells by a raised wall or partition and the wells do not readily fluidically communicate. Thus, a particle, reagent or other substance, placed in a particular well remains substantially confined to that well. In another preferred embodiment, the patterning allows the creation of channels through the device whereby an analyte or other substance can enter and/or exit the device.

In another embodiment, the probes are immobilized by "printing" them directly onto a substrate or, alternatively, a "lift off" technique can be utilized. In the lift off technique, a patterned resist is laid onto the substrate, and a probe is laid down in those areas not covered by the resist and the resist is subsequently removed. Resists appropriate for use with the substrates of the present invention are known to those of skill in the art. See, for example, Kleinfield et al., J. Neurosci. 8:4098-120 (1998). Following removal of the photoresist, a second probe, having a structure different from the first probe can be bonded to the substrate on those areas initially covered by the resist. Using this technique, substrates with patterns of probes having different characteristics can be produced. Similar substrate configurations are accessible through microprinting a layer with the desired characteristics directly onto the substrate. See, Mrkish et al. Ann. Rev. Biophys. Biomol. Struct. 25:55-78 (1996).

Another set of materials provided by the present invention is CPG-immobilized compounds, where the compounds include a coumarin-based moiety (coumarin-CPG compound). In one case the coumarin-CPG compound is of Structure 150.

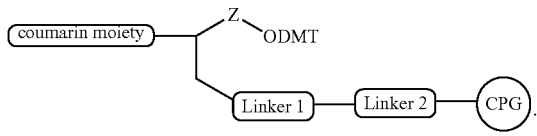

Structure 150 wherein the coumarin moiety is of Structure 151.

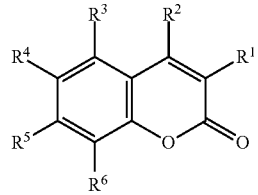

Structure 151

With respect to Structure 151, $R^1$ is selected from a group consisting of —H, —CH$_3$, —(CH$_2$)$_m$C(O)NR$^9$R$^{10}$ where m is 0, 1, 2, 3, 4, 5, 6, 7, 8, 9 or 10, and $R^9$ and $R^{10}$ are independently selected from a radical, —H, —CH$_2$CCH, —(CH$_2$CH$_2$O)$_o$CH$_2$CCH, —CH$_2$N$_3$, —(CH$_2$CH$_2$O)$_p$CH$_2$N$_3$, —(CH$_2$)$_x$OH, —(CH$_2$CH$_2$O)$_q$CH$_2$CH$_2$OH, where o is 1, 2, 3, 4, 5, 6, 7, 8, 9 or 10, p is 1, 2, 3, 4, 5, 6, 7, 8, 9 or 10, x is 2, 3, 4, 5, 6, 7, 8, 9, or 10 and q is 1, 2, 3, 4, 5, 6, 7, 8, 9 or 10, or $R^9$ and $R^{10}$ together form a five-, six- or seven-membered heterocycle (e.g., piperidinyl) substituted with a hydroxyl group;

$R^2$ is selected from a group consisting of —H, —CH$_3$, —(CH$_2$)$_m$C(O)NR$^9$R$^{10}$ where m is 0, 1, 2, 3, 4, 5, 6, 7, 8, 9 or 10, and $R^9$ and $R^{10}$ are independently selected from a radical, —H, —CH$_2$CCH, —(CH$_2$CH$_2$O)$_o$CH$_2$CCH, —CH$_2$N$_3$, —(CH$_2$CH$_2$O)$_p$CH$_2$N$_3$, —(CH$_2$)$_x$OH, —(CH$_2$CH$_2$O)$_q$CH$_2$CH$_2$OH, where o is 1, 2, 3, 4, 5, 6, 7, 8, 9 or 10, p is 1, 2, 3, 4, 5, 6, 7, 8, 9 or 10, x is 2, 3, 4, 5, 6, 7, 8, 9, or 10 and q is 1, 2, 3, 4, 5, 6, 7, 8, 9 or 10, or $R^9$ and $R^{10}$ together form a five-, six- or seven-membered heterocycle (e.g., piperidinyl) substituted with a hydroxyl group;

$R^3$ is selected from a group consisting of —H, -halogen, —CF$_3$, —OH, —NH$_2$, —CCH, —CN, —NO$_2$, (C$_1$-C$_8$) alkyl, (C$_1$-C$_8$)substituted alkyl, (C$_1$-C$_8$)alkylthio, (C$_1$-C$_8$) substituted alkylthio, (C$_1$-C$_8$)alkoxy, (C$_1$-C$_8$)substituted alkoxy, —NR$^7$R$^8$ where $R^7$ and $R^8$ are independently selected from H, (C$_1$-C$_8$)alkyl, or $R^7$ and $R^8$ together form a four-, five-, six-, or seven-membered heterocycle, (C$_1$-C$_8$) heteroalkyl, (C$_1$-C$_8$)substituted heteroalkyl, aryl, substituted aryl, heteroaryl, substituted heteroaryl;

$R^4$ is selected from a group consisting of —H, -halogen, —CF$_3$, —OH, —NH$_2$, —CCH, —CN, —NO$_2$, (C$_1$-C$_8$) alkyl, (C$_1$-C$_8$)substituted alkyl, (C$_1$-C$_8$)alkylthio, (C$_1$-C$_8$) substituted alkylthio, (C$_1$-C$_8$)alkoxy, (C$_1$-C$_8$)substituted alkoxy, —NR$^7$R$^8$ where $R^7$ and $R^8$ are independently selected from H, (C$_1$-C$_8$)alkyl, or $R^7$ and $R^8$ together form a four-, five-, six-, or seven-membered heterocycle, (C$_1$-C$_8$) heteroalkyl, (C$_1$-C$_8$)substituted heteroalkyl, aryl, substituted aryl, heteroaryl, substituted heteroaryl;

$R^5$ is selected from a group consisting of —H, -halogen, —CF$_3$, —OH, —NH$_2$, —CCH, —CN, —NO$_2$, (C$_1$-C$_8$) alkyl, (C$_1$-C$_8$)substituted alkyl, (C$_1$-C$_8$)alkylthio, (C$_1$-C$_8$) substituted alkylthio, (C$_1$-C$_8$)alkoxy, (C$_1$-C$_8$)substituted alkoxy, —NR$^7$R$^8$ where $R^7$ and $R^8$ are independently selected from H, (C$_1$-C$_8$)alkyl, or $R^7$ and $R^8$ together form a four-, five-, six-, or seven-membered heterocycle, $(C_1-C_8)$ heteroalkyl, $(C_1-C_8)$substituted heteroalkyl, aryl, substituted aryl, heteroaryl, substituted heteroaryl, or $R^4$, $R^5$ and $R^6$ together form fused ring systems having five- or six-membered rings;

$R^6$ is selected from a group consisting of —H, -halogen, —$CF_3$, —OH, —$NH_2$, —CCH, —CN, —$NO_2$, $(C_1-C_8)$ alkyl, $(C_1-C_8)$substituted alkyl, $(C_1-C_8)$alkylthio, $(C_1-C_8)$ substituted alkylthio, $(C_1-C_8)$alkoxy, $(C_1-C_8)$substituted alkoxy, —$NR^7R^8$ where $R^7$ and $R^8$ are independently selected from H, $(C_1-C_8)$alkyl, or $R^7$ and $R^8$ together form a four-, five-, six-, or seven-membered heterocycle, $(C_1-C_8)$ heteroalkyl, $(C_1-C_8)$substituted heteroalkyl, aryl, substituted aryl, heteroaryl, substituted heteroaryl.

The coumarin moiety of Structure 150 is attached to the coumarin-CPG compound through either $R^1$ or $R^2$; Z is $(CH_2)_x$, wherein x is 1, 2, 3, 4, 5, 6, 7, 8, 9 or 10. Linkers such as Linker 1 and Linker 2 may be of any suitable structure. Oftentimes, Linker 1 is selected from $OC(O)(CH_2)_yO(CH_2)_z(CO)$, $NHC(O)(CH_2)_yO(CH_2)_z(CO)$, wherein y is 1, 2, 3, 4, 5, 6, 7, 8, 9 or 10, and wherein z is 1, 2, 3, 4, 5, 6, 7, 8, 9 or 10, and Linker 2 is selected from $NH(CH_2)_a$ and $O(CH_2)_a$, wherein a is 1, 2, 3, 4, 5, 6, 7, 8, 9 or 10.

In certain cases, the coumarin moiety of Structure 150 is of Structure 152.

Structure 152

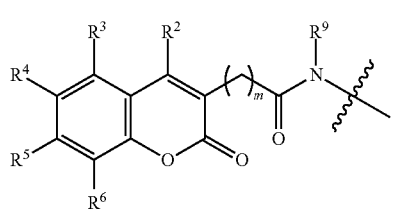

With respect to Structure 152, m is 0, 1, 2, 3, 4, 5, 6, 7, 8, 9 or 10, and $R^2$ is H or $CH_3$.

$R^3$ is selected from a group consisting of —H, -halogen, —$CF_3$, —OH, —$NH_2$, —CCH, —CN, —$NO_2$, $(C_1-C_8)$ alkyl, $(C_1-C_8)$substituted alkyl, $(C_1-C_8)$alkylthio, $(C_1-C_8)$ substituted alkylthio, $(C_1-C_8)$alkoxy, $(C_1-C_8)$substituted alkoxy, —$NR^7R^8$ where $R^7$ and $R^8$ are independently selected from H, $(C_1-C_8)$alkyl, or $R^7$ and $R^8$ together form a four-, five-, six-, or seven-membered heterocycle, $(C_1-C_8)$ heteroalkyl, $(C_1-C_8)$substituted heteroalkyl, aryl, substituted aryl, heteroaryl, substituted heteroaryl;

$R^4$ is selected from a group consisting of —H, -halogen, —$CF_3$, —OH, —$NH_2$, —CCH, —CN, —$NO_2$, $(C_1-C_8)$ alkyl, $(C_1-C_8)$substituted alkyl, $(C_1-C_8)$alkylthio, $(C_1-C_8)$ substituted alkylthio, $(C_1-C_8)$alkoxy, $(C_1-C_8)$substituted alkoxy, —$NR^7R^8$ where $R^7$ and $R^8$ are independently selected from H, $(C_1-C_8)$alkyl, or $R^7$ and $R^8$ together form a four-, five-, six-, or seven-membered heterocycle, $(C_1-C_8)$ heteroalkyl, $(C_1-C_8)$substituted heteroalkyl, aryl, substituted aryl, heteroaryl, substituted heteroaryl;

$R^5$ is selected from a group consisting of —H, -halogen, —$CF_3$, —OH, —$NH_2$, —CCH, —CN, —$NO_2$, $(C_1-C_8)$ alkyl, $(C_1-C_8)$substituted alkyl, $(C_1-C_8)$alkylthio, $(C_1-C_8)$ substituted alkylthio, $(C_1-C_8)$alkoxy, $(C_1-C_8)$substituted alkoxy, —$NR^7R^8$ where $R^7$ and $R^8$ are independently selected from H, $(C_1-C_8)$alkyl, or $R^7$ and $R^8$ together form a four-, five-, six-, or seven-membered heterocycle, $(C_1-C_8)$ heteroalkyl, $(C_1-C_8)$substituted heteroalkyl, aryl, substituted aryl, heteroaryl, substituted heteroaryl, or $R^4$, $R^5$ and $R^6$ together form fused ring systems having five- or six-membered rings;

$R^6$ is selected from a group consisting of —H, -halogen, —$CF_3$, —OH, —$NH_2$, —CCH, —CN, —$NO_2$, $(C_1-C_8)$ alkyl, $(C_1-C_8)$substituted alkyl, $(C_1-C_8)$alkylthio, $(C_1-C_8)$ substituted alkylthio, $(C_1-C_8)$alkoxy, $(C_1-C_8)$substituted alkoxy, —$NR^7R^8$ where $R^7$ and $R^8$ are independently selected from H, $(C_1-C_8)$alkyl, or $R^7$ and $R^8$ together form a four-, five-, six-, or seven-membered heterocycle, $(C_1-C_8)$ heteroalkyl, $(C_1-C_8)$substituted heteroalkyl, aryl, substituted aryl, heteroaryl, substituted heteroaryl;

$R^9$ is H, $CH_3$, $CH_2CH_3$ or $CH(CH_3)_2$.

In certain cases, the coumarin moiety of Structure 150 is of Structure 153.

Structure 153

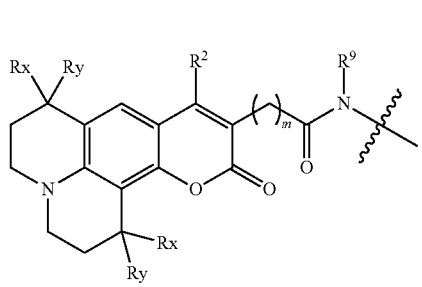

With respect to Structure 153: m is 0, 1, 2, 3, 4, 5, 6, 7, 8, 9 or 10; $R^2$ is H or $CH_3$; $R_x$ and $R_y$, and independently H or $CH_3$; $R^9$ is H, $CH_3$, $CH_2CH_3$ or $CH(CH_3)_2$.

In certain cases, the coumarin moiety of Structure 150 is of Structure 154.

Structure 154

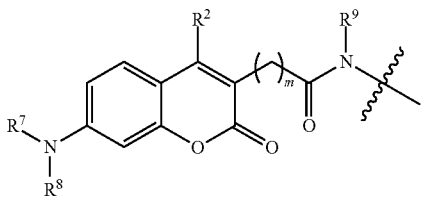

With respect to Structure 154: m is 0, 1, 2, 3, 4, 5, 6, 7, 8, 9 or 10; $R^2$ is H or $CH_3$; $R^7$ and $R^8$ are independently selected from H, $(C_1-C_8)$alkyl, $(C_1-C_8)$substituted alkyl, or $R^7$ and $R^8$ together form a four-, five-, six-, or seven-membered heterocycle; $R^9$ is H, $CH_3$, $CH_2CH_3$ or $CH(CH_3)_2$.

In certain cases, the coumarin moiety of Structure 150 is of Structure 155.

Structure 155

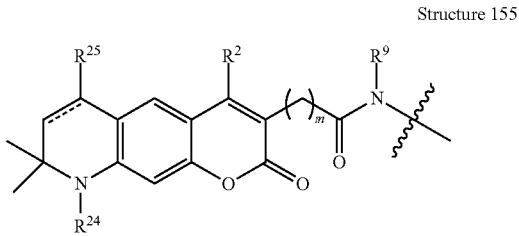

With respect to Structure 155: m is 0, 1, 2, 3, 4, 5, 6, 7, 8, 9 or 10; $R^2$ is H or $CH_3$; $R^9$ is H, $CH_3$, $CH_2CH_3$ or $CH(CH_3)_2$; $R^{24}$ is $(C_1-C_8)$alkyl or $(C_1-C_8)$substituted alkyl; $R^{25}$ is $(C_1-C_8)$alkyl, $(C_1-C_8)$substituted alkyl or $CH_2SO_3H$.

Methods

In a method aspect, the present invention provides a method of making a probe including a coumarin moiety. The method involves: 1) synthesizing the coumarin moiety-containing probe using a solid phase synthesis method; 2) removing the probe from the solid support at a temperature between 50° C. and 70° C., in concentrated ammonia, for a period of 2 h to 8 h; 3) isolating the probe. The isolated coumarin moiety is degraded to an extent less than 10.0 percent as the result of probe removal. Typically the coumarin moiety is degraded to an extent less than 5.0 percent, 2.5 percent or 1.0 percent.

In a method aspect, the present invention provides a method of making a probe including a coumarin moiety. The method involves: 1) synthesizing the coumarin moiety-containing probe using a solid phase synthesis method; 2) removing the probe from the solid support at a temperature between 50° C. and 70° C., in concentrated ammonia, for a period of 2 h to 8 h; 3) isolating the probe. The isolated coumarin moiety is degraded to an extent less than 10.0 percent as the result of probe removal. Typically the coumarin moiety is degraded to an extent less than 5.0 percent, 2.5 percent or 1.0 percent.

In a method aspect, the present invention provides a method of making a probe including a coumarin moiety. The method involves: 1) synthesizing the coumarin moiety-containing probe using a solid phase synthesis method; 2) removing the probe from the solid support at a temperature between 60° C. and 80° C., in 1:3 tert-butylamine/water, for a period of 4 h to 12 h; 3) isolating the probe. The isolated coumarin moiety is degraded to an extent less than 10.0 percent as the result of probe removal. Typically the coumarin moiety is degraded to an extent less than 5.0 percent, 2.5 percent or 1.0 percent.

In a method aspect, the present invention provides a method for determining whether a sample contains an enzyme. The method includes: (a) contacting the sample with a peptide construct that includes a coumarin-based fluorophore of the present invention; (b) exciting said fluorophore; and (c) determining a fluorescence property of said sample, wherein the presence of said enzyme in said sample results in a change in said fluorescence property.

Preferred peptide constructs include: i) a fluorophore, where the fluorophore is a coumarin-based fluorophore of the present invention; ii) a quencher; and iii) a cleavage recognition site for the enzyme. Moreover, the peptide is preferably in a conformation allowing donor-acceptor energy transfer between the fluorophore and the quencher when the fluorophore is excited.

In another method aspect, the invention provides a method for determining whether a compound alters an activity of an enzyme. Preferred embodiments of this aspect of the invention include the steps recited in connection with the above-recited aspect of the invention and further include a step (c) determining a fluorescence property of the sample, wherein said activity of said enzyme in said sample results in a change in the fluorescence property.

In another method aspect, the present invention provides a method for detecting a nucleic acid target sequence. The method includes: (a) contacting the target sequence with a detector nucleic acid; (b) hybridizing the target binding sequence to the target sequence, thereby altering the conformation of the detector nucleic acid, causing a change in a fluorescence parameter; and (c) detecting the change in the fluorescence parameter, thereby detecting the nucleic acid target sequence.

In the methods described herein, unless otherwise noted, a preferred detector nucleic acid includes a single-stranded target binding sequence. The binding sequence has linked thereto: i) a coumarin-based fluorophore of the present invention; and ii) a quencher.

In another method aspect, the invention provides a method for detecting amplification of a target sequence. The method includes the use of an amplification reaction including the following steps: (a) hybridizing the target sequence and a detector nucleic acid. The detector nucleic acid includes a single-stranded target binding sequence and an intramolecularly associated secondary structure 5' to the target binding sequence. At least a portion of the detector sequence forms a single stranded tail which is available for hybridization to the target sequence; (b) extending the hybridized detector nucleic acid on the target sequence with a polymerase to produce a detector nucleic acid extension product and separating the detector nucleic acid extension product from the target sequence; (c) hybridizing a primer to the detector nucleic acid extension product and extending the primer with the polymerase, thereby linearizing the intramolecularly associated secondary structure and producing a change in a fluorescence parameter; and (d) detecting the change in the fluorescence parameter, thereby detecting the target sequence.

In another method aspect, the present invention provides a method for determining whether a sample contains an enzyme. The method comprises: (a) contacting the sample with a peptide construct; (b) exciting the coumarin-based fluorophore; and (c) determining a fluorescence property of the sample, wherein the presence of the enzyme in the sample results in a change in the fluorescence property.

Peptide constructs useful in practicing the invention include those with the following features: i) a fluorophore, where the fluorophore is a coumarin-based fluorophore of the present invention; ii) a quencher; and iii) a cleavage recognition site for the enzyme.

In another method aspect, the present invention provides a method of making a coumarin-CPG compound. The method comprises the following steps: Preparing a first coumarin-based compound of Structure 156

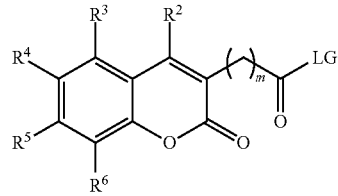

Structure 156

With respect to Structure 156: m is 0, 1, 2, 3, 4, 5, 6, 7, 8, 9 or 10; $R^2$ is H or $CH_3$; LG is a leaving group. A leaving group is a molecular fragment that departs with a pair of electrons in heterolytic bond cleavage. Leaving groups can be anions or neutral molecules, but in either case the leaving group is able to stabilize the additional electron density that results from bond heterolysis. Nonlimiting examples of leaving groups include halides (e.g., $Cl^-$), oxygen-based anions (e.g., $CH_3CO_2^-$, $C_4H_4NO_2\_O^-$), sulfur-based anions (e.g., $CH_3S$—) and the like.

$R^3$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl;

$R^4$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl;

$R^5$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl, or $R^4$, $R^5$ and $R^6$ together form fused ring systems having five- or six-membered rings;

$R^6$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, or $R^7$ and $R^8$ together form a four-, five-, six-, or seven-membered heterocycle, ($C_1$-$C_8$) heteroalkyl, ($C_1$-$C_8$)substituted heteroalkyl, aryl, substituted aryl, heteroaryl, substituted heteroaryl;

Reacting the first coumarin-based compound with an amine of Structure 157

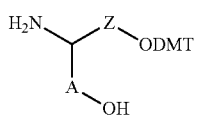

Structure 157

With respect to Structure 157, Z is $(CH_2)_x$, wherein x is 1, 2, 3, 4, 5, 6, 7, 8, 9 or 10; A is $(CH_2)_y$, wherein y is 1, 2, 3, 4, 5, 6, 7, 8, 9 or 10.

Reaction of the first coumarin-based compound with an amine of Structure 157 provides a second coumarin-based compound of Structure 158.

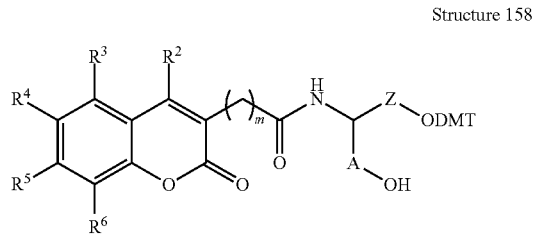

Structure 158

Reacting the second coumarin-based compound with a first linker group of Structure 159

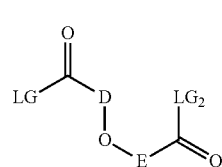

Structure 159

With respect to Structure 159, LG is a first leaving group, $LG_2$ is a second leaving group, D is $(CH_2)x$ where x is 1, 2, 3, 4, 5, 6, 7, 8, 9 or 10, E is $(CH_2)y$ where y is 1, 2, 3, 4, 5, 6, 7, 8, 9 or 10.

Reaction of Structure 158 with Structure 159 provides a third coumarin-based compound of Structure 160.

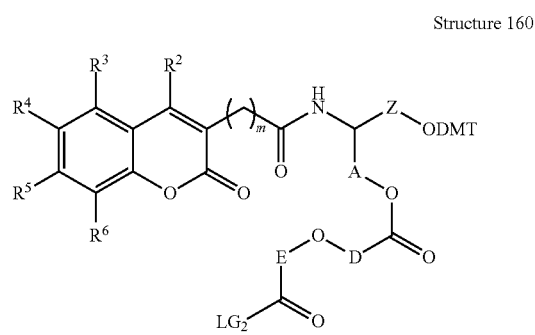

Structure 160

Reaction of the third coumarin-based structure (Structure 160) with CPG functionalized with a nucleophile (Structure 161) provides the coumarin-CPG compound.

Structure 161

With respect to the method of making a coumarin-CPG compound, in certain cases the first coumarin-based compound is of Structure 162.

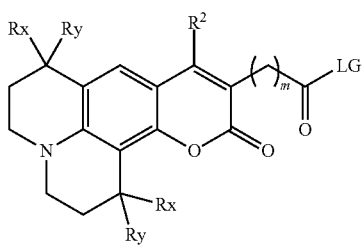

Structure 162

Regarding Structure 162: LG is a leaving group; m is 0, 1, 2, 3, 4, 5, 6, 7, 8, 9 or 10; $R^2$ is H or $CH_3$; $R_x$ and $R_y$ and independently H or $CH_3$.

With respect to the method of making a coumarin-CPG compound, in certain cases the first coumarin-based compound is of Structure 163.

Structure 163

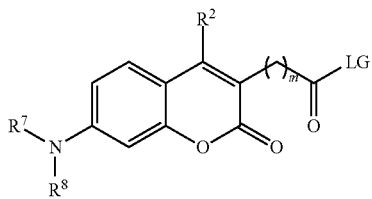

Regarding Structure 163: LG is a leaving group; m is 0, 1, 2, 3, 4, 5, 6, 7, 8, 9 or 10; $R^2$ is H or $CH_3$; $R^7$ and $R^8$ are independently selected from H, $(C_1-C_8)$alkyl, $(C_1-C_8)$substituted alkyl, or $R^7$ and $R^8$ together form a four-, five-, six-, or seven-membered heterocycle.

With respect to the method of making a coumarin-CPG compound, in certain cases the first coumarin-based compound is of Structure 164.

Structure 164

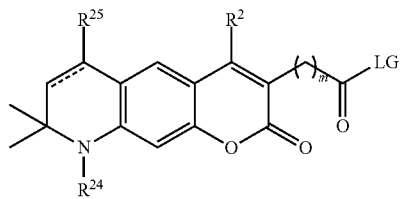

Regarding Structure 164: m is 0, 1, 2, 3, 4, 5, 6, 7, 8, 9 or 10; LG is a leaving group; $R^2$ is H or $CH_3$; $R^{24}$ is $(C_1-C_8)$alkyl or $(C_1-C_8)$substituted alkyl; $R^{25}$ is $(C_1-C_8)$alkyl, $(C_1-C_8)$substituted alkyl or $CH_2SO_3H$.

In another method aspect, the invention provides a method of conjugating a first molecule with a second molecule using Click Chemistry (addition of azide to alkyne, typically mediated by a metal catalyst) to afford a probe containing at least one coumarin-based fluorophore of the present invention. Either the first molecule or the second molecule includes an azide moiety; the first or second molecule that does not include an azide moiety includes an alkyne moiety. The at least one coumarin-based fluorophore of the present invention originally arises from the first molecule and/or the second molecule.

Nonlimiting examples of azides used in the Click Chemistry method discussed above include Structure 165, Structure 166, Structure 167 and Structure 168.

Structure 165

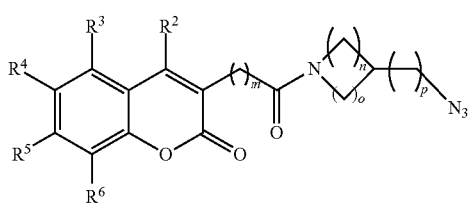

Structure 166

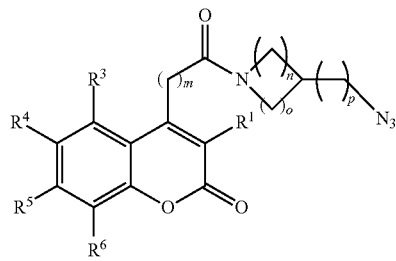

Structure 167

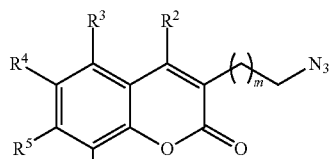

Structure 168

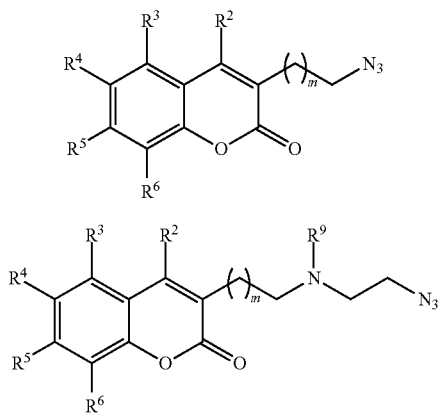

Substituents and variables for Structures 165-168 are defined as follows: m is 0, 1, 2, 3, 4, 5, 6, 7, 8, 9 or 10; n is 0, 1, 2 or 3; o is 0, 1, 2 or 3; p is 0, 1, 2, 3, 4, 5, 6, 7, 8, 9 or 10; $R^2$ is selected from a group consisting of —H or —$CH_3$;

$R^3$ is selected from a group consisting of —H, -halogen, —$CF_3$, —OH, —$NH_2$, —CCH, —CN, —$NO_2$, $(C_1-C_8)$ alkyl, $(C_1-C_8)$substituted alkyl, $(C_1-C_8)$alkylthio, $(C_1-C_8)$ substituted alkylthio, $(C_1-C_8)$alkoxy, $(C_1-C_8)$substituted alkoxy, —$NR^7R^8$ where $R^7$ and $R^8$ are independently selected from H, $(C_1-C_8)$alkyl, or $R^7$ and $R^8$ together form a four-, five-, six-, or seven-membered heterocycle, $(C_1-C_8)$ heteroalkyl, $(C_1-C_8)$substituted heteroalkyl, aryl, substituted aryl, heteroaryl, substituted heteroaryl, or $R^3$ together with $R^4$ form a five- or six-membered carbocyclic or heterocyclic ring (e.g., piperidinyl);

$R^4$ is selected from a group consisting of —H, -halogen, —$CF_3$, —OH, —$NH_2$, —CCH, —CN, —$NO_2$, $(C_1-C_8)$ alkyl, $(C_1-C_8)$substituted alkyl, $(C_1-C_8)$alkylthio, $(C_1-C_8)$ substituted alkylthio, $(C_1-C_8)$alkoxy, $(C_1-C_8)$substituted alkoxy, —$NR^7R^8$ where $R^7$ and $R^8$ are independently selected from H, $(C_1-C_8)$alkyl, or $R^7$ and $R^8$ together form a four-, five-, six-, or seven-membered heterocycle, $(C_1-C_8)$ heteroalkyl, $(C_1-C_8)$substituted heteroalkyl, aryl, substituted aryl, heteroaryl, substituted heteroaryl, or $R^4$ together with $R^5$ form a five- or six-membered carbocyclic or heterocyclic ring (e.g., piperidinyl);

$R^5$ is selected from a group consisting of —H, -halogen, —$CF_3$, —OH, —$NH_2$, —CCH, —CN, —$NO_2$, $(C_1-C_8)$ alkyl, $(C_1-C_8)$substituted alkyl, $(C_1-C_8)$alkylthio, $(C_1-C_8)$ substituted alkylthio, $(C_1-C_8)$alkoxy, $(C_1-C_8)$substituted alkoxy, —$NR^7R^8$ where $R^7$ and $R^8$ are independently selected from H, $(C_1-C_8)$alkyl, or $R^7$ and $R^8$ together form a four-, five-, six-, or seven-membered heterocycle, $(C_1-C_8)$ heteroalkyl, $(C_1-C_8)$substituted heteroalkyl, aryl, substituted aryl, heteroaryl, substituted heteroaryl, or $R^5$ together with $R^6$ form a five- or six-membered carbocyclic or heterocyclic ring (e.g., piperidinyl); or $R^4$, $R^5$ and $R^6$ together form fused carbocyclic or heterocyclic ring systems having five- or six-membered rings;

$R^6$ is selected from a group consisting of —H, -halogen, —$CF_3$, —OH, —$NH_2$, —CCH, —CN, —$NO_2$, ($C_1$-$C_8$) alkyl, ($C_1$-$C_8$)substituted alkyl, ($C_1$-$C_8$)alkylthio, ($C_1$-$C_8$) substituted alkylthio, ($C_1$-$C_8$)alkoxy, ($C_1$-$C_8$)substituted alkoxy, —$NR^7R^8$ where $R^7$ and $R^8$ are independently selected from H, ($C_1$-$C_8$)alkyl, ($C_1$-$C_8$)substituted alkyl, or $R^7$ and $R^8$ together form a four-, five-, six-, or seven-membered heterocycle, ($C_1$-$C_8$)heteroalkyl, ($C_1$-$C_8$)substituted heteroalkyl, aryl, substituted aryl, heteroaryl, substituted heteroaryl.

In another method aspect, the invention provides methods of determining the amount of activity of an enzyme in a sample from an organism. The method includes: (a) contacting a sample comprising the enzyme and the compound with a peptide construct comprising (b) exciting the fluorophore; and (c) determining a fluorescence property of the sample, wherein the activity of the enzyme in the sample results in a change in the fluorescence property. Peptide constructs useful in this aspect of the invention are substantially similar to those described immediately above.

EXAMPLES

Example 1

Preparation of Compound 201

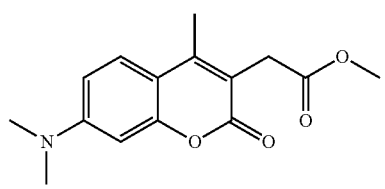

Methyl 2-(7-(dimethylamino)-4-methyl-2-oxo-2H-chromen-3-yl)acetate

A round bottomed flask equipped with a magnetic stirrer was charged with 3-dimethylaminophenol (66.3 g, 483 mmoles), dimethyl 2-acetylsuccinate (86.2 g, 531 mmoles) and zinc chloride (92.2 g, 676 mmoles). The mixture was heated to 120° C. for 24 hours and cooled. The reaction mass was partitioned between DCM (1.5 L) and water (4 L) plus concentrated HCl (70 ml). The layers were separated and the aqueous phase was extracted with DCM (2×1 L). The organic phases were combined and washed with water (2×4 L). The organic phase was extracted with 0.5 N KOH (1 L, 2×500 ml) and these washes saved for extraction of the coumarin acid below. The organic phase was washed with brine (4 L), dried with $MgSO_4$ and concentrated to give 31.0 grams of a red semisolid. Recrystallization from IPA (150 ml) gave compound 21 as a pink solid (14.6 g, 11% yield). m.p. 130-132° C. $^1$H NMR (400 MHz, DMSO-$d_6$) δ 1.18 (3H, t, J=7.0 Hz), 3.00 (6H, s), 3.88 (2H, s), 4.10 (2H, q, J=7.1 Hz), 6.05 (1H, s), 6.56 (1H, d, J=2.8 Hz), 6.73 (1H, dd, J=2.8, 9.2 Hz), 7.43 (1H, d, J=9.2 Hz). MS (ES+) m/z: [M+H]$^+$ calcd. for $C_{15}H_{17}NO_4$: 276.12. found: 276.12. Anal. calcd. for $C_{15}H_{17}NO_4$: C, 65.44; H, 6.22; N, 5.09. Found: C, 65.49; H, 6.18; N, 5.08.

Example 2

Preparation of Compound 202

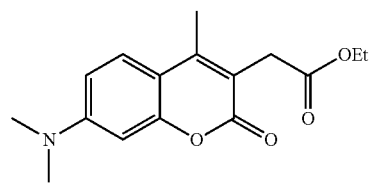

The procedure of Example 1 was followed using diethyl 2-acetylsuccinate in place of dimethyl 2-acetylsuccinate to yield compound 202 as a light purple solid in 24% yield. m.p. 125-127° C. $^1$H NMR (400 MHz, DMSO-$d_6$) δ 1.18 (3H, t, J=7.0 Hz), 3.00 (6H, s), 3.88 (2H, s), 4.10 (2H, q, J=7.1 Hz), 6.05 (1H, s), 6.56 (1H, d, J=2.8 Hz), 6.73 (1H, dd, J=2.8, 9.2 Hz), 7.43 (1H, d, J=9.2 Hz). MS (ES+) m/z: [M+H]$^+$ calcd. for $C_{16}H_{19}NO_4$: 290.14. found: 290.14. Anal. calcd. for $C_{16}H^{19}NO_4$: C, 66.42; H, 6.62; N, 4.84. Found: C, 66.25; H, 6.57; N, 5.00.

Example 3

Preparation of Compound 203

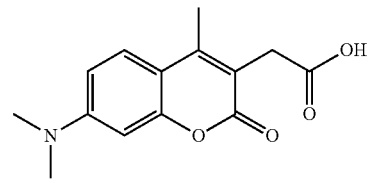

2-(7-(dimethylamino)-4-methyl-2-oxo-2H-chromen-3-yl)acetic acid

Procedure A: The alkaline washes from Example 1 were acidified with AcOH. The solids were filtered out and dried to yield compound 203 as a pink solid (25.2 g, 20% yield). Similarly the alkaline washes from Example 2 were acidified with AcOH to give 203 in 11% yield.

Procedure B: Compound 202 (4 g) was dissolved in MeOH (25 ml) in a round bottomed flask equipped with a magnetic stirrer. 10% KOH/MeOH (25 ml) was added and the reaction stirred at RT for 18 hours. The mixture was acidified with AcOH and the solids were filtered out and dried to yield compound 203 as a pink solid (3.43 g, 95% yield). m.p. 206-208° C. $^1$H NMR (400 MHz, DMSO-$d_6$) δ 2.31 (3H, s), 3.01 (6H, s), 3.52 (2H, s), 6.55 (1H, d, J=2.4 Hz), 6.74 (1H, dd, J=2.4, 9.2 Hz), 7.58 (1H, d, J=9.2 Hz), 12.34 (1H, s). MS (ES+) m/z: [M+H]$^+$ calcd. for $C_{14}H_{15}NO_4$: 262.11. found: 262.11.

Example 4

Preparation of Compound 204

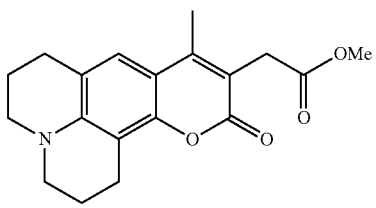

Methyl 2-(9-methyl-11-oxo-2,3,5,6,7,11-hexahydro-1H-pyrano[2,3-f]pyrido[3,2,1-ij]quinolin-10-yl)acetate The procedure of Example 1 was followed using 8-hydroxy-julolidine in place of 3-dimethylaminophenol to yield compound 204 as a pale tan solid (28% yield). m.p. 117-119° C. $^1$H NMR (400 MHz, DMSO-d$_6$) δ 1.88 (4H, m, J=5.6 Hz), 2.25 (3H, s), 2.71 (4H, q, J=6.8 Hz), 3.21 (4H, q, J=6.3 Hz), 3.58 (2H, s), 3.59 (3H, s), 7.15 (1H, s). MS (ES+) m/z: [M+H]$^+$ calcd. for C$_{19}$H$_{21}$NO$_4$: 327.15. found: 327.15. Anal. calcd. for C$_{19}$H$_{21}$NO$_4$: C, 69.71; H, 6.47; N, 4.28. Found: C, 69.55; H, 6.38; N, 4.20.

Example 5

Preparation of Compound 205

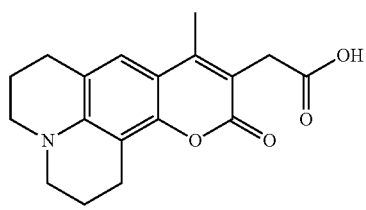

2-(9-methyl-11-oxo-2,3,5,6,7,11-hexahydro-1H-pyrano[2,3-f]pyrido[3,2,1-ij]quinolin-10-yl)acetic acid The alkaline washes from Example 4 were acidified with AcOH. The solids were filtered out and dried to yield compound 205 as a pale yellow solid (27% yield). m.p. 182-186° C. $^1$H NMR (400 MHz, DMSO-d$_6$) δ 1.89 (4H, m), 2.25 (3H, s), 2.73 (4H, q, J=6.1 Hz), 3.22 (4H, q, J=5.9 Hz), 3.47 (2H, s), 7.16 (1H, s), 12.45 (1H, very br s). MS (ES+) m/z: [M+H]$^+$ calcd. for C$_{18}$H$_{19}$NO$_4$: 314.14. found: 314.14.

Example 6

Preparation of Compound 206

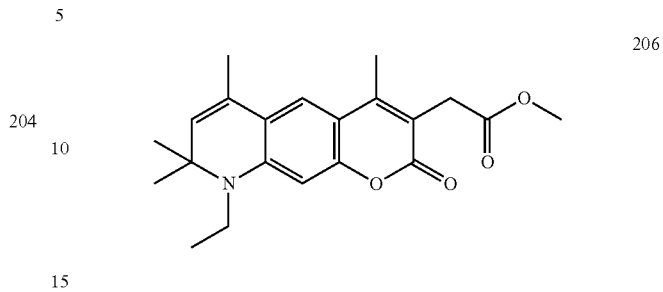

Methyl 2-(9-ethyl-4,6,8,8-tetramethyl-2-oxo-8,9-dihydro-2H-pyrano[3,2-g]quinolin-3-yl)acetate A round bottomed flask equipped with a magnetic stirrer was charged with 1-ethyl-2,2,4-trimethyl-1,2-dihydroquinolin-7-ol hydrobromide (14.9 g, 50 mmoles), dimethyl 2-acetylsuccinate (18.8 g, 100 mmoles) and zinc chloride (19.1 g, 140 mmoles). The mixture was heated to 125° C. for 20 hours and then cooled. The reaction mass was partitioned between DCM (400 mL) and water (600 mL) plus concentrated HCl (10 ml). The layers were separated and the aqueous phase was extracted with DCM (2×300 mL). The organic phases were combined and washed with water (2×600 mL) and brine (800 mL), dried with MgSO$_4$ and concentrated to give a dark green syrup (13.7 g, 77% yield). This crude material was purified by column chromatography on silica gel with 0% to 2% MeOH/DCM to give a greenish solid (7.0 g, 39% yield). Recrystallization from IPA (50 ml) gave compound 206 as a yellow solid (3.54 g, 20% yield). m.p. 107-109° C. $^1$H NMR (400 MHz, DMSO-d$_6$) δ 1.13 (3H, t, J=5.6 Hz), 1.34 (6H, s), 1.98 (3H, d, J=0.8 Hz), 2.31 (3H, s), 3.40 (2H, q, J=5.6 Hz), 3.60 (2H, s), 3.61 (3H, s), 5.40 (1H, s), 6.34 (1H, s), 7.21 (1H, s). MS (ES+) m/z: [M+H]$^+$ calcd. for C$_{21}$H$_{25}$NO$_4$: 356.19. found: 356.19.

Example 7

Preparation of Compound 207

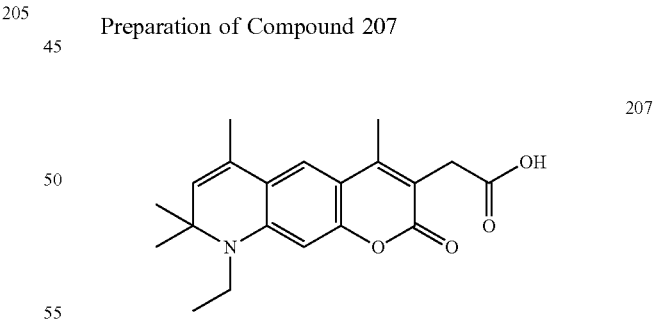

2-(9-Ethyl-4,6,8,8-tetramethyl-2-oxo-8,9-dihydro-2H-pyrano[3,2-g]quinolin-3-yl)acetic acid Coumarin ester 206 (3 g, 8.44 mmol) was dissolved in MeOH (20 ml) and 10% KOH/MeOH (20 ml) was added. After 14 hours stirring at RT acetic acid (1.2 ml) was added and the mixture concentrated. The residue was dissolved and additional acetic acid was added (1.5 ml) to form a slurry which was kept at 4° C. overnight. The next day the supernatant was decanted off the dark gummy mass. The gum was dissolved in DCM (100 ml) and washed with water (50 ml) and brine (50 ml). The organic phase was dried with MgSO$_4$ and concentrated to give compound 207 as a brownish yellow solid (2.44 g, 85% yield). M.p. 223-227° C. $^1$H NMR (400 MHz, DMSO-d$_6$) δ 1.14 (3H, t, J=5.6 Hz), 1.34 (6H, s), 1.99 (3H, d, J=0.8 Hz), 2.31 (3H, s), 3.40 (2H, q, J=5.6 Hz), 3.51 (2H, s), 5.40 (1H, d, J=1.2 Hz), 6.39 (1H, s), 7.21 (1H, s), 12.31 (1H, s). MS (ES+) m/z: [M+H]$^+$ calcd. for C$_{20}$H$_{23}$NO$_4$: 342.17. found: 342.17.

Example 8

Preparation of Compound 208

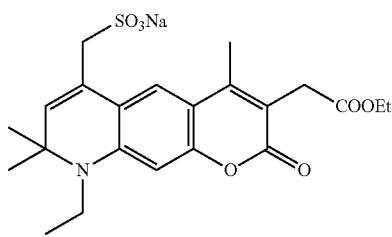

Sodium (3-(2-ethoxy-2-oxoethyl)-9-ethyl-4,8,8-trimethyl-2-oxo-8,9-dihydro-2H-pyrano[3,2-g]quinolin-6-yl)methanesulfonate Sodium (1-ethyl-7-hydroxy-2,2-dimethyl-1,2-dihydroquinolin-4-yl)methanesulfonate (2.14 g, 6.70 mmol) was reacted with diethyl acetylsuccinate (2.90 g, 13.4 mmol) and zinc chloride (2.56 g, 18.8 mmol) at 125° C. for 20 hours. The mixture was cooled and triturated with EtOH (3×40 ml). The EtOH washes were concentrated to give a black residue (5.35 g). This crude material was purified by column chromatography on silica gel with 0-15% MeOH/DCM. Concentration of product fractions yielded compound 208 as a dark gum (482 mg, 15% yield). $^1$H NMR (400 MHz, DMSO-d$_6$) δ 1.15 (3H, t, J=6.4 Hz), 1.18 (3H, t, J=6.4 Hz), 1.34 (6H, s), 2.31 (3H, s), 3.17 (3H, d, J=3.2 Hz), 3.40 (2H, q, J=5.2 Hz), 3.58 (2H, s), 3.61 (3H, s), 4.08 (4H, overlapping m), 5.48 (1H, s), 6.30 (1H, s), 7.77 (1H, s). MS (ES+) m/z: [M+H]$^+$ calcd. for C$_{22}$H$_{27}$NO$_7$S (acid form): 450.16. found: 450.16.

Example 9

Preparation of Compound 209

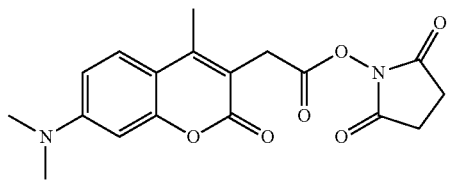

2,5-dioxopyrrolidin-1-yl 2-(7-(dimethylamino)-4-methyl-2-oxo-2H-chromen-3-yl)acetate Compound 203 (20 g, 76.5 mmoles) and NHS (10.6 g, 91.8 mmoles) were dissolved in DMF (800 ml) in a round bottomed flask equipped with a magnetic stirrer. Dicyclohexyl carbodiimide (20.5 g, 99.5 mmoles) was added and the reaction was stirred at RT for 48 hours. The slurry was filtered and the filtrate was poured into icewater (3 L) with stirring. The precipitate was filtered out, washed with water and dried to yield compound 206 as a pale yellow solid (31.9 g, 121% yield). NMR indicated that this material contained 18 molar % DCU that did not affect the ensuing reaction. $^1$H NMR (400 MHz, DMSO-d$_6$) δ 2.37 (3H, s), 2.79 (4H, br s), 3.03 (6H, s), 4.01 (2H, s), 6.57 (1H, d, J=2.4 Hz), 6.75 (1H, dd, J=2.4, 8.8 Hz), 7.63 (1H, d, J=9.2 Hz).

Example 10

Preparation of Compound 210

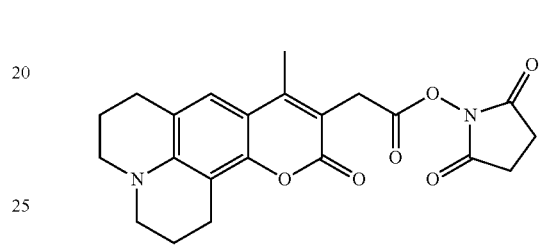

2,5-dioxopyrrolidin-1-yl 2-(9-methyl-11-oxo-2,3,5,6,7,11-hexahydro-1H-pyrano[2,3-f]pyrido[3,2,1-ij]quinolin-10-yl)acetate The procedure of Example 9 was followed using compound 205 in place of compound 203 to yield compound 210 as a yellow solid in 116% yield. NMR indicated that this material contained 25 molar % DCU. $^1$H NMR (400 MHz, DMSO-d$_6$) δ 1.88 (4H, m, J=6.0 Hz), 2.32 (3H, s), 2.73 (4H, m, J=4.4 Hz), 2.79 (4H, br s), 3.24 (4H, q, J=5.9 Hz), 3.98 (2H, s), 7.22 (1H, s).

Example 11

Preparation of Compound 211

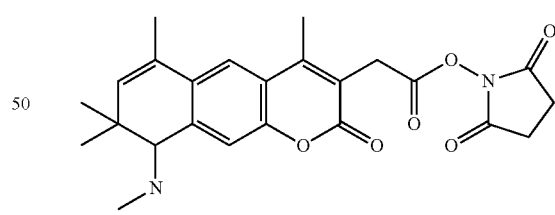

2,5-dioxopyrrolidin-1-yl 2-(9-ethyl-4,6,8,8-tetramethyl-2-oxo-8,9-dihydro-2H-pyrano[3,2-g]quinolin-3-yl)acetate Coumarin acid 207 (2.0 g, 5.86 mmol) was reacted with N,N'-disuccinimidyl carbonate (1.95 g, 7.62 mmol) and DIEA (909 mg, 7.03 mmol) in DMF (30 ml). After 4 hours stirring at RT the mixture was poured into cold water (400 ml) to give a yellow suspension which was kept at 4° C. overnight. Suction filtration gave a yellow solid which was dissolved in DCM (40 ml) and washed with water (20 ml)

and brine (20 ml). The organic phase was dried with MgSO$_4$ and concentrated to give compound 211 as an amber foam (2.32 g, 90% yield). $^1$H NMR (400 MHz, DMSO-d$_6$) δ 1.15 (3H, t, J=6.4 Hz), 1.35 (6H, s), 2.00 (3H, d, J=0.4 Hz), 2.38 (3H, s), 2.80 (4H, br s), 3.42 (2H, q, J=6.4 Hz), 4.00 (2H, s), 5.42 (1H, s), 6.34 (1H, s), 7.24 (1H, s).

Example 12

Preparation of Compound 212

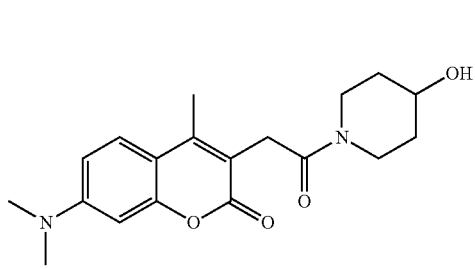

7-(dimethylamino)-3-(2-(4-hydroxypiperidin-1-yl)-2-oxoethyl)-4-methyl-2H-chromen-2-one Compound 211 (15 g, 34.6 mmoles) and 4-hydroxypiperidine (4.55 g, 45 mmoles) were dissolved in DMF (200 ml) in a round bottomed flask equipped with a magnetic stirrer. After stirring for 4 hours at RT, the flask was kept at 4° C. overnight. The precipitate was filtered out, washed with DMF (2×25 ml), DCM (2×25 ml) and dried to yield compound 212 as a white solid in 125% yield. NMR indicated the presence of 26 mole % DCU. $^1$H NMR (400 MHz, DMSO-d$_6$) δ 1.24 (3H, m), 1.39 (1H, m), 1.69 (3H, m), 2.23 (3H, s), 2.90 (1H, m), 3.01 (6H, s), 3.25 (1H, m), 3.48 (1H, m), 3.60 (2H, d, J=2.8 Hz), 3.70 (1H, m), 3.87 (2H, m), 6.54 (1H, d, J=2.4 Hz), 6.69 (1H, dd, J=2.4, 8.8 Hz), 7.43 (1H, d, J=8.8 Hz). MS (ES+) m/z: [M+H]$^+$ calcd. for C$_{19}$H$_{24}$N$_2$O$_4$: 345.18. found: 345.18.

Example 13

Preparation of Compound 213

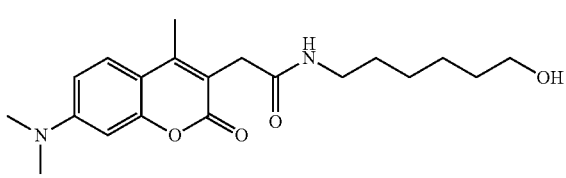

2-(7-(dimethylamino)-4-methyl-2-oxo-2H-chromen-3-yl)-N-(6-hydroxyhexyl)acetamide The procedure of Example 12 was followed using aminohexanol in place of 4-hydroxypiperidine to yield compound 213 as a cream white solid in 100% yield. NMR indicated that this material contained 16 molar % DCU. $^1$H NMR (400 MHz, DMSO-d$_6$) δ 1.24 (4H, m), 1.37 (3H, m), 2.28 (3H, s), 3.01 (6H, s), 3.37 (2H, m), 4.33 (1H, t, J=5.2 Hz), 6.54 (1H, d, J=2.4 Hz), 6.73 (1H, dd, J=2.4, 8.8 Hz), 7.56 (1H, d, J=8.8 Hz), 7.83 (1H, t, J=5.7 Hz). MS (ES+) m/z: [M+H]$^+$ calcd. for C$_{20}$H$_{28}$N$_2$O$_4$: 361.21. found: 361.21.

Example 14

Preparation of Compound 214

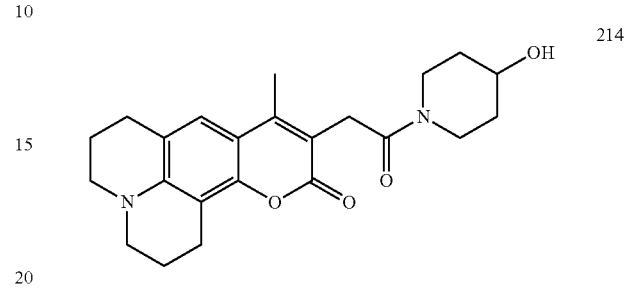

10-(2-(4-hydroxypiperidin-1-yl)-2-oxoethyl)-9-methyl-2,3,6,7-tetrahydro-1H-pyrano[2,3-f]pyrido[3,2,1-ij]quinolin-11(5H)-one The procedure of Example 12 was followed using compound 210 in place of compound 209 to yield compound 214 as a pale yellow solid in 116% yield. NMR indicated that this material contained 25 molar % DCU. $^1$H NMR (400 MHz, DMSO-d$_6$) δ 1.23 (2H, m), 1.68 (2H, m), 1.88 (4H, m, J=5.9 Hz), 2.19 (3H, s), 2.74 (4H, q, J=6.4 Hz), 3.22 (4H, q, J=6.4 Hz), 3.57 (2H, d, J=3.2 Hz), 3.57 (1H, m), 3.70 (1H, m), 3.86 (2H, m), 7.14 (1H, s). MS (ES+) m/z: [M+H]$^+$ calcd. for C$_{23}$H$_{28}$N$_2$O$_4$: 397.21. found: 397.21.

Example 15

Preparation of Compound 215

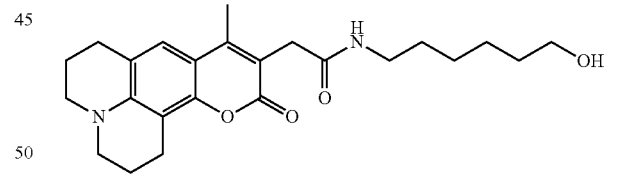

N-(6-hydroxyhexyl)-2-(9-methyl-11-oxo-2,3,5,6,7,11-hexahydro-1H-pyrano[2,3-f]pyrido[3,2,1-ij]quinolin-10-yl)acetamide The procedure of Example 13 was followed using aminohexanol in place of 4-hydroxy-piperidine to yield compound 215 as a very pale yellow solid in 98% yield. $^1$H NMR (400 MHz, DMSO-d$_6$) δ 1.24 (4H, m), 1.38 (4H, q, J=6.9 Hz), 1.88 (4H, q, J=5.9 Hz), 2.73 (4H, q, J=6.3 Hz), 3.00 (2H, q, J=6.6 Hz), 3.22 (2H, q, J=5.9 Hz), 3.37 (4H, m), 4.32 (1H, t, J=5.2 Hz) 7.14 (1H, s), 7.76 (1H, t, J=5.6 Hz). MS (ES+) m/z: [M+H]$^+$ calcd. for C$_{24}$H$_{32}$N$_2$O$_4$: 413.24. found: 413.24.

Example 16

Preparation of Compound 216

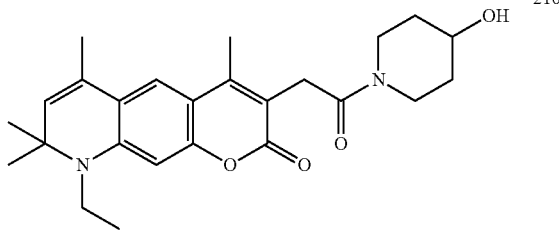

9-ethyl-3-(2-(4-hydroxypiperidin-1-yl)-2-oxoethyl)-4,6,8,8-tetramethyl-8,9-dihydro-2H-pyrano[3,2-g]quinolin-2-one Compound 211 (2.00 g, 4.56 mmol) was reacted with HO-piperidine (554 mg, 5.47 mmol) in DMF (10 ml) at RT. After 2 hours the reaction was kept at 4° C. overnight. Suction filtration gave the compound 216 as a pale yellow powder (872 mg, 45% yield). Water (20 ml) was added to the filtrate to precipitate out more product. Suction filtration gave additional 216 (1.00 g, 52% yield).). $^1$H NMR (400 MHz, DMSO-d$_6$) δ 1.14 (3H, t, J=5.6 Hz), 1.22 (2H, m), 1.34 (6H, s), 1.68 (2H, m), 1.79 (1H, m), 1.99 (3H, s), 2.24 (3H, s), 2.44 (2H, m), 2.54 (3H, s), 2.89 (1H, m), 2.99 (1H, m), 3.26 (1H, m), 3.40 (2H, q, J=6 Hz), 3.45 (1H, m), 3.60 (2H, d, J=3.6), 3.71 (1H, m, J=3.2 Hz), 3.86 (2H, m), 5.39 (1H, d, J=0.4 Hz), 6.33 (1H, s), 7.19 (1H, s). MS (ES+) m/z: [M+H]$^+$ calcd. for C$_{25}$H$_{32}$N$_2$O$_4$: 425.24. found: 425.24.

Example 17

Preparation of Compound 217

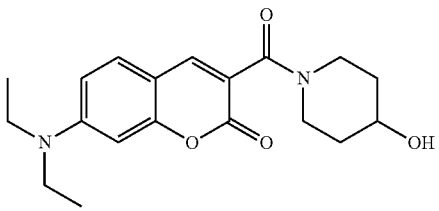

7-(diethylamino)-3-(4-hydroxypiperidine-1-carbonyl)-2H-chromen-2-one 4-(diethylamino)-2-hydroxybenzaldehyde (10 g, 51.7 mmoles), diethyl malonate (9.95 g, 62.1 mmoles), 4-hydroxypiperidine (26.2 g, 259 mmoles), piperidine (5 drops) and acetic acid (5 drops) were added to a round bottomed flask equipped with a magnetic stirrer. The reaction was heated to 100° C. for 4 hours. After cooling the syrup was poured into water (400 ml) and extracted with DCM (3×200 ml). The organic phase was washed with water (2×300 ml), 1 M aqueous citric acid (3×300 ml) and brine (500 ml), then dried with MgSO$_4$ and concentrated to give 13.0 grams of a yellow foam. This crude material was purified by column chromatography on silica gel with 0% to 5% MeOH/DCM to give compound 217 as a yellow foam (12.2 g, 68% yield). $^1$H NMR (400 MHz, DMSO-d$_6$) δ 1.12 (6H, t, J=7.2 Hz), 1.35 (2H, m), 1.73 (2H, m), 3.12 (2H, m), 3.44 (4H, q, J=7.1 Hz), 3.71 (1H, m, J=4.1 Hz), 3.97 (1H, m), 4.78 (1H, d, J=4.0 Hz), 6.54 (1H, d, J=2.8 Hz), 6.73 (1H, dd, J=2.4, 8.8 Hz), 7.48 (1H, d, J=9.2 Hz), 7.92 (1H, s). MS (ES+) m/z: [M+H]$^+$ calcd. for C$_{19}$H$_{24}$N$_2$O$_4$: 345.81. found: 345.81.

Example 18

Preparation of Compound 218

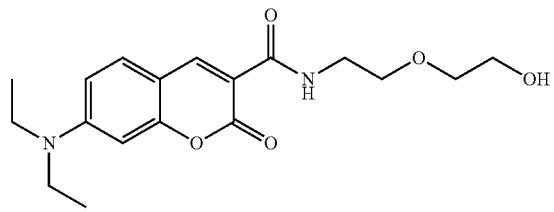

7-(diethylamino)-N-(2-(2-hydroxyethoxy)ethyl)-2-oxo-2H-chromene-3-carboxamide

The procedure of Example 17 was followed using aminoethoxyethanol in place of 4-hydroxy piperidine to give compound 218 as a pale yellow solid in 65% yield. $^1$H NMR (400 MHz, DMSO-d$_6$) δ 1.14 (6H, t, J=7.0 Hz), 3.49 (12H, m), 4.60 (1H, t, J=5.6 Hz), 6.61 (1H, d, J=2.0 Hz), 6.80 (1H, dd, J=2.4, 6.8 Hz), 7.68 (1H, d, J=8.8 Hz), 8.67 (1H, s), 8.77 (1H, t, J=5.4 Hz)MS (ES+) m/z: [M+H]$^+$ calcd. for C$_{18}$H$_{24}$N$_2$O$_5$: 349.18. found: 349.18.

Example 19

Preparation of Compound 219

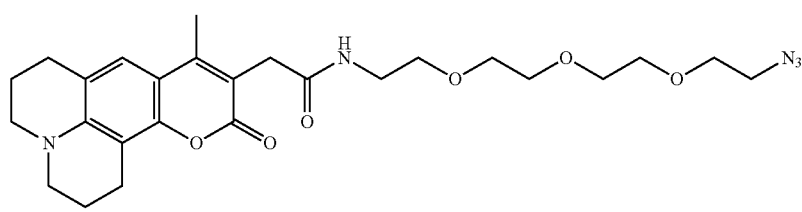

N-(2-(2-(2-(2-Azidoethoxy)ethoxy)ethoxy)ethyl)-2-(9-methyl-11-oxo-2,3,5,6,7,11-hexahydro-1H-pyrano[2,3-f]pyrido[3,2,1-ij]quinolin-10-yl)acetamide Compound 211 (2.05 g, 5 mmoles) and 2-(2-(2-(2-azidoethoxy)ethoxy)ethoxy)-ethanamine (1.42 g, 6.5 mmoles) were reacted in DMF (15 ml) in a round bottomed flask equipped with a magnetic stirrer. After stirring for 18 hours at RT the reaction mixture was concentrated. The residue was dissolved in DCM (75 ml), washed with 1N HCl (2×50 ml) and brine (75 ml). The organic phase was dried with MgSO$_4$ and concentrated to give an amber residue (2.59 g). This crude material was purified by column chromatography on silica gel with 0% to 2% MeOH/DCM to give compound 219 as a pale orange semisolid (1.84, 85% yield). $^1$H NMR (400 MHz, CDCl$_3$) δ 1.55-1.90 (2H, m), 1.97 (4H, quint, J=6.0 Hz), 2.44 (3H, s), 2.79 (2H, t, J=6.2 Hz), 2.88 (2H, t, J=6.6 Hz), 3.25 (4H, q, J=6.4 Hz), 3.39 (4H, quint, J=5.1 Hz), 3.53 (2H, t, J=5.2 Hz), 3.53 (2H, s), 3.55-3.80 (8H, m), 6.72 (1H, br t), 7.01 (1H, s). MS (ES+) m/z: [M+H]$^+$ calcd. for C$_{26}$H$_{35}$N$_5$O$_6$: 514.27. found: 514.27.

Example 20

Preparation of Compound 220

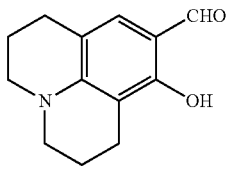

8-Hydroxy-1,2,3,5,6,7-hexahydropyrido[3,2,1-ij]quinoline-9-carbaldehyde, (8-hydroxy-julolidine-9-carbaldehyde)

A round bottomed flask equipped with a magnetic stirrer was charged with DMF (100 ml) and cooled in an icebath to 0-5° C. Phosphorus oxychloride (39.5 g, 257 mmoles) was added dropwise and the mixture was stirred for 30 minutes. 8-hydroxy-julolidine (34 g, 180 mmoles) dissolved in DMF (75 ml) was added dropwise and the mixture was allowed to gradually warm to RT. The mixture was heated to 85° C. in an oil bath for 1 hour. After cooling to RT the reaction was poured into ice (400 g) with stirring. After keeping at 4° C. overnight the solids were suction-filtered and washed with water (4×50 ml). The filtercake was dissolved in DCM (500 ml) and the solution washed with saturated sodium bicarbonate (100 ml). The aqueous wash was extracted with DCM (50 ml). The organic phases were combined, dried with MgSO$_4$ and concentrated to give compound 220 as a pale green crystalline solid (36.0 g, 92% yield). m.p. 72-73° C. $^1$H NMR 400 MHz, CDCl$_3$) δ 1.93 (4H, m, J=5.6 Hz), 2.68 (4H, t, J=6.4 Hz), 3.27 (4H, q, J=6.4 Hz), 6.84 (1H, s), 9.37 (1H, s), 11.81 (1H, s). MS (ES+) m/z: [M+H]$^+$ calcd. for C$_{13}$H$_{15}$NO$_2$: 218.12. found: 218.12.

Example 21

Preparation of Compound 221

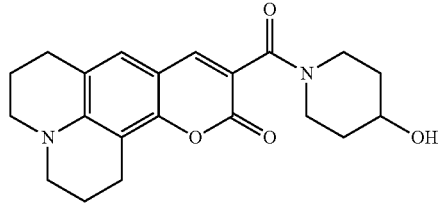

10-(4-hydroxypiperidine-1-carbonyl)-2,3,6,7-tetrahydro-1H-pyrano[2,3-f]pyrido[3,2,1-ij]quinolin-11(5H)-one The procedure of Example 17 was followed using compound 220 in place of 4-(diethylamino)-2-hydroxybenzaldehyde to give compound 221 as a yellow solid in 82% yield. $^1$H NMR (400 MHz, CDCl$_3$) δ 1.60 (2H, br s), 1.92 (2H, br s), 1.97 (4H, t, J=4.4 Hz), 2.75 (2H, t, J=5.0 Hz), 2.87 (2H, t, J=5 Hz), 3.22 (1H, m), 3.30 (4H, t, J=4.8 Hz), 3.36 (1H, m), 3.60 (1H, m), 3.95 (1H, m), 4.17 (1H, m), 6.88 (1H, s), 7.73, (1H, s). MS (ES+) m/z: [M+H]$^+$ calcd. for C$_{21}$H$_{24}$N$_2$O$_4$: 369.18. found: 369.18.

Example 22

Preparation of Compound 222

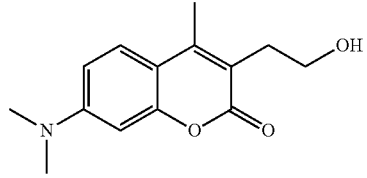

7-(Dimethylamino)-3-(2-hydroxyethyl)-4-methyl-2H-chromen-2-one

A round bottomed flask equipped with a magnetic stirrer and reflux condenser was charged with 3-dimethylaminophenol (10 g, 72.9 mmoles), α-acetyl-butyrolactone (10.3 g, 80.2 mmoles), zinc chloride (13.9 g, 102 mmoles) and absolute ethanol (100 ml). The reaction was refluxed for 2 hours. After cooling the reaction was concentrated and poured into water (600 mL) plus 1N HCl (120 ml). The mixture was extracted with DCM (3×200 ml). The organic phase was washed with water (2×500 ml) and brine (500 ml), dried with MgSO$_4$ and concentrated to give 9.40 grams of a reddish tan solid. This solid was recrystallized from IPA (25 ml) to give compound 222 as a light tan solid (3.96 g, 22% yield). m.p. 141-145° C. $^1$H NMR (400 MHz, DMSO-d$_6$) δ 2.34 (3H, s), 2.68 (2H, t, J=7.0 Hz), 2.99 (6H, s), 3.47 (2H, q, J=6.5 Hz), 4.65 (1H, t, J=5.8 Hz), 6.51 (1H, d, J=2.4 Hz), 6.71 (1H, dd, J=2.8, 9.2 Hz), 7.53 (1H, d, J=8.8 Hz). MS (ES+) m/z: [M+H]$^+$ calcd. for C$_{14}$H$_{17}$NO$_3$: 248.13. found: 248.13. Anal. calcd. for C$_{14}$H$_{17}$NO$_3$: C, 68.00; H, 6.93; N, 5.66. Found: C, 67.73; H, 6.74; N, 5.82.

Example 23

Preparation of Compound 223

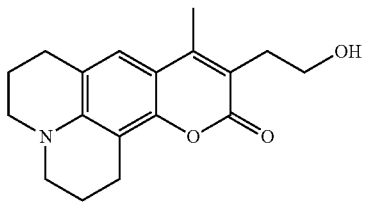

223

10-(2-hydroxyethyl)-9-methyl-2,3,6,7-tetrahydro-1H-pyrano[2,3-f]pyrido[3,2,1-ij]quinolin-11(5H)-one The procedure of Example 21 was followed using 8-hydroxy julolidine in place of 3-dimethyl-aminophenol to give compound 223 as a tan solid in 34% yield. m.p. 146-148° C. $^1$H NMR (400 MHz, DMSO-d$_6$) δ 1.87 (4H, q, J=6.0 Hz), 2.29 (3H, s), 2.66 (3H, t, J=7.2 Hz), 2.71 (3H, q, J=6.8 Hz), 3.20 (4H, q, J=6.0 Hz), 3.44 (1H, q, J=6.0 Hz), 4.62 (1H, t, J=5.6 Hz), 7.11 (1H, s). MS (ES+) m/z: [M+H]$^+$ calcd. for C$_{18}$H$_{21}$NO$_3$: 300.16. found: 300.16. Anal. calcd. for C$_{18}$H$_{21}$NO$_3$: C, 72.22; H, 7.07; N, 4.68. Found: C, 71.82; H, 7.07; N, 4.75.

Example 24

Preparation of Compound 224

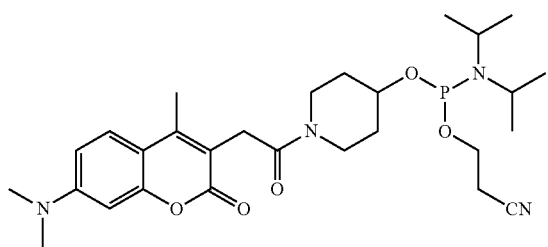

224

2-cyanoethyl(1-(2-(7-(dimethylamino)-4-methyl-2-oxo-2H-chromen-3-yl)acetyl)piperidin-4-yl)diisopropylphosphoramidite A round bottomed flask equipped with a magnetic stirrer was charged with compound 212 (6 g, 14.0 mmoles, 80% pure) and DMF (50 ml). 1H-Tetrazole (294 mg, 4.2 mmoles) was added to the suspension, followed by a solution of 3-((bis(diisopropylamino)phosphino)oxy)-propanenitrile (5.05 g, 16.8 mmoles) in DMF (15 ml). After stirring for 15 hours at RT additional 3-((bis(diisopropylamino)phosphino)oxy)propanenitrile (2.52 g, 8.4 mmoles) was added. After an additional 15 hours the solution was poured into saturated sodium bicarbonate solution (700 ml) and extracted with DCM (3×200 ml). The organic phase was washed with saturated sodium bicarbonate solution (2×400 ml) and brine (400 ml). Drying with MgSO$_4$ followed by concentration gave 11.7 grams of pale green syrup. This crude material was purified by column chromatography on alumina with 50% to 100% DCM/petroleum ether plus 1% TEA to give compound 224 as a pale yellow solid (4.58 g, 60% yield). $^1$H NMR (400 MHz, CDCl$_3$) δ 1.19 (12H, m), 1.25 (6H, m), 1.41 (3H, d, J=6.4 Hz), 1.6-1.9 (5H, m), 2.40 (3H, m), 2.64 (2H, m), 3.04 (6H, s), 3.5-3.9 (10H, m), 4.11 (2H, m) 6.50 (1H, d, J=2.8 Hz), 6.62 (1H, dd, J=2.4, 8.8 Hz), 7.45 (1H, d, J=8.8 Hz). $^{31}$P NMR (162 MHz, CDCl$_3$) δ 146.209, 146.397. MS (ES+) m/z: [M+H]$^+$ calcd. for C$_{28}$H$_{41}$N$_4$O$_5$P: 545.29. found: 545.29.

Example 25

Preparation of Compound 225

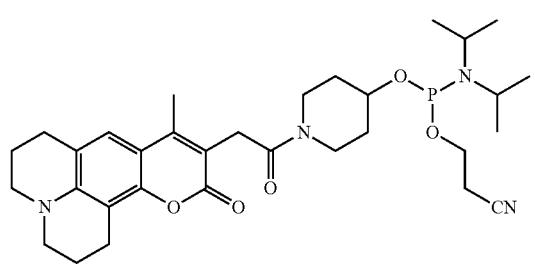

225

2-cyanoethyl(1-(2-(9-methyl-11-oxo-2,3,5,6,7,11-hexahydro-1H-pyrano[2,3-f]pyrido[3,2,1-ij]quinolin-10-yl)acetyl)piperidin-4-yl)diisopropylphosphoramidite The procedure of Example 24 was followed using compound 214 in place of compound 212 to give compound 225 as a yellow semisolid in 38% yield. $^1$H NMR (400 MHz, CDCl$_3$) δ 1.17-1.25 (12H, m), 1.30 (2H, d, J=6.8 Hz), 1.16-2.0 (4H, m), 1.97 (4H, m), 2.36 (3H, d, J=2.8 Hz), 2.64 (2H, dt, J=2.4 Hz), 2.78 (2H, t, J=6.2 Hz), 2.88 (2H, m), 3.23 (4H, m), 3.4-3.9 (10H, m), 7.02 (1H, s). $^{31}$P NMR (162 MHz, CDCl$_3$) δ 146.159, 146.329. MS (ES+) m/z: [M+H]$^+$ calcd. for C$_{32}$H$_{45}$N$_4$O$_5$P: 597.32. found: 496.20 (M-i-Pr$_2$N).

Example 26

Preparation of Compound 226

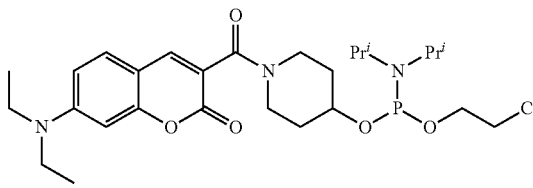

226

2-cyanoethyl(1-(7-(diethylamino)-2-oxo-2H-chromene-3-carbonyl)piperidin-4-yl)diisopropylphosphoramidite A round bottomed flask equipped with a magnetic stirrer was charged with compound 217 (8 g, 23.2 mmoles) and DCM (75 ml). 1H-Tetrazole (488 mg, 7.0 mmoles) was added, followed by a solution of 3-((bis(diisopropylamino) phosphino)oxy)propanenitrile (8.40 g, 27.9 mmoles) in DCM (25 ml). After stirring for 15 hours at RT the solution was washed with saturated sodium bicarbonate solution (2×250 ml), dried with MgSO$_4$ and concentrated to give 12.7 grams of golden foam. This crude material was purified by column chromatography on alumina with 50% to 100% DCM/petroleum ether plus 1% TEA to give compound 226 as a golden syrup (10.3 g, 81% yield). $^1$H NMR (400 MHz, CDCl$_3$) δ 1.1-1.3 (18H, m), 1.77 (2H, m), 1.92 (2H, m), 2.63 (2H, q, J=6.8 Hz), 3.35 (1H, m), 3.43 (4H, q, J=7.1 Hz), 3.62 (3H, m), 3.76 (2H, m), 3.83 (2H, m), 4.13 (1H, m), 6.47 (1H, d, J=2.4 Hz), 6.59 (1H, dd, J=2.8, 5.0 Hz), 7.29 (1H, m), 7.81 (1H, s). $^{31}$P NMR (162 MHz, CDCl$_3$) δ 146.208, 146.384. MS (ES+) m/z: [M+H]$^+$ calcd. for C$_{28}$H$_{41}$N$_4$O$_5$P: 545.29. found: 545.29.

Example 27

Preparation of Compound 227

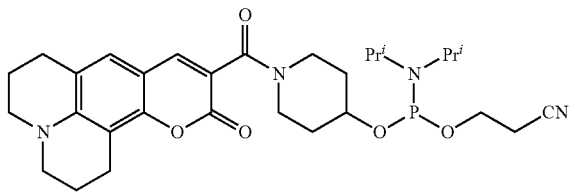

2-cyanoethyl(1-(11-oxo-2,3,5,6,7,11-hexahydro-1H-pyrano[2,3-f]pyrido[3,2,1-ij]quinoline-10-carbonyl) piperidin-4-yl)diisopropylphosphoramidite The procedure of Example 26 was followed using compound 221 in place of compound 217 to give compound 227 as an yellow foam in 40% yield. $^1$H NMR (400 MHz, DMSO-d$_6$) δ 0.97 (2H, br s), 1.14 (12H, m), 1.55 (2H, m), 1.76 (2H, m), 1.97 (4H, m), 2.73 (5H, m), 3.26 (4H, m), 3.43 (1H, m), 3.57 (1H, m), 3.71 (1H, m), 4.06 (1H, m), 7.06 (1H, s), 7.84 (1H, s). $^{31}$P NMR (162 MHz, DMSO-d$_6$) δ 145.985. MS (ES+) m/z: [M+H]$^+$ calcd. for C$_{30}$H$_{41}$N$_4$O$_5$P: 569.29. found: 569.29.

Example 28

Preparation of Compound 228

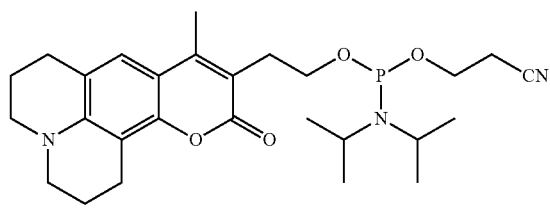

2-cyanoethyl(2-(9-methyl-11-oxo-2,3,5,6,7,11-hexahydro-1H-pyrano[2,3-]pyrido[3,2,1-ij]quinolin-10-yl)ethyl)diisopropylphosphoramidite The procedure of Example 18 was followed using compound 223 in place of compound 217 to give compound 228 as a pale yellow glass in 72% yield. $^1$H NMR (400 MHz, CDCl$_3$) δ 1.15 (12H, t, J=7.2 Hz), 1.98 (4H, m), 2.37 (3H, s), 2.60 (2H, t, J=6.8 Hz), 2.79 (2H, t, J=6.2 Hz), 2.88 (2H, t, J=6.4 Hz), 3.23 (4H, m), 3.56 (2H, m), 3.77 (4H, m) 7.01 (1H, s). $^{31}$P NMR (162 MHz, CDCl$_3$) δ 147.581. MS (ES+) m/z: [M+H]$^+$ calcd. for C$_{27}$H$_{38}$N$_3$O$_4$P: 500.27. found: 399.15 (M-i-Pr$_2$N).

Example 29

Solid Phase Synthesis of Oligonucleotides Labeled with Coumarin Phosphoramidite Synthesis Reagents For ammonia stable coumarin reagents (224, 225 or 228) the protecting groups on the exocyclic amine groups of A, C and G were benzoyl, acetyl and dimethylformamidine, respectively. For ammonia unstable coumarins (226 or 227) A, C and G were protected by phenoxyacetyl, acetyl and 4-isopropylphenoxyacetyl.

General Procedure: Oligonucleotides labeled with the coumarin phosphoramidite synthesis reagents were made at a 200 nm scale on 3'-glycolate CPGs (van der Laan, et. Al, Tetrahedron Lett. 38: 2252 (1997)) with cyanoethyl phosphoramidite monomers on a Biosearch 8700 or Expedite NAS 8900 automated DNA synthesizer. After the synthesis was complete, the 5' DMT group was removed (with 3% dichloroacetic acid in dichloromethane) and the synthesis column was washed with dry acetonitrile.

To couple the coumarin to the oligonucleotide, 100 mg of coumarin phosphoramidites were dissolved in acetonitrile or DCM (1500 ul). A portion (500 ul) of the solution was applied to the column with a 1 ml syringe. A companion syringe containing 0.25 M ethyl thiotetrazole or 0.45 M 1H-tetrazole in acetonitrile (500 ul) was attached to the other end of the column. The solutions were mixed over the CPG with the syringes, and allowed to stand for 10 min. This was process was repeated twice more with the rest of the phosphoramidite solution. The columns were put back on the DNA synthesizer and washed with acetonitrile followed by oxidizer solution (0.02 M iodine in a mixture of THF (70%):pyridine (20%):water (10%)). After 30 seconds, this solution was washed with acetonitrile and the contents of each column were expelled into 2 ml vials.

Example 30

Cleavage and Deprotection of Oligonucleotides on CPG

Procedure A (for ammonia stable oligonucleotides prepared from coumarin phosphoramidites 224, 225 or 228): The oligonucleotides on CPG were subjected to standard ammonia deprotection (1 ml concentrated NH$_4$OH, 60° C. 1-2 hours). The CPG was filtered out and the filtrate concentrated under vacuum to give the crude coumarin labeled oligonucleotide. The samples were dissolved in de-ionized water (1 ml) for HPLC and LCMS analysis. The samples were dissolved in qPCR buffer for spectral analysis.

Procedure B (for ammonia unstable oligonucleotides prepared from coumarin phosphoramidites 226 or 227): The oligonucleotides on CPG were treated with 1 ml of 50 mM K$_2$CO$_3$/MeOH overnight. The mixture was acidified with AcOH, the CPG was filtered out and the filtrate concentrated under vacuum to give the crude coumarin labeled oligonucleotide. The samples were dissolved in de-ionized water (1 ml) for HPLC and LCMS analysis. The samples were dissolved in qPCR buffer for spectral analysis.

Example 31

Purification of Crude Oligonucleotides

The modified oligonucleotides were purified by HPLC on a preparative RP-C18 column (10×100 mm, 5 uM, 130 Å, Xbridge) using the following conditions: A) triethylamine/acetic acid buffer (50 mM); B) acetonitrile; gradient 0-95% B over 10 min, flow rate 10 mL/min, UV/vis detection at 260 and 400 nm.

Example 32

Preparation of Oligonucleotide 232

Example 34

Preparation of Oligonucleotide 234

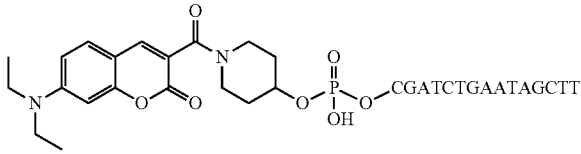

A DNA fragment 3'-TTCGATAAGTCTAGC-5' labeled at the 5' hydroxyl with compound 226 was prepared as described in example 29. The product 234 was cleaved from the support and deprotected as described in Procedure B in example 30. MS (ESI): calcd. 4974.4.

found: 4974.0. Abs/Em=418/490 nm in qPCR buffer.

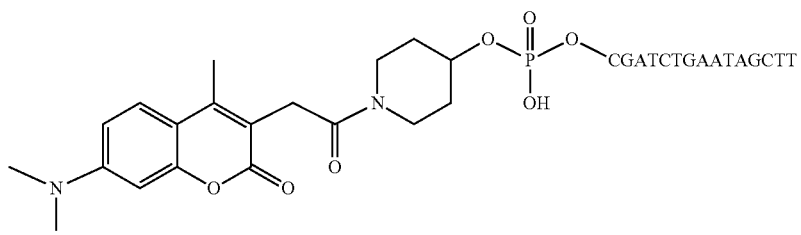

A DNA fragment 3'-TTCGATAAGTCTAGC-5' labeled at the 5' hydroxyl with compound 224 was prepared as described in example 29. The product 232 was cleaved from the support and deprotected as described in Procedure A in example 30. MS (ESI): calcd. 4973.4.

found: 4974.0. Abs/Em=380/488 nm in qPCR buffer.

Example 33

Preparation of Oligonucleotide 233

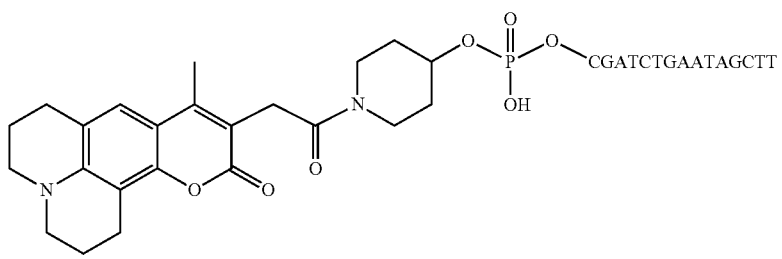

A DNA fragment 3'-TTCGATAAGTCTAGC-5' labeled at the 5' hydroxyl with compound 225 was prepared as described in example 29. The product 233 was cleaved from the support and deprotected as described in Procedure A in example 30. MS (ESI): calcd. 5026.5.

found: 5025.0. Abs/Em=398/498 nm in qPCR buffer.

Example 35

Preparation of Oligonucleotide 235

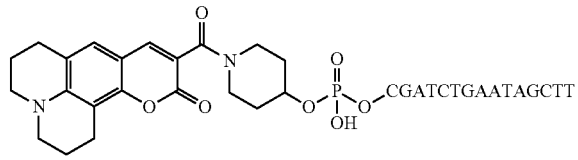

A DNA fragment 3'-TTCGATAAGTCTAGC-5' labeled at the 5' hydroxyl with 227 was prepared as described in example 29. The product 235 was cleaved from the support and deprotected as described in Procedure B in example 30. MS (ESI): calcd. 4997.4. found: 4998.0 Abs/Em=435/501 nm in qPCR buffer.

Example 36

Preparation of Oligonucleotide 236

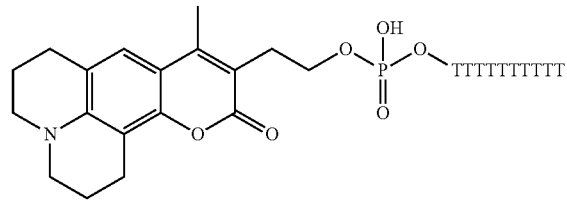

A DNA fragment 3'-TTTTTTTTTT-5' labeled at the 5' hydroxyl with compound 228 was prepared as described in example 29. The product 236 was cleaved from the support and deprotected as described in Procedure A in example 30. MS (ESI): calcd. 3341.1. found: 3341.0.

Results

TABLE 1

Spectral Properties of Coumarin Labeled Oligonucleotides in qPCR Buffer

| Compound | Absorbance | Emission |
|---|---|---|
| 232 | 380 nm | 480 nm |
| 233 | 398 nm | 498 nm |
| 234 | 418 nm | 490 nm |
| 235 | 435 nm | 501 nm |

Example 37

Preparation of Compound 237

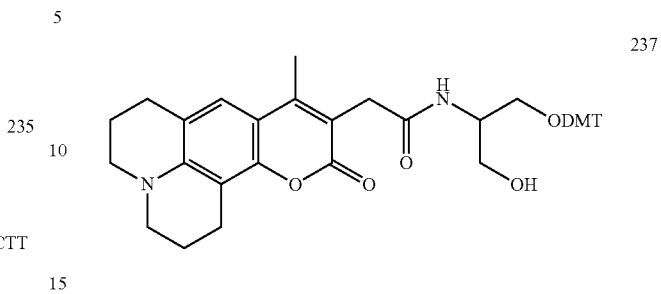

N-(1-(bis(4-methoxyphenyl)(phenyl)methoxy)-3-hydroxypropan-2-yl)-2-(9-methyl-11-oxo-2,3,5,6,7,11-hexahydro-1H-pyrano[2,3-f]pyrido[3,2,1-ij]quinolin-10-yl)acetamide Compound 210 (5 g, 12.2 mmoles) was added to a solution of serinol ODMT (6.00 g, 15.2 mmoles) and triethylamine (10 ml, 71.7 mmoles) in DMF (200 ml) in a round bottomed flask equipped with a magnetic stirrer. After stirring for 72 hours at RT the reaction was concentrated under vacuum to give a residue which was purified by column chromatography on silica gel with 2% pyridine/EtOAc to give compound 237 (7.2 g, 86% yield).

Example 38

Preparation of Compound 238

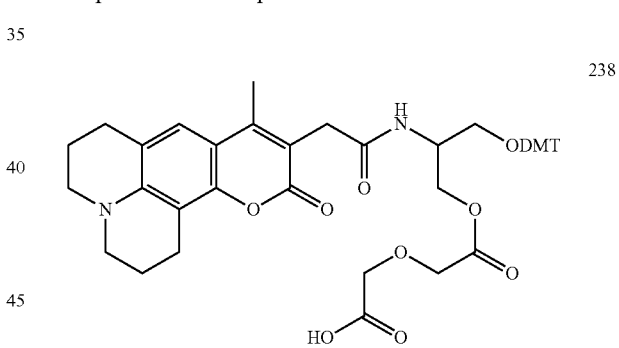

2-(2-(3-(bis(4-methoxyphenyl)(phenyl)methoxy)-2-(2-(9-methyl-11-oxo-2,3,5,6,7,11-hexahydro-1H-pyrano[2,3-f]pyrido[3,2,1-ij]quinolin-10-yl)acetamido)propoxy)-2-oxoethoxy)acetic acid Compound 237 (5 g, 7.26 mmoles) was dried by dissolving in pyridine in a round bottomed flask and concentrating under vacuum. Pyridine (200 ml) and diglycolic anhydride (5.00 g, 43.1 moles) were added. After stirring for 72 hours additional diglycolic anhydride (5.00 g, 43.1 moles) was added. The mixture was stirred for an additional 24 hours and concentrated under vacuum. The residue was dissolved in DCM (200 ml), washed with saturated $KH_2PO_4$ solution (200 ml), dried ($NaSO_4$) and concentrated under vacuum. The residue was purified by column chromatography on alumina with 5-30% MeOH/DCM containing 2% TEA and 2% pyridine to give compound 238 (6.00 g, 91% yield) as a TEA salt.

Example 39

Preparation of Compound 239

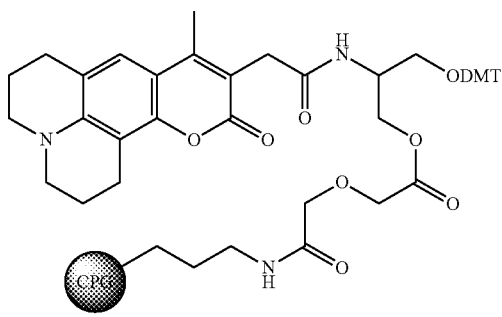

3-(bis(4-methoxyphenyl)(phenyl)methoxy)-2-(2-(9-methyl-11-oxo-2,3,5,6,7,11-hexahydro-1H-pyrano[2,3-f]pyrido[3,2,1-ij]quinolin-10-yl)acetamido)propyl 2-(2-oxo-2-((3-CPG-propyl)amino)ethoxy)acetate Compound 238 (3 g, 3.31 mmoles) was dissolved in DMF (75 ml). BOP (benzotriazol-1-yloxy-tris(dimethylamino)phosphanium hexafluorophosphate, 3 g, 6.78 mmoles), pyridine (10 ml) and aminopropyl CPG (10 g, 500 Å, 130 μmoles/g loading) were added. After the mixture sat at RT for 18 hours the CPG was rinsed with MeCN (3×100 ml). N-methylimidazole (239 M in THF, 50 ml) and acetic anhydride (50 ml) were added. After sitting at RT for 10 min the CPG was rinsed with MeCN (2×100 ml), MeOH (2×100 ml) and DCM (2×100 ml) and dried under vacuum to give the final derivatized CPG 239. Detritylation and colorometric quantification of a sample indicated a loading of 35 μmoles/g CPG.

Example 40

Preparation of Compound 240

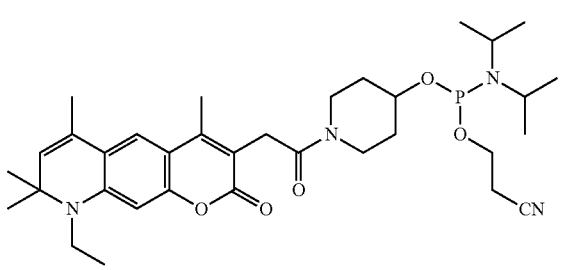

2-Cyanoethyl(1-(2-(9-ethyl-4,6,8,8-tetramethyl-2-oxo-8,9-dihydro-2H-pyrano[3,2-g]quinolin-3-yl)acetyl)piperidin-4-yl)diisopropylphosphoramidite A round bottomed flask equipped with a magnetic stirrer was charged with compound 216 (2.12 g, 5.0 mmoles) and DCM (30 mL). 1H-Tetrazole (195 mg, 1.5 mmoles) was added to the suspension, followed by a solution of 3-((bis(diisopropylamino)phosphino)oxy)-propanenitrile (3.32 g, 11 mmoles) in DCM (5 mL). After stirring for 3.5 hours at RT additional 3-((bis(diisopropylamino)phosphino)oxy)propanenitrile (2.00 g, 6.6 mmoles) was added. After an additional 15 hours the solution was poured into saturated sodium bicarbonate solution (250 mL) and extracted with DCM (3×100 mL). The organic phase was washed with saturated sodium bicarbonate solution (2×200 mL) and brine (300 mL). Drying with $Na_2SO_4$ followed by concentration gave 6.20 grams of pale yellow syrup. This crude material was purified by column chromatography on alumina with 50% to 100% DCM/petroleum ether plus 1% TEA to give compound 240 as a pale yellow syrup (1.74 g, 56% yield). MS (ES+) m/z: $[M+H]^+$ calcd. for $C_{34}H_{49}N_4O_5P$: 624.34. found: 523.22 (M-i-$Pr_2$N).

Example 41

Preparation of Compound 241

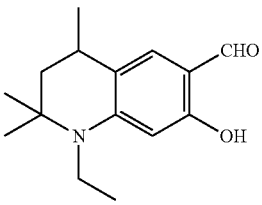

1-Ethyl-7-hydroxy-2,2,4-trimethyl-1,2,3,4-tetrahydroquinoline-6-carbaldehyde

1-Ethyl-2,2,4-trimethyl-1,2,3,4-tetrahydroquinolin-7-ol (21.9 g, 100 mmoles) was dissolved in acetic anhydride (70 mL) and heated at 100° C. under $N_2$ for 2 hours. This solution was concentrated. Water (150 mL) and DCM (100 mL) were added to the residue and the mixture was stirred for 30 minutes. The layers were separated. The aqueous layer was further extracted with DCM (2×150 mL). The organic extracts were combined, washed with water (2×500 mL), washed with brine (500 mL), dried ($MgSO_4$) and concentrated to give a syrup. $POCl_3$ was added slowly to DMF (60 mL) cooled in an icebath and the mixture was stirred for 30 min. The syrup from above was dissolved in DMF (25 mL) and added over 10 minutes to the $POCl_3$/DMF mixture. The icebath was removed and the reaction was stirred at RT for 2 hours and then heated to 100° C. for 1 hour. The reaction was cooled and poured into ice (250 g) with stirring. The mixture was extracted with DCM (2×250 mL) The organic extracts were combined, washed with water (500 mL), washed with brine (500 mL), dried ($MgSO_4$) and concentrated to give a dark green syrup (28.2 g). This crude material was purified by column chromatography on silica gel with 0 to 1% MeOH/DCM to give compound 241 as an amber syrup (22.7 g, 92% yield). MS (ES+) m/z: $[M+H]^+$ calcd. for $C_{15}H_{21}NO_2$: 247.16. found: 247.16.

Example 42

Preparation of Compound 242

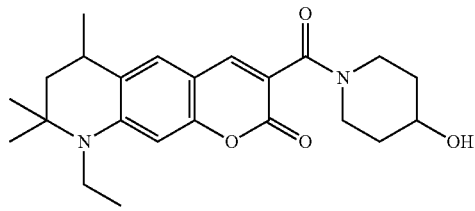

242

9-Ethyl-3-(4-hydroxypiperidine-1-carbonyl)-6,8,8-trimethyl-6,7,8,9-tetrahydro-2H-pyrano[3,2-g]quinolin-2-one Compound 241 (6.18 g, 25 mmoles), diethyl malonate (4.81 g, 30 mmoles), 4-hydroxypiperidine (9.10 g, 90 mmoles), piperidine (4 drops) and acetic acid (4 drops) were added to a vial equipped with a magnetic stirrer. The reaction was heated to 100° C. for 3.5 hours. After cooling the syrup was poured into water (300 mL) and extracted with DCM (3×150 mL). The organic phase was washed with water (2×200 mL), 1 M aqueous citric acid (3×200 mL) and brine (350 mL), then dried with MgSO$_4$ and concentrated to give 8.14 g dark amber foam. This crude material was purified by column chromatography on silica gel with 0% to 5% MeOH/DCM to give compound 242 as a golden foam (6.57 g, 66% yield). MS (ES+) m/z: [M+H]$^+$ calcd. for $C_{23}H_{30}N_2O_4$: 398.22. found: 398.22.

Example 43

Preparation of Compound 243

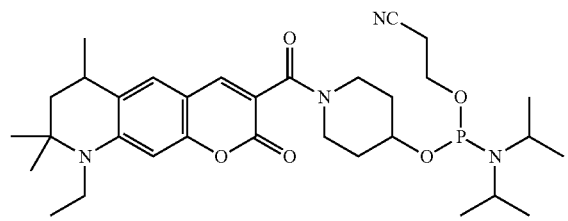

243

2-Cyanoethyl(1-(9-ethyl-6,8,8-trimethyl-2-oxo-6,7,8,9-tetrahydro-2H-pyrano[3,2-g]quinoline-3-carbonyl)piperidin-4-yl)diisopropylphosphoramidite A round bottomed flask equipped with a magnetic stirrer was charged with compound 242 (5.98 g, 15 mmoles) and MeCN (100 mL). 1H-Tetrazole (315 mg, 4.5 mmoles) was added, followed by a solution of 3-((bis(diisopropylamino)phosphino)oxy)propanenitrile (5.43 g, 18 mmoles) in MeCN (10 mL). After stirring for 15 hours at RT the solution was poured into saturated sodium bicarbonate solution (100 mL) and extracted with DCM (2×100 mL) The organic phase was washed with saturated sodium bicarbonate solution (200 mL) and brine (200 mL). Drying with Na$_2$SO$_4$ followed by concentration gave 8.66 grams of golden foam. This crude material was purified by column chromatography on alumina with 50% to 100% DCM/petroleum ether plus 1% TEA to give compound 243 as a yellow sticky foam (6.90 g, 77% yield). MS (ES+) m/z: [M+H]' calcd. for $C_{32}H_{47}N_4O_5P$: 598.33. found: 598.33.

Example 44

Preparation of Compound 244

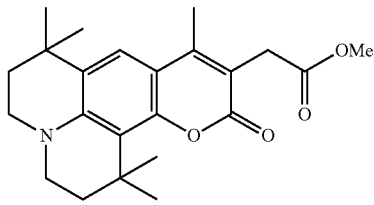

244

Methyl 2-(1,1,7,7,9-pentamethyl-11-oxo-2,3,5,6,7,11-hexahydro-1H-pyrano[2,3-f]pyrido[3,2,1-ij]quinolin-10-yl)acetate A round bottomed flask equipped with a magnetic stirrer was charged with 3-1,1,7,7-tetramethyl-1,2,3,5,6,7-hexahydropyrido[3,2,1-ij]quinolin-8-ol (24.5 g, 100 mmoles), dimethyl 2-acetylsuccinate (37.6 g, 200 mmoles) and zinc chloride (38.2 g, 280 mmoles). The mixture was heated to 120° C. for 48 hours and cooled. The reaction mass was partitioned between DCM (500 mL) and water (1 L) plus concentrated HCl (30 mL). The layers were separated and the aqueous phase was extracted with DCM (3×400 mL). The organic phases were combined and washed with water (1 L) plus concentrated HCl (30 mL), with plain water (1 L) and with brine (1 L). The organic phase was dried with MgSO$_4$ and concentrated to give 36.0 grams of a dark green syrup. This crude material was purified by column chromatography on silica gel with 0 to 2% MeOH/DCM to give a dark brown syrup which was dissolved in ether (400 mL), washed with 0.5 N KOH (2×200 mL, 100 mL), washed with brine (400 mL), dried (MgSO$_4$) and concentrated to give a dark brown foam (19.4 g). Recrystallization from IPA (30 mL) gave compound 244 as a yellow sticky foam (9.33 g, 24% yield). MS (ES+) m/z: [M+H]$^+$ calcd. for $C_{23}H_{29}NO_4$: 383.21. found: 383.21.

Example 45

Preparation of Compound 245

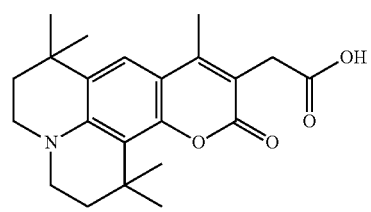

245

2-(1,1,7,7,9-Pentamethyl-11-oxo-2,3,5,6,7,11-hexahydro-1H-pyrano[2,3-f]pyrido[3,2,1-ij]quinolin-10-yl)acetic acid Further elution of the silica gel column purification from Example 44 above with 10% MeOH/DCM plus 1% AcOH gave compound 245 (5.00 g, 14% yield) as a dark green solid. Acidification of the base extracts from Example 44 above yielded an additional 3.20 grams of compound 245 (3.20 g, 9% yield). MS (ES+) m/z: [M+H]+ calcd. for $C_{22}H_{27}NO_4$: 369.19.
found: 369.19.

Example 46

Preparation of Compound 246

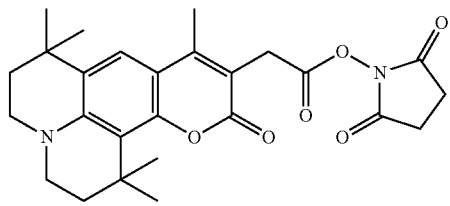

2,5-Dioxopyrrolidin-1-yl 2-(1,1,7,7,9-pentamethyl-11-oxo-2,3,5,6,7,11-hexahydro-1H-pyrano[2,3-f]pyrido[3,2,1-ij]quinolin-10-yl)acetate Compound 245 (8.10 g, 21.9 mmoles) was reacted with N,N'-disuccinimidyl carbonate (6.74 g, 26.3 mmol) and DIEA (3.26 g, 25.2 mmol) in DMF (100 mL). After 15 hours stirring at RT the mixture was poured into cold 40 mM HCl (1.3 L). Suction filtration gave a yellow solid which was washed with water (2×50 mL) and dried to give compound 246 as an amber solid (8.70 g, 85% yield).

Example 47

Preparation of Compound 247

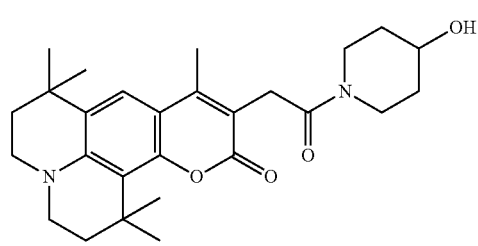

10-(2-(4-Hydroxypiperidin-1-yl)-2-oxoethyl)-1,1,7,7,9-pentamethyl-2,3,6,7-tetrahydro-1H-pyrano[2,3-f]pyrido[3,2,1-ij]quinolin-11(5H)-one Compound 246 (7.00 g, 15 mmoles) and 4-hydroxypiperidine (1.82 g, 18 mmoles) were dissolved in DMF (40 mL) in a round bottomed flask equipped with a magnetic stirrer. After stirring for 2.5 hours at RT, the flask was kept at −20° C. overnight. The precipitate was filtered out and filtrate was poured into water (800 mL). The mixture was extracted with DCM (4×100 mL), washed with water (400 mL), washed with brine (400 mL), dried (MgSO4) and concentrated to give a black foam (6.56 g). This crude material was purified by column chromatography on silica gel with 0 to 5% MeOH/DCM to give compound 247 as a dark brown foam (3.94 g, 58% yield). MS (ES+) m/z: [M+H]+ calcd. for $C_{27}H_{36}N_2O_4$: 452.27. found: 452.27.

Example 48

Preparation of Compound 248

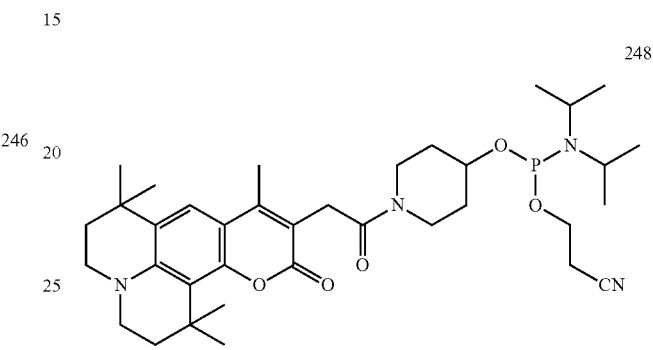

2-Cyanoethyl(1-(2-(1,1,7,7,9-pentamethyl-11-oxo-2,3,5,6,7,11-hexahydro-1H-pyrano[2,3-f]pyrido[3,2,1-ij]quinolin-10-yl)acetyl)piperidin-4-yl)diisopropylphosphoramidite Following the procedure of Example 40 with compound 247 (3.50 g, 7.73 mmoles) in place of compound 216 and MeCN in place of DCM gave compound 248 (4.75 g, 94% yield) as an amber syrup. MS (ES+) m/z: [M+H]+ calcd. for $C_{36}H_{53}N_4O_5P$: 652.38. found: 551.26 (M-i-Pr2N).

Example 49

Preparation of Compound 249

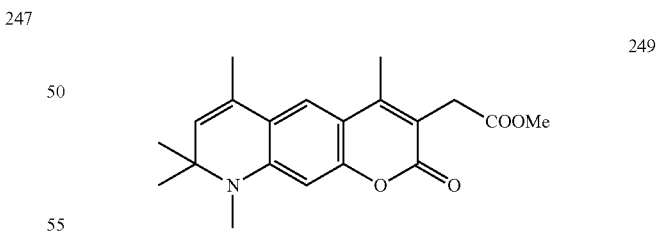

Methyl 2-(4,6,8,8,9-pentamethyl-2-oxo-8,9-dihydro-2H-pyrano[3,2-g]quinolin-3-yl)acetate The procedure of Example 6 was followed using 1,2,2,4-tetramethyl-1,2-dihydroquinolin-7-ol (43.2 g, 228 mmoles) in place of 1-ethyl-2,2,4-trimethyl-1,2-dihydroquinolin-7-ol hydrobromide to give compound 249 as a yellow solid (26.2 g, 34% yield). MS (ES+) m/z: [M+H]+ calcd. for $C_{20}H_{23}NO_4$: 341.16. found: 341.16.

Example 50

Preparation of Compound 250

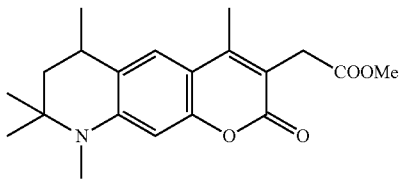

Methyl 2-(4,6,8,8,9-pentamethyl-2-oxo-6,7,8,9-tetrahydro-2H-pyrano[3,2-g]quinolin-3-yl)acetate Compound 249 (8.55 g, 25 mmoles) was dissolved in DCM (200 mL). Triethylsilane (29.1 g, 250 mmoles) and trifluoracetic acid (57.0 g, 500 mmoles) were added and the mixture refluxed for 13 hours. The mixture was cooled and washed with 1 N NaOH (500 mL), water (500 mL) and brine (500 mL). Drying (MgSO$_4$) and concentration gave compound 250 (8.59 g, 100% yield) as a pale tan solid. MS (ES+) m/z: [M+H]$^+$ calcd. for C$_{20}$H$_{25}$NO$_4$: 343.18. found: 343.18.

Example 51

Preparation of Compound 251

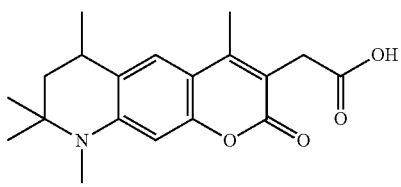

2-(4,6,8,8,9-Pentamethyl-2-oxo-6,7,8,9-tetrahydro-2H-pyrano[3,2-g]quinolin-3-yl)acetic acid Procedure B of Example 3 was followed using compound 250 (6.87 g, 20 mmoles) in place of compound 202 to give compound 251 (5.09 g, 77% yield) as a yellow solid. MS (ES+) m/z: [M+H]$^+$ calcd. for C$_{19}$H$_{23}$NO$_4$: 329.16. found: 329.16.

Example 52

Preparation of Compound 252

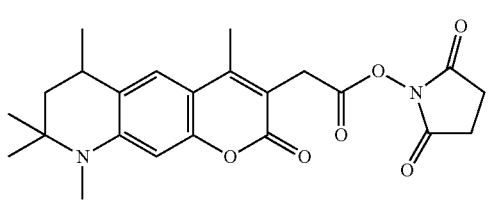

2,5-Dioxopyrrolidin-1-yl 2-(4,6,8,8,9-pentamethyl-2-oxo-6,7,8,9-tetrahydro-2H-pyrano[3,2-g]quinolin-3-yl)acetate The procedure of Example 46 was followed using compound 251 (3.95 g, 12 mmoles) in place of compound 245 to give compound 252 (4.56 g, 89% yield) as a yellow solid.

Example 53

Preparation of Compound 253

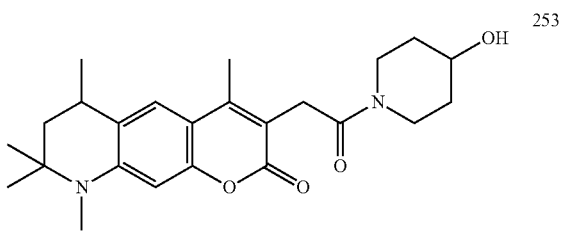 [SMILES: Cc1c(CC(=O)N2CCC(O)CC2)c(=O)oc2cc3c(cc12)C(C)CC(C)(C)N3C]

3-(2-(4-Hydroxypiperidin-1-yl)-2-oxoethyl)-4,6,8,8,9-pentamethyl-6,7,8,9-tetrahydro-2H-pyrano[3,2-g]quinolin-2-one Following the procedure of Example 16 with compound 252 (4.00 g, 9.38 mmoles) in place of compound 211 gave compound 253 (3.90 g, 100% yield) as a tan solid. MS (ES+) m/z: [M+H]$^+$ calcd. for C$_{24}$H$_{32}$N$_2$O$_4$: 412.24. found: 412.24.

Example 54

Preparation of Compound 254

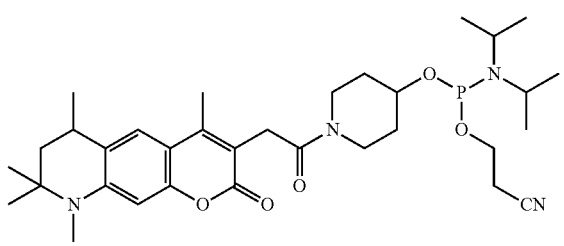

2-Cyanoethyl(1-(2-(4,6,8,8,9-pentamethyl-2-oxo-6,7,8,9-tetrahydro-2H-pyrano[3,2-g]quinolin-3-yl)acetyl)piperidin-4-yl)diisopropylphosphoramidite Following the procedure of Example 40 with compound 253 (3.50 g, 8.48 mmoles) in place of compound 216 and MeCN in place of DCM gave compound 254 (3.90 g, 75% yield) as a golden foam. MS (ES+) m/z: [M+H]$^+$ calcd. for C$_{33}$H$_{49}$N$_4$O$_5$P: 612.34. found: 612.34.

Example 55

Preparation of Compound 255

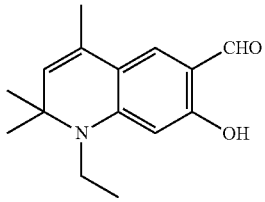

1-Ethyl-7-hydroxy-2,2,4-trimethyl-1,2-dihydroquinoline-6-carbaldehyde

Following the procedure of Example 41 with compound 1-ethyl-2,2,4-trimethyl-1,2-dihydroquinolin-7-ol (21.7 g, 100 mmoles) in place of 1-ethyl-2,2,4-trimethyl-1,2,3,4-tetrahydroquinolin-7-ol gave compound 255 (12.1 g, 50% yield) as a black syrup. MS (ES+) m/z: [M+H]$^+$ calcd. for $C_{15}H_{19}NO_2$: 245.14. found: 245.14.

Example 56

Preparation of Compound 256

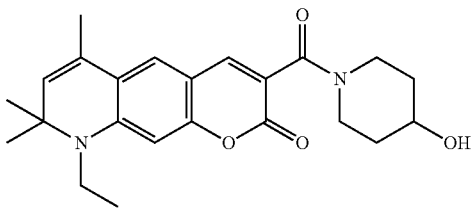

9-Ethyl-3-(4-hydroxypiperidine-1-carbonyl)-6,8,8-trimethyl-8,9-dihydro-2H-pyrano[3,2-]quinolin-2-one Following the procedure of Example 42 with compound 255 (8.52 g, 29.7 mmoles) in place of compound 241 gave compound 256 (9.52 g, 51% yield) as a dark amber foam. MS (ES+) m/z: [M+H]$^+$ calcd. for $C_{23}H_{28}N_2O_4$: 396.20. found: 396.20.

Example 57

Preparation of Compound 257

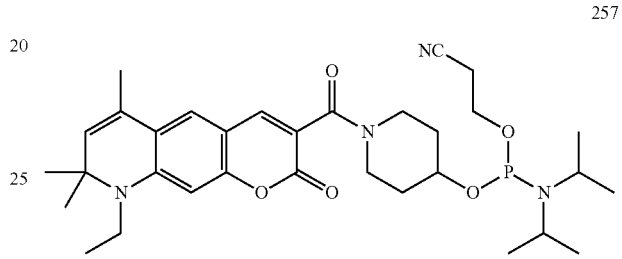

2-Cyanoethyl(1-(9-ethyl-6,8,8-trimethyl-2-oxo-8,9-dihydro-2H-pyrano[3,2-g]quinoline-3-carbonyl)piperidin-4-yl)diisopropylphosphoramidite Following the procedure of Example 43 with compound 256 (2.97, 7.5 mmoles) in place of compound 242 gave compound 257 (3.62 g, 80% yield) as an orange foam. MS (ES+) m/z: [M+H]$^+$ calcd. for $C_{32}H_{45}N_4O_5P$: 596.31. found: 596.31.

---

The invention claimed is:
1. A compound of Structure 15, 16 or 17:

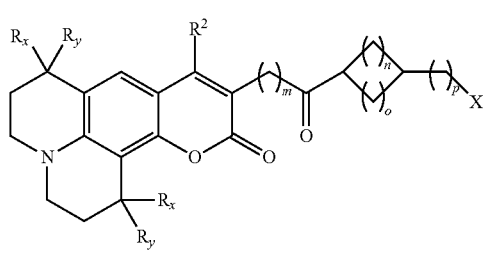

Structure 15

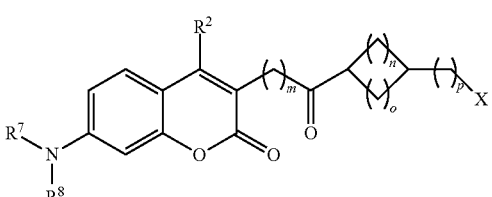

Structure 16

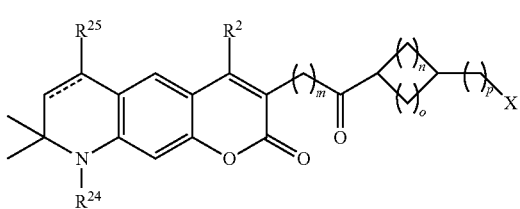

Structure 17 where
m is 1, 2, 3, 4, 5, 6, 7, 8, 9 or 10;
n is 1, 2 or 3;
o is 0, 1, 2, or 3;
p is 0, 1, 2, 3, 4, 5, 6, 7, 8, 9, or 10
$R^2$ is selected from a group consisting of —H or —CH$_3$;
X is —OH, —NH$_2$, —SH, —OR$^{11}$ —NHR$^{12}$ —NR$^{13}$R$^{14}$ —OC(O)R$^{15}$ —NHC(O)R$^{16}$, SC(O)R$^{17}$, —C(O)OH, —C(O)OR$^{18}$, —C(O)NHR$^{19}$, —C(O)NR$^{20}$R$^{21}$, —N$_3$;
$R^{11}$, $R^{12}$, $R^{13}$, $R^{14}$, $R^{15}$, $R^{16}$, $R^{17}$, $R^{18}$, $R^{19}$, $R^{20}$, and $R^{21}$, are independently selected from (C$_1$-C$_8$)alkyl, (C$_1$-C$_8$)substituted alkyl, —CH$_2$CH(OH)CH$_2$(OH), —CH(CH$_2$OH)$_2$, —CH$_2$CCH, —(CH$_2$CH$_2$O)a —CH$_2$CH$_2$OH where a is 1, 2, 3, 4, 5, 6, 7, 8, 9 or 10, —P(NR$^{22}$R$^{23}$)OCH$_2$CH$_2$-EWG, —P(O)(O$^-$)-Oligonucleotide, —(CH$^2$)$_b$CC-Nucleoside, —(CH$_2$)$_b$CC-[Nucleoside Triphosphate], —(CH$_2$)$_b$-Nucleoside, —(CH$_2$)$_b$-[Nucleoside Triphosphate], —(CH$_2$)$_b$NH-Nucleoside, —(CH$_2$)$_b$NH-[Nucleoside Triphosphate], —(CH$_2$)$_b$NHC(O)(CH$_2$)$_b$-Nucleoside, and —(CH$_2$)$_b$NHC(O)(CH$_2$)$_b$-[Nucleoside Triphosphate], where b is 1, 2, 3, 4, 5, 6, 7, 8, 9 or 10;
EWG is an electron withdrawing group; and
$R^{22}$ and $R^{23}$ are independently selected from —CH$_3$, —CH$_2$CH$_3$, —CH(CH$_3$)$_2$ or $R^{22}$ and $R^{23}$ together form a heterocycle; and
in the compound of Structure 15, $R_x$ and $R_y$ are independently H or CH$_3$,
in the compound of Structure 16, $R^7$ and $R^8$ are independently selected from H, (C$_1$-C$_8$) alkyl, (C$_1$-C$_8$)substituted alkyl, or $R^7$ and $R^8$ together form a five-, six-, or seven-membered heterocycle; and in the compound of Structure 17, $R^{24}$ is (C$_1$-C$_8$)alkyl or (C$_1$-C$_8$)substituted alkyl;
$R^{25}$ is (C$_1$-C$_8$)alkyl, (C$_1$-C$_8$)substituted alkyl or CH$_2$SO$_3$H; and
the dashed line represents an optional double bond.

2. The compound according to claim 1, wherein m is 1, 2 or 3, n is 1 or 2, o is 1 or 2, and p is 0, 1, 2 or 3.

3. The compound according to claim 1, wherein X is —OH, —OR$^{11}$, or OC(O)R$^{15}$.

4. A compound of Structure 14:

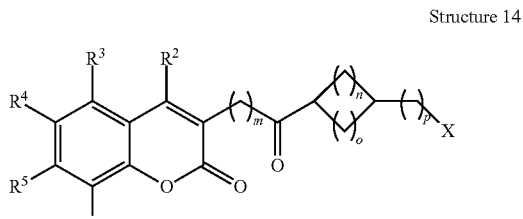

Structure 14 where
m is 0;
n is 1, 2 or 3;
o is 1, 2, or 3;
p is 0, 1, 2, 3, 4, 5, 6, 7, 8, 9, or 10
$R^2$ is selected from a group consisting of —H, or —CH$_3$;
$R^3$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$) substituted alkylthio, (C$_1$-C$_8$) alkoxy, (C$_1$-C$_8$)substituted alkoxy, —NR$^7$R$^8$ where $R^7$ and $R^8$ are independently selected from H, (C$_1$-C$_8$)alkyl or $R^7$ and $R^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or $R^3$ together with $R^4$ form a five- or six-membered carbocyclic or heterocyclic ring or substituted heterocyclic ring;
$R^4$ is selected from a group consisting of —H, -halogen, —CF$_3$, —OH, —NH$_2$, —CCH, —CN, —NO$_2$, (C$_1$-C$_8$)substituted alkyl, (C$_1$-C$_8$)alkylthio, (C$_1$-C$_8$) substituted alkylthio, (C$_1$-C$_8$)alkoxy, (C$_1$-C$_8$)substituted alkoxy, —NR$^7$R$^8$ where $R^7$ and $R^8$ are independently selected from H, (C$_1$-C$_8$)alkyl or $R^7$ and $R^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or $R^4$ together with $R^5$ form a five- or six-membered carbocyclic or heterocyclic ring having nitrogen as a heteroatom or substituted heterocyclic ring having nitrogen as a heteroatom;
$R^5$ is selected from a group consisting of —H, -halogen, —CF$_3$, —OH, —NH$_2$, —CCH, —CN, —NO$_2$, (C$_1$-C$_8$)alkyl, (C$_1$-C$_8$)substituted alkyl, (C$_1$-C$_8$)alkylthio, (C$_1$-C$_8$) substituted alkylthio, (C$_1$-C$_8$) alkoxy, (C$_1$-C$_8$)substituted alkoxy, —NR$^7$R$^8$ where $R^7$ and $R^8$ are independently selected from H, (C$_1$-C$_8$)alkyl or $R^7$ and $R^8$ together form a four-, five-, six-, or seven-membered heterocycle, (C$_1$-C$_8$)heteroalkyl, (C$_1$-C$_8$)substituted heteroalkyl, aryl, substituted aryl, heteroaryl, substituted heteroaryl, or $R^5$ together with $R^6$ form a five- or six-membered carbocyclic or heterocyclic ring or substituted heterocyclic ring; or $R^4$, $R^5$ and $R^6$ together form fused carbocyclic or heterocyclic ring systems or substituted heterocyclic ring systems having five- or six-membered rings;

$R^6$ is selected from a group consisting of —H, -halogen, —$CF_3$, —OH, —$NH_2$, —CCH, —CN, —$NO_2$, ($C_1$-$C_8$)alkyl, ($C_1$-$C_8$)substituted alkyl, ($C_1$-$C_8$)alkylthio, ($C_1$-$C_8$) substituted alkylthio, ($C_1$-$C_8$) alkoxy, ($C_1$-$C_8$)substituted alkoxy, —$NR^7R^8$ where $R^7$ and $R^8$ are independently selected from H, ($C_1$-$C_8$)alkyl or $R^7$ and $R^8$ together form a four-, five-, six-, or seven-membered heterocycle, ($C_1$-$C_8$)heteroalkyl, ($C_1$-$C_8$)substituted heteroalkyl, aryl, substituted aryl, heteroaryl, substituted heteroaryl;

X is selected from —OH —$NH_2$ —SH —$OR^{11}$ —$NHR^{12}$ —$NR^{13}R^{14}$ —$OC(O)R^{15}$ —$NHC(O)R^{16}$ —$SC(O)R^{17}$, —C(O)OH, —$C(O)OR^{18}$, —C(O)$NHR^{19}$, —$C(O)NR^{20}R^{21}$, —$N_3$;

$R^{11}$, $R^{12}$, $R^{13}$, $R^{14}$, $R^{15}$, $R^{16}$, $R^{17}$, $R^{18}$, $R^{19}$, $R^{20}$, and $R^{21}$, are independently selected from ($C_1$-$C_8$)alkyl, ($C_1$-$C_8$)substituted alkyl, —$CH_2CH(OH)CH_2(OH)$, —$CH(CH_2OH)_2$, —$CH_2CCH$, —($CH_2CH_2O$)a—$CH_2CH_2OH$ where a is 1, 2, 3, 4, 5, 6, 7, 8, 9 or 10, —$P(NR^{22}R^{23})OCH_2CH_2$-EWG, —$P(O)(O^-)$-Oligonucleotide, —$(CH^2)_b$CC-Nucleoside, —$(CH_2)_b$CC -[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O)$(CH_2)_b$-[Nucleoside Triphosphate], where b is 1, 2, 3, 4, 5, 6, 7, 8, 9 or 10;

EWG is an electron withdrawing group; and $R^{22}$, and $R^{23}$, are independently selected from —$CH_3$, —$CH_2CH_3$, —$CH(CH_3)_2$ or $R^{22}$ and $R^{23}$ together form a heterocycle.

5. The compound according to claim 4, wherein $R^3$ is —H or ($C_1$-$C_8$)alkyl.

6. The compound according to claim 5, wherein X is —OH, —$OR^{11}$, or $OC(O)R^{15}$.

7. The compound according to claim 6, wherein $R^4$ is —H or $R^4$ together with $R^5$ form a five- or six-membered carbocyclic or heterocyclic ring.

8. A compound of Structure 14:

Structure 14

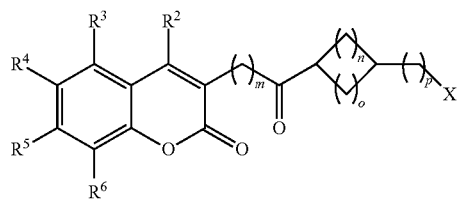

where
m is 0;
n is 0;
o is 0;
p is 3, 4, 5, 6, 7, 8, 9, or 10
$R^2$ is selected from a group consisting of —H, or —$CH_3$;
$R^3$ is selected from a group consisting of —H, -halogen;

$R^4$ is selected from a group consisting of —H, -halogen, —$CF_3$, —OH, —$NH_2$, —CCH, —CN, —$NO_2$, ($C_1$-$C_8$)alkyl, ($C_1$-$C_8$)substituted alkyl, ($C_1C_8$)alkylthio, ($C_1$-$C_8$) substituted alkylthio, ($C_1$-$C_8$)alkoxy, ($C_1C_8$)substituted alkoxy, -$NR^7R^8$ where $R^7$ and $R^8$ are independently selected from H, ($C_1$-$C_8$)alkyl or $R^7$ and $R^8$together form a four-, five-, six-, or seven-membered heterocycle, ($C_1$-$C_8$)heteroalkyl, ($C_1$-$C_8$) substituted heteroalkyl, aryl, substituted aryl, heteroaryl, substituted heteroaryl, or $R^4$ together with $R^5$ form a five- or six-membered carbocyclic or heterocyclic ring having nitrogen as a heteroatom or substituted heterocyclic ring having nitrogen as a heteroatom;

$R^5$ is selected from a group consisting of —H, -halogen, —$CF_3$, —OH, —$NH_2$, —CCH, —CN, —$NO_2$, ($C_1$-$C_8$)alkyl, ($C_1$-$C_8$)substituted alkyl, ($C_1C_8$)alkylthio, ($C_1$-$C_8$) substituted alkylthio, ($C_1$-$C_8$)alkoxy, ($C_1C_8$)substituted alkoxy, —$NR^7R^8$ where $R^7$ and $R^8$ are independently selected from H, ($C_1$-$C_8$)alkyl or $R^7$ and $R^8$together form a four-, five-, six-, or seven-membered heterocycle, ($C_1$-$C_8$)heteroalkyl, ($C_1$-$C_8$) substituted heteroalkyl, aryl, substituted aryl, heteroaryl, substituted heteroaryl, or $R^5$ together with $R^6$ form a five- or six-membered carbocyclic or heterocyclic ring or substituted heterocyclic ring; or $R^4$, $R^5$ and $R^6$ together form fused carbocyclic or heterocyclic ring systems or substituted heterocyclic ring systems having five- or six-membered rings;

$R^6$ is selected from a group consisting of —H, -halogen, —$CF_3$, —OH, —$NH_2$,—CCH, —CN, —$NO_2$, ($C_1$-$C_8$)alkyl, ($C_1$-$C_8$)substituted alkyl, ($C_1$-$C_8$)alkylthio, ($C_1$-$C_8$) substituted alkylthio, ($C_1$-$C_8$) alkoxy, ($C_1$-$C_8$)substituted alkoxy, —$NR^7R^8$ where $R^7$ and $R^8$ are independently selected from H, ($C_1$-$C_8$)alkyl or $R^7$ and $R^8$ together form a four-, five-, six-, or seven-membered heterocycle, ($C_1$-$C_8$)heteroalkyl, ($C_1$-$C_8$)substituted heteroalkyl, aryl, substituted aryl, heteroaryl, substituted heteroaryl;

X is selected from —OH, —$OR^{11}$ and —$OC(O)R^{15}$—;

$R^{11}$, and $R^{15}$, are independently selected from ($C_1$-$C_8$) alkyl, ($C_1$-$C_8$)substituted alkyl, —$CH_2CH(OH)CH_2$(OH), —$CH(CH_2OH)_2$, —$CH_2CCH$, —($CH_2CH2O$)a—$CH_2CH_2OH$ where a is 1, 2, 3, 4, 5, 6, 7, 8, 9 or 10, —$P(NR^{22}R^{23})OCH_2CH_2$-EWG, —$P(O)(O^-)$-Oligonucleotide, —$(CH_2)_b$CC-Nucleoside, —$(CH_2)_b$CC -[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)$(CH_2)_b$-Nucleoside, —$(CH_2)_b$NHC(O)$(CH_2)_b$-[Nucleoside Triphosphate], where b is 1, 2, 3, 4, 5, 6, 7, 8, 9 or 10;

EWG is an electron withdrawing group; and $R^{22}$, and $R^{23}$, are independently selected from —$CH_3$, —$CH_2CH_3$, —$CH(CH_3)_2$, or $R^{22}$ and $R^{23}$ together form a heterocycle.

9. The compound according to claim 8, wherein $R^4$ is —H or $R^4$ together with $R^5$ form a five- or six-membered carbocyclic or heterocyclic ring.

10. The compound according to claim 1, wherein X is —$OR^{11}$ and $R^{11}$ represents —$P(NR^{22}R^{23})OCH_2CH_2$-EWG, wherein EWG is an electron withdrawing group and $R^{22}$, and $R^{23}$ are independently selected from —$CH_3$, —$CH_2CH_3$, —$CH(CH_3)_2$, or $R^{22}$ and $R^{23}$ together form a heterocycle.

11. The compound according to claim 1, wherein the compound is of Structure 15.

12. The compound according to claim 1, wherein the compound is of Structure 16.

13. The compound according to claim 1, wherein the compound is of Structure 17.

14. The compound according to claim 1, wherein the compounds of structure 15 or 16, X is —$NH_2$, —$NHR^{12}$, —$NR^{13}R^{14}$, —$NHC(O)R^{16}$.

15. The compound according to claim 1, wherein, in the compound of structure 16, $R^7$ and $R^8$ are independently selected from H or ($C_1$-$C_8$)alkyl.

16. The compound according to claim 1, wherein, in the compound of structure 17, $R^{24}$ and $R^{25}$ are ($C_1$-$C_8$)alkyl.

17. A compound of Structure 27, 28 or 29

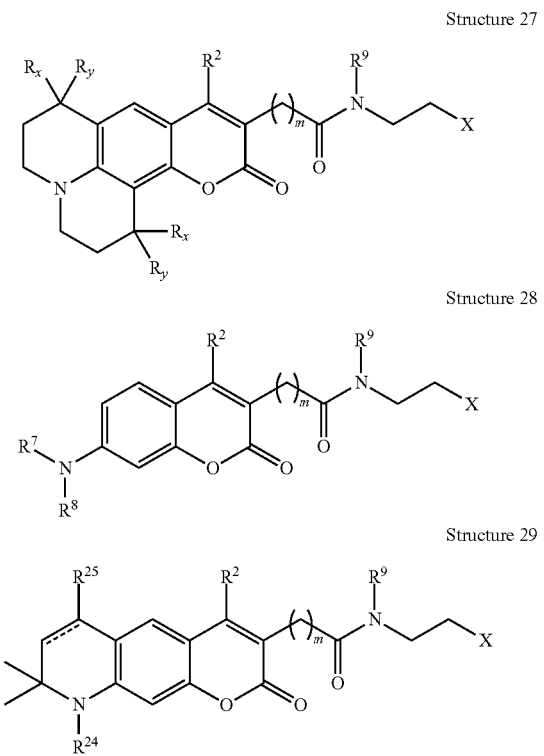

Structure 27

Structure 28

Structure 29 where
m is 1, 2, 3, 4, 5, 6, 7, 8, 9 or 10,
$R^2$ is selected from a group consisting of —H or -CH3;
$R^9$ is —CH3, —$CH_2CH_3$, —$CH(CH_3)_2$;
X is —OH, —NH2, —SH, —$OR^{11}$, —$NHR^{12}$, —$NR^{13}R^{14}$, —$OC(O)R^{15}$, —$NHC(O)R^{16}$, —$SC(O)R^{17}$, —C(O)OH, —$C(O)OR^{18}$, —$C(O)NHR^{19}$, —$C(O)NR^{20}R^{21}$, —$N_3$;
$R^{11}$, $R^{12}$, $R^{13}$, $R^{14}$, $R^{15}$, $R^{16}$, $R^{17}$, $R^{18}$, $R^{19}$, $R^{20}$ and $R^{21}$ are independently selected from ($C_1$-$C_8$)alkyl, ($C_1$-$C_8$)substituted alkyl, —$CH_2CH(OH)CH_2(OH)$, —$CH(CH_2OH)_2$, —$CH_2CCH$, —$(CH_2CH_2O)_a$-$CH_2CH_2OH$ where a is 1, 2, 3, 4, 5, 6, 7, 8, 9 or 10, —$P(NR_{22}R_{23})OCH_2CH_2$-EWG, —P(O)(O—)-Oligonucleotide, —$(CH_2)_b$CC-Nucleoside, —$(CH_2)_b$CC-[Nucleoside Triphosphate], —$(CH_2)_b$-Nucleoside, —$(CH_2)_b$-[Nucleoside Triphosphate], —$(CH_2)_b$NH-Nucleoside, —$(CH_2)_b$NH-[Nucleoside Triphosphate], —$(CH_2)_b$NHC(O)(CH2)_b$-Nucleoside, —$(CH_2)_b$NHC(O)$(CH_2)_b$-[Nucleoside Triphosphate], where b is 1, 2, 3, 4, 5, 6, 7, 8, 9 or 10,
EWG is an electron withdrawing group,
$R_x$ and $R_y$ are independently H and $CH_3$;
$R^{22}$ and $R^{23}$ are independently selected from —$CH_3$, —$CH_2CH_3$, —$CH(CH_3)_2$ or $R^{22}$ and $R^{23}$ together form a heterocycle; and
in the compound of Structure 27, $R_x$ and $R_y$ are independently H and $CH_3$;
in the compound of Structure 28, $R^7$ and $R^8$ are independently selected from H, ($C_1$-$C_8$)alkyl, ($C_1$-$C_8$) substituted alkyl, or $R^7$ and $R^8$ together form a five-, six-, or seven-membered heterocycle; and
in the compound of Structure 29,
$R^{24}$ is ($C_1$-$C_8$)alkyl or ($C_1$-$C_8$)substituted alkyl;
$R^{25}$ is ($C_1$-$C_8$)alkyl, ($C_1$-$C_8$)substituted alkyl or $CH_2SO_3H$; and
the dashed line represents an optional double bond.

18. The compound according to claim 17, wherein X is —OH, —$OR^{11}$, or $OC(O)R^{15}$.

19. The compound according to claim 17, wherein, in the compound of Structure 28, $R^7$ and $R^8$ are independently selected from H or ($C_1$-$C_8$)alkyl.

20. The compound according to claim 17, wherein, in the compound of Structure 29, $R^{24}$ and $R^{25}$ are ($C_1$-$C_8$)alkyl.

21. The compound according to claim 17, wherein X is —$OR^{11}$ and $R^{11}$ represents —$P(NR^{22}R^{23})OCH_2$ $CH_2$ -EWG, wherein
EWG is an electron withdrawing group and $R^{22}$, and $R^{23}$ are independently selected from —$CH_3$, —$CH_2CH_3$, —$CH(CH_3)_2$, or $R^{22}$ and $R^{23}$ together form a heterocycle.

22. The compound according to claim 17, wherein the compound is of Structure 27.

23. The compound according to claim 17, wherein the compound is of Structure 28.

24. The compound according to claim 17, wherein the compound is of Structure 29.

25. A coumarin-CPG compound of Structure 150, wherein the coumarin-CPG compound is of Structure 150,

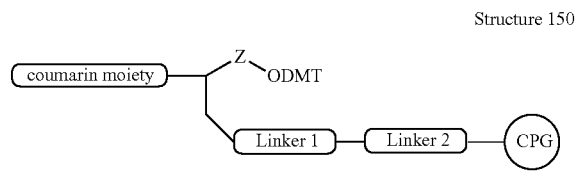

Structure 150 wherein the coumarin moiety is of structure 153, 154 or 155,

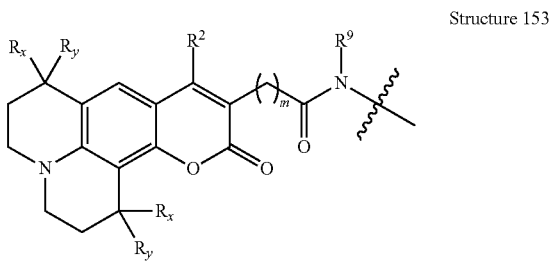

Structure 153

Structure 154

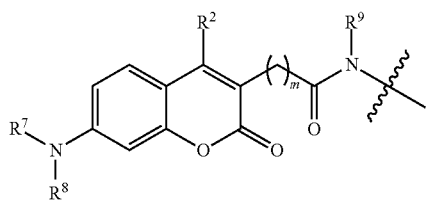

Structure 155

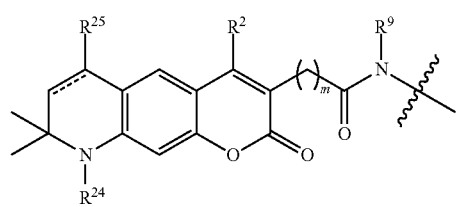

wherein:
m is 1, 2, 3, 4, 5, 6, 7, 8, 9 or 10;
$R^2$ is H or $CH_3$;
$R^9$ is $CH_3$, $CH_2CH_3$ or $CH(CH_3)_2$;
in the moiety of Structure 153, $R_x$ and $R_y$ are independently H or $CH_3$;
in the moiety of Structure 154, $R^7$ and $R^8$ are independently selected from H, $(C_1-C_8)$alkyl, $(C_1-C_8)$substituted alkyl, or $R^7$ and $R^8$ together form a four-, five-, six-, or seven-membered heterocycle;
in the moiety of Structure 155, $R^{24}$ is $(C_1-C_8)$alkyl or $(C_1-C_8)$substituted alkyl, $R^{25}$ is $(C_1-C_8)$alkyl, $(C_1-C_8)$ substituted alkyl or $CH_2SO_3H$ and the dashed lines represents an optional double bond;
Z is $(CH_2)_x$, wherein x is 1, 2, 3, 4, 5, 6, 7, 8, 9 or 10;
Linker 1 is selected from $OC(O)(CH_2)_yO(CH_2)_z(CO)$, $NHC(O)(CH_2)_yO(CH_2)_z(CO)$, wherein y is 1, 2, 3, 4, 5, 6, 7, 8, 9 or 10, and wherein z is 1, 2, 3, 4, 5, 6, 7, 8, 9 or 10; and
Linker 2 is selected from $NH(CH_2)_a$, wherein a is 1, 2, 3, 4, 5, 6, 7, 8, 9 or 10.

* * * * *

SEQUENCE LISTING

```
<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: Synthetic DNA

<400> SEQUENCE: 1
cgatctgaat agctt                                                    15

<210> SEQ ID NO 2
<211> LENGTH: 10
<212> TYPE: DNA
<213> ORGANISM: Artificial Sequence
<220> FEATURE:
<223> OTHER INFORMATION: Synthetic DNA

<400> SEQUENCE: 2
tttttttttt                                                          10
```